United States Patent
Nam et al.

(10) Patent No.: US 10,703,718 B2
(45) Date of Patent: *Jul. 7, 2020

(54) 5-BROMO-INDIRUBINS

(71) Applicant: City of Hope, Duarte, CA (US)

(72) Inventors: Sangkil Nam, Tujunga, CA (US); David Horne, Altadena, CA (US); Jun Xie, Duarte, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/893,488

(22) Filed: Feb. 9, 2018

(65) Prior Publication Data

US 2018/0170870 A1 Jun. 21, 2018

Related U.S. Application Data

(63) Continuation of application No. 14/659,286, filed on Mar. 16, 2015, now abandoned.

(60) Provisional application No. 61/953,169, filed on Mar. 14, 2014.

(51) Int. Cl.
| | |
|---|---|
| *A61K 31/404* | (2006.01) |
| *C07D 209/40* | (2006.01) |
| *C07D 403/04* | (2006.01) |
| *C07D 209/34* | (2006.01) |

(52) U.S. Cl.
CPC .................. *C07D 209/40* (2013.01)

(58) Field of Classification Search
CPC .. A61K 31/404; C07D 209/40; C07D 403/04; C07D 209/34
USPC ........................ 514/414, 418; 548/483, 486
See application file for complete search history.

(56) References Cited

U.S. PATENT DOCUMENTS

| | | | |
|---|---|---|---|
| 4,861,760 A | 8/1989 | Mazuel et al. | |
| 4,911,920 A | 3/1990 | Jani et al. | |
| 5,212,162 A | 5/1993 | Missel et al. | |
| 5,403,841 A | 4/1995 | Lang et al. | |
| 2008/0227640 A1 | 9/2008 | Bastiaans et al. | |
| 2010/0331327 A1 | 12/2010 | Meijer et al. | |
| 2011/0136808 A1 | 6/2011 | Meijer et al. | |
| 2015/0259288 A1 | 9/2015 | Nam et al. | |
| 2016/0068517 A1 | 3/2016 | Jove et al. | |
| 2018/0170915 A1* | 6/2018 | Jove ..................... C07D 401/04 |

FOREIGN PATENT DOCUMENTS

| | | | | |
|---|---|---|---|---|
| EP | 2 149 553 A1 | 2/2010 | | |
| EP | 2 149 553 B1 | 2/2010 | | |
| EP | 2 518 139 A1 | 10/2012 | | |
| EP | 2 733 140 A1 | 5/2014 | | |
| JP | 2007-522114 A | 8/2007 | | |
| WO | WO-01/37819 A2 | 5/2001 | | |
| WO | WO-01/37819 A3 | 5/2001 | | |
| WO | WO-2005/069933 A2 | 8/2005 | | |
| WO | WO-2005/069933 A3 | 8/2005 | | |
| WO | WO-2005/107466 A1 | 11/2005 | | |
| WO | WO-2007/099402 A2 | 9/2007 | | |
| WO | WO-2007/099402 A3 | 9/2007 | | |
| WO | WO-2010013168 A1 * | 2/2010 | ........... | C07D 209/40 |
| WO | WO-2013/011841 A1 | 1/2013 | | |
| WO | WO-2014/153023 A1 | 9/2014 | | |

OTHER PUBLICATIONS

Ginzinger, W., A. Egger, G. Muhlgassner, V. Arion, M. Jakupec, M. Galanski, W. Berger and B. Keppler, "Water-soluble cationic derivatives of Indirubin, the active anticancer componenet from Indigo naturalis" Chem. & Biodiver. (2012), 9: pp. 2175-2185. (Year: 2012).*

Ginzinger et al., "Water-Soluble Cationic Derivatives of Indirubin, the Active Anticancer Component from Indigo naturalis" Chem. & Biodiver. (2012), 9: pp. 2175-2185. (Year: 2012).*

Al-Muhammed, J. et al. (May-Jun. 1996). "In-vivo studies on dexamethasone sodium phosphate liposomes," *J Microencapsul* 13(3):293-306.

Bagrintseva, K. et al. (Mar. 15, 2004, e-published Nov. 6, 2003). "Mutations in the tyrosine kinase domain of FLT3 define a new molecular mechanism of acquired drug resistance to PTK inhibitors in FLT3-ITD-transformed hematopoietic cells," *Blood* 103(6):2266-2275.

Beauchard, A. et al. (2006). "Synthesis of novel 5-substituted indirubins as prote in kinase inhibitors," *Bioorganic & Medicinal Chemistry* 14(18):6434-6443.

Berge, S.M. et al. (Jan. 1977). "Pharmaceutical salts" *J Pharm Sci* 66(1)1-19.

Choi, S.J. et al. (Mar. 15, 2010, e-published Jan. 20, 2010). "Indirubin derivatives as potent FLT3 inhibitors with antiproliferative activity of acute myeloid leukemic cells," *Bioorg Med Chem Lett* 20(6):2033-2037.

Chonn, A. et al. (Dec. 1995). "Recent advances in liposomal drug-delivery systems," *Curr Opin Biotechnol* 6(6):698-708.

Deininger, M.W. et al. (Nov. 15, 2000). "The molecular biology of chronic myeloid leukemia," *Blood* 96(10):3343-3356.

Eyles, J.E. et al. (Jul. 1997). "Oral delivery and fate of poly(lactic acid) microsphere-encapsulated interferon in rats," *J Pharm Pharmacol* 49(7):669-674.

(Continued)

*Primary Examiner* — Matthew P Coughlin
*Assistant Examiner* — Sagar Patel
(74) *Attorney, Agent, or Firm* — Mintz, Levin, Cohn, Ferris, Glovsky and Popeo, P.C.; Irina E. Britva

(57) ABSTRACT

Disclosed herein are compositions and methods for treating cancer, FLT3-AML, and CML.

18 Claims, 11 Drawing Sheets

Specification includes a Sequence Listing.

(56) References Cited

OTHER PUBLICATIONS

Gao, Z.H. et al. (Jun. 1995). "Controlled release of a contraceptive steroid from biodegradable and injectable gel formulations: in vitro evaluation," *Pharm Res* 12(6):857-863.

Ginzinger, W. et al. (Oct. 2012). "Water-Soluble Cationic Derivatives of Indirubin, the Active Anticancer Component from *Indigo naturalis*," *Chemistry & Biodiversity* 9(10):2175-2185.

Goldman, J.M. et al. (Oct. 9, 2003). "Chronic myeloid leukemia—advances in biology and new approaches to treatment," *N Engl J Med* 349(15):1451-1464.

Griffith, J. et al. (Jan. 30, 2004). "The structural basis for autoinhibition of FLT3 by the juxtamembrane domain," *Mol Cell* 13(2):169-178.

International Search Report dated Aug. 26, 2014 for PCT Application No. PCT/US2014/028730, filed Mar. 14, 2014, 4 pages.

Kurzrock, R. et al. (May 20, 2003). "Philadelphia chromosome-positive leukemias: from basic mechanisms to molecular therapeutics," *Ann Intern Med* 138(10):819-830.

Liu, L. et al. (Nov. 2012, e-published Aug. 16, 2012). "A novel 7-bromoindirubin with potent anticancer activity suppresses survival of human melanoma cells associated with inhibition of STAT3 and Akt signaling," *Cancer Biol Ther* 13(13):1255-1261.

Liu, L. et al. (Feb. 2014, e-published Nov. 1, 2013). "MLS-2384, a new 6-bromoindirubin derivative with dual JAK/Src kinase inhibitory activity, suppresses growth of diverse cancer cells," *Cancer Biol Ther* 15(2):178-184.

Olivier, D. et al. (Mar. 2008, e-published Jan. 22, 2008). "Photoreactivity of indirubin derivatives," *Photochem Photobiol Sci* 7(3):328-326.

Ostro, M.J. et al. (Aug. 1989). "Use of liposomes as injectable-drug delivery systems," *Am J Hosp Pharm* 46(8):1576-1587.

Rao, K.P. (1995). "Recent developments of collagen-based materials for medical applications and drug delivery systems," *J Biomater Sci Polym Ed* 7(7):623-645.

Smith, C.C. et al. (Apr. 18, 2013, e-published Feb. 21, 2013). "Activity of ponatinib against clinically-relevant AC220-resistant kinase domain mutants of FLT3-ITD," *Blood* 121(16):3165-3171.

Vougogiannopoulou, K. et al. (Oct. 23 2008, e-published Sep. 25, 2008). "Soluble 3',6-substituted indirubins with enhanced selectivity toward glycogen synthase kinase-3 alter circadian period," *J Med Chem* 51(20):6421-6431.

Written Opinion dated Aug. 26, 2014 for PCT Application No. PCT/US2014/028730, filed Mar. 14, 2014, 11 pages.

Xingi, E. et al. (Oct. 2009, e-published May 13, 2009). "6-Br-5methylindirubin-3'oxime (5-Me-6-BIO) targeting the leishmanial glycogen synthase kinase-3 (GSK-3) short form affects cell-cycle progression and induces apoptosis-like death: exploitation of GSK-3 for treating leishmaniasis," *International Journal for Parasitology* 39(12):1289-1303.

\* cited by examiner

FIGH. 2B

IC$_{50}$ values (μM)

|  | DU145 | A2058 | SKOV3 | T315I mutant KCL22 CML |
|---|---|---|---|---|
| 5IN-6NC1 | 3.24 | >5 | 3.75 | 1.94 |
| 5IN-1NH1 | 0.035 | 0.077 | 0.174 | 0.052 |
| 5IN-6NNC6 | 5 | >5 | 4.56 | 5 |
| 5IN6NNC7 | >5 | >5 | >5 | >5 |

5-BROMO-INDIRUBINS

CROSS-REFERENCES TO RELATED APPLICATIONS

This application is a continuation of U.S. Non-provisional Application No. 14/659,286, filed Mar. 16, 2015, which claims the benefit of U.S. Provisional Application No. 61/953,169, filed Mar. 14, 2014, which are incorporated herein by reference in their entireties and for all purposes.

REFERENCE TO A "SEQUENCE LISTING," A TABLE, OR A COMPUTER PROGRAM LISTING APPENDIX SUBMITTED ON A COMPACT DISK

The Sequence Listing written in file 48440-651C01US_ST25.TXT, created on Feb. 9, 2018, 28,358 bytes, machine format IBM-PC, MS-Windows operating system, is hereby incorporated by reference.

BACKGROUND OF THE INVENTION

Cancer is a significant cause of death worldwide. In 2008, cancer accounted for an estimated 13% of worldwide deaths. Lung, prostate, and colorectal cancer are the most common forms of cancer in men and accounted for 40% of all cancers in men in 2008. Breast, colorectal, and cervical cancers made up more than 40% of all cancers in women in the same year. Overall, lung cancer is the most common cancer. Protein kinases are involved in many signal transduction and other cellular processes. Disregulation of kinase activity has been found to be associated with many forms of cancer.

FLT3-internal tandem duplication (ITD) mutations in juxtamembrane domain are detected in approximately 25% of acute myeloid leukemia (AML) patients. In addition, point mutations are observed in approximately 5%-10% of AML patients. Among these point mutations, the FLT3-D835Y mutation is predominant. The ITD mutation constitutively activates FLT3 and is associated with poor outcomes and higher relapse rate of AML in patients. Thus, there is a need in the art for treatment options for AML patients with the FLT3 mutations, including FLT3-ITD mutant kinase mutations. Provided herein are solutions to these and other problems in the art.

BRIEF SUMMARY OF THE INVENTION

Accordingly, herein are provided, inter alia, methods for treating AML expressing FLT3-kinase and other cancers.

Provided herein are compositions having the formula:

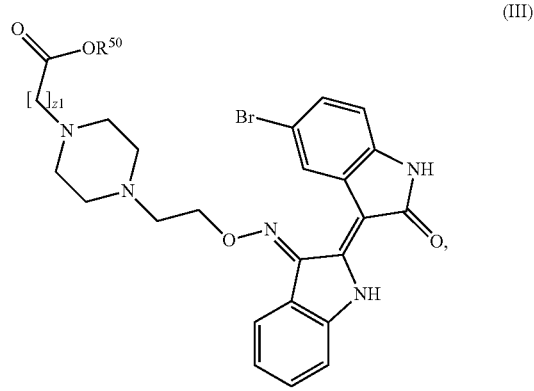

(III)

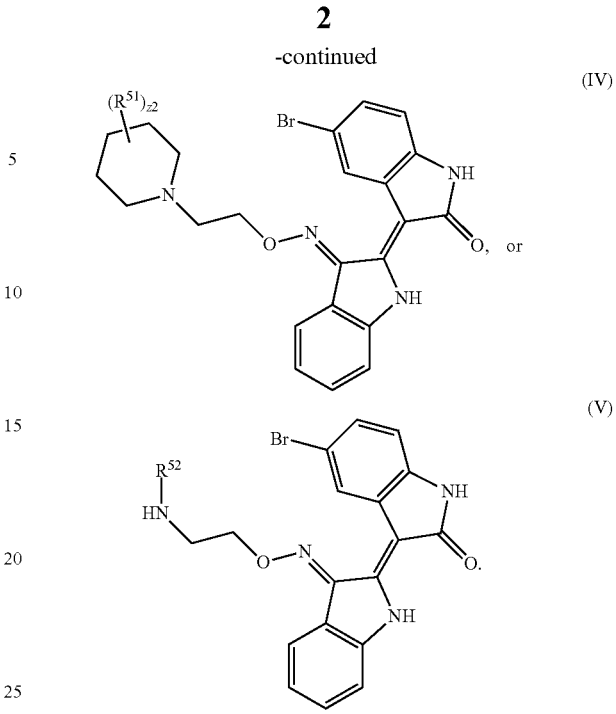

In the compound of formula (III), $R^{50}$ is hydrogen, halogen, $-CF_3$, $-CN$, $-OH$, $-NH_2$, $-COOH$, $-CH_2COOH$, $-CONH_2$, $-NO_2$, $-SH$, $-OCF_3$, $-OCHF_2$, or unsubstituted alkyl. In the compound of formula (IV), $R^{51}$ is hydrogen, oxo, halogen, $-CF_3$, $-CN$, $-OH$, $-NR^{51A}R^{51B}$, $-COOH$, $-CH_2COOH$, $-CONH_2$, $-NO_2$, $-SH$, $-OCF_3$, $-OCHF_2$, unsubstituted alkyl, or unsubstituted heteroalkyl. $R^{51A}$ and $R^{51B}$ are independently hydrogen or substituted or unsubstituted (e.g. unsubstituted) alkyl (e.g. $C_1$-$C_{10}$ alkyl). In the compound of formula (V), $R^{52}$ is halogen, $-CF_3$, $-CN$, $-OH$, $-NH_2$, $-COOH$, $-CONH_2$, or unsubstituted alkyl. The symbols z1 and z2 are independently 0, 1, 2, 3, 4, or 5. The compounds of formula (III), (IV), or (V) include pharmaceutically acceptable salts thereof.

In another aspect is a method of treating cancer by administering to a subject in need thereof an effective amount of a compound having formula (III), (IV), or (V), including embodiments and pharmaceutically acceptable salts thereof.

Also provided herein are methods of treating acute myeloid leukemia expressing FLT3-kinase in a subject in need thereof. In one aspect, the method includes administering an effective amount of a compound having the formula (I), including embodiments and pharmaceutically acceptable thereof. In another aspect, is the method includes administering an effective amount of a compound having the formula (III), (IV), or (V), as described herein, including embodiments and pharmaceutically acceptable thereof. In yet another aspect, the method includes administering an effective amount of a compound having the formula (1289), (5IN-6NC1), (5IN-1NH1), (5IN-6NNC6), (5IN-6NNC7), (5IN-1NH2), or (5IN-6NC2), including embodiments thereof.

Also provided herein are methods of treating acute myeloid leukemia expressing FLT3-mutant kinase, wherein the FLT3-mutant kinase is a FLT3-TKD mutant kinase as described herein in a subject in need thereof. In one aspect, the method includes administering an effective amount of a compound having the formula (I), including embodiments and pharmaceutically acceptable salts thereof. In another aspect, the method includes administering an effective amount of a compound having the formula (III), (IV), or (V) including embodiments and pharmaceutically acceptable salts thereof. In yet another aspect, the method includes administering an effective amount of a compound having the formula (1289), (5IN-6NC1), (5IN-1NH1), (5IN-6NNC6), (5IN-6NNC7), (5IN-1NH2), or (5IN-6NC2), including embodiments thereof.

Also provided herein are methods of treating acute myeloid leukemia expressing FLT3-mutant kinase, wherein the FLT3-mutant kinase is a FLT3-ITD mutant kinase as described herein in a subject in need thereof. In one aspect, the method includes administering an effective amount of a compound having the formula (I), including embodiments and pharmaceutically acceptable salts thereof. In another aspect, the method includes administering an effective amount of a compound having the formula (III), (IV), or (V) including embodiments and pharmaceutically acceptable salts thereof. In yet another aspect, the method includes administering an effective amount of a compound having the formula (1289), (5IN-6NC1), (5IN-1NH1), (5IN-6NNC6), (5IN-6NNC7), (5IN-1NH2), or (5IN-6NC2), including embodiments thereof.

Also provided herein are methods of treating acute lymphoblastic Leukemia (ALL), which expresses FLT3-kinase, in a subject in need thereof. In one aspect method includes administering an effective amount of a compound having formula (I) as described herein including embodiments thereof and pharmaceutically acceptable salts thereof. In another aspect, the method includes administering an effective amount of a compound having formula (III), (IV), or (V) as described herein including embodiments thereof and pharmaceutically acceptable salts thereof. In yet another aspect, the method includes administering an effective amount of a compound having the formula (1289), (5IN-6NC1), (5IN-1NH1), (5IN-6NNC6), (5IN-6NNC7), (5IN-1NH2), or (5IN-6NC2), including embodiments thereof.

Provided herein are methods of treating chronic myelogenous leukemia (CML) expressing ABL1-kinase in a subject in need thereof. In one aspect, the method includes administering an effective amount of a compound having the formula (I), including embodiments and pharmaceutically acceptable thereof. In another aspect, the method includes administering an effective amount of a compound having the formula (II), (III), or (IV), as described herein, including embodiments and pharmaceutically acceptable thereof. In yet another aspect, the method includes administering an effective amount of a compound having the formula 5IN-1NH1 or 5IN-1-NH1s as described herein, including embodiments and pharmaceutically acceptable thereof Provided herein are methods of modulating activity of a FLT3-kinase. In one aspect, the method includes contacting a FLT3-kinase with a compound having formula (I), including embodiments and pharmaceutically acceptable salts thereof. In another aspect, the method includes contacting a FLT3-kinase with a compound having formula (III), (IV), or (V), including embodiments and pharmaceutically acceptable salts thereof.

Provided herein are methods of modulating activity of a type III receptor tyrosine kinase. In one aspect, the method includes contacting a type III receptor tyrosine kinase with a compound having formula (I), including embodiments and pharmaceutically acceptable salts thereof. In another aspect, the method includes contacting a type III receptor tyrosine kinase with a compound having formula (III), (IV), or (V), including embodiments and pharmaceutically acceptable salts thereof.

BRIEF DESCRIPTION OF THE DRAWINGS

FIG. 1A) A2058 melanoma cells exposed to varying concentrations of compounds 5IN-1NH1 and 5IN-1NH1s; $IC_{50}$ values 5IN-1NH1: 77.2 nM, 5IN-1NH1s: 88.9 nM; FIG. 1B) DU145 prostate cancer cells exposed to varying concentrations of compounds 5IN-1NH1 and 5IN-1NH1s; $IC_{50}$ values 5IN-1NH1: 35.7 nM, 5IN-1NH1s: 44.7 nM.

FIGS. 2A-2B: $IC_{50}$ value determination for 50% inhibition of viability of solid tumor cells (lung cancer and breast cancer): FIG. 2A) A549 lung cancer cells exposed to varying concentrations of compounds 5IN-1NH1 and 5IN-1NH1s; $IC_{50}$ values 5IN-1NH1: 66.5 nM, 5IN-1NH1s: 46.1 nM; FIG. 2B) MDA-MB-231 breast cancer cells exposed to varying concentrations of compounds 5IN-1NH1 and 5IN-1NH1s; $IC_{50}$ values 5IN-1NH1: 49.5 nM, 5IN-1NH1s: 33 nM.

FIG. 4A) MV4-11 AML cells exposed to varying concentrations of compounds 5IN-1NH1 and 5IN-1NH1s; $IC_{50}$ values 5IN-1NH1: 7.8 nM, 5IN-1NH1s: 3.7 nM; FIG. 4B) MOLM13 AML cells exposed to varying concentrations of compounds 5IN-1NH1 and 5IN-1NH1s; $IC_{50}$ values 5IN-1NH1: 11.3 nM, 5IN-1NH1s: 7.5 nM.

FIG. 5A) structure of exemplary compounds disclosed herein; FIG. 5B) $IC_{50}$ values for DU145 prostate cancer cells, A2058 melanoma cells, SKOV3 ovarian cancer cells, and T315I ABL1 mutant KCL22 CML cells for compounds 5IN-6NC1, 5IN-1NH1, 5IN-6NNC6, and 5IN-6NNC7.

FIG. 6A) KCL22 CML cells exposed to varying concentrations of compound 5IN-1NH1; $IC_{50}$ value: 57.4 nM, 5IN-1NH1s: $IC_{50}$ value: 72.8 nM; FIG. 6B) T315I ABL1 mutant KCL22 CML cells exposed to varying concentrations of compound 5IN-1NH1; $IC_{50}$ value: 52.3 nM, 5IN-1NH1s: $IC_{50}$ value 52.7 nM.

FIG. 7A) Effect of 5IN-1NH2 (0.25 uM and 1 uM concentrations) and 5IN-6NC2 (0.25 uM and 1 uM concentrations) on A2058 melanoma cells; FIG. 7B) Effect of 5IN-1NH2 (0.25 uM and 1 uM concentrations) and 5IN-6NC2 (0.25 uM and 1 uM concentrations) on DU145 prostate cancer cells.

FIG. 10A: MV4-11 AML cells; FIG. 10B: MOLM-13 AML cells.

FIG. 11A) Efficacy of compound (1289) on MV4-11 AML SQ xenografts in vivo as a function of time (days); FIG. 11B) Histogram depicting tumor weight (g) for vehicle (left column) and compound (1289) regimen (25 mg/kg).

DETAILED DESCRIPTION OF THE INVENTION

Figure 1A:
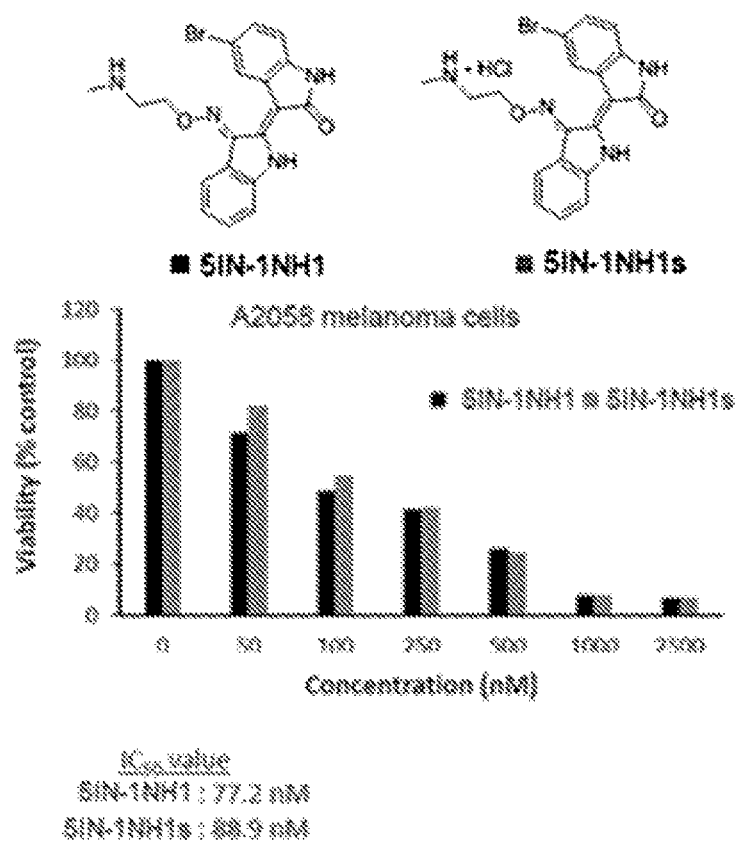
FIGS. 1A-1B: $IC_{50}$ value determination for 50% inhibition of viability of solid tumor cells (melanoma and prostate cancer)
Figure 1B:
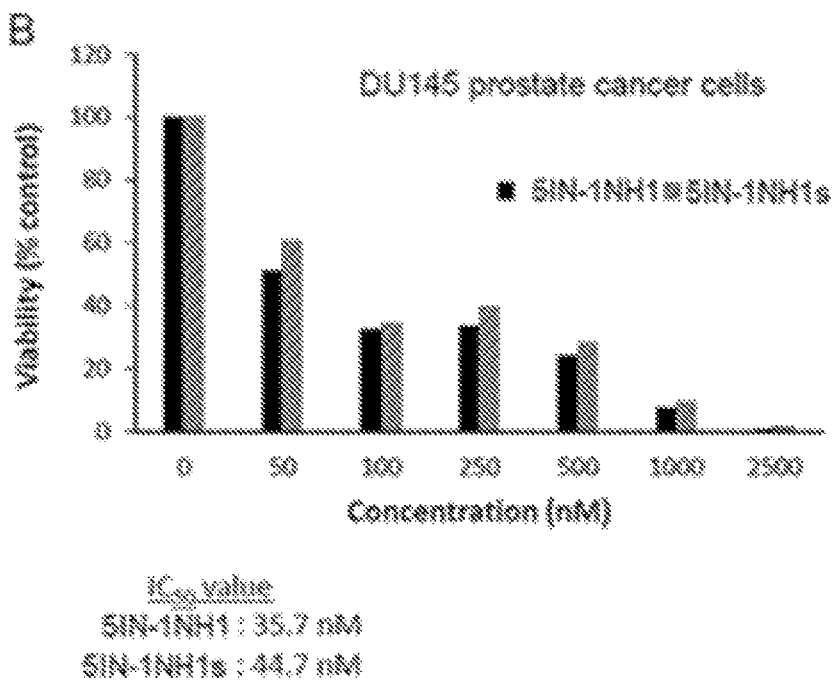
Figure 2A:
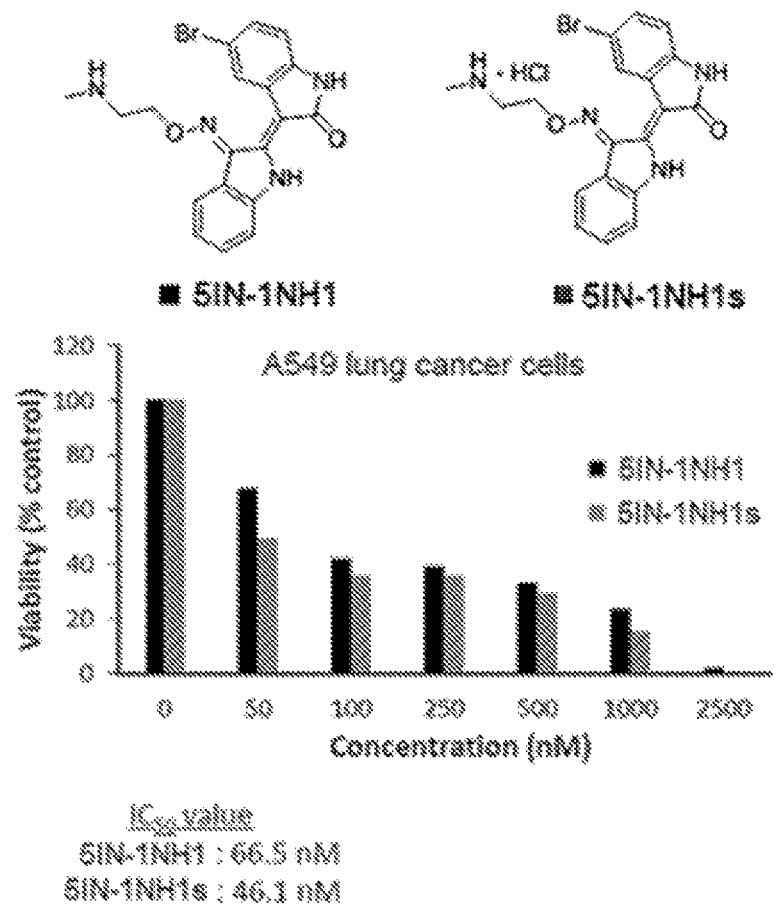
Figure 2A:
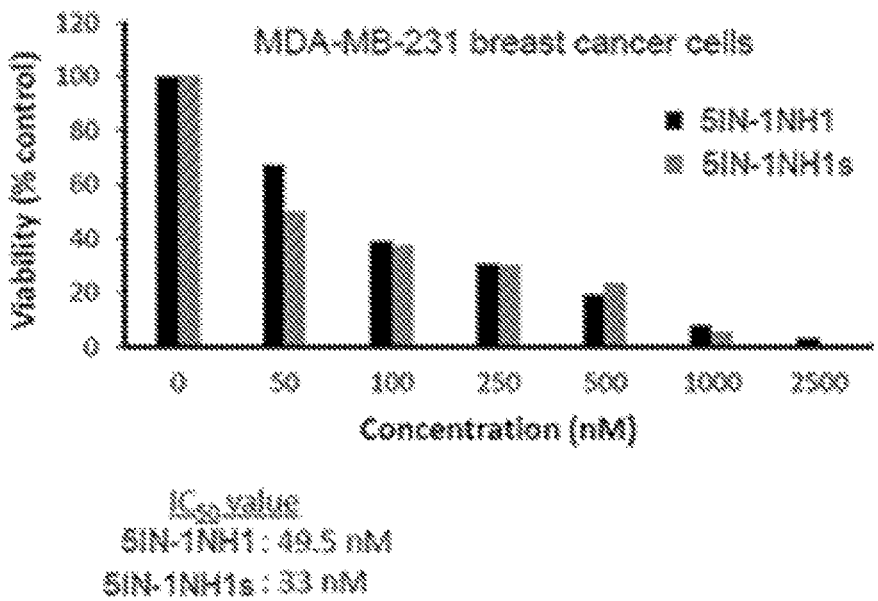
Figure 3:
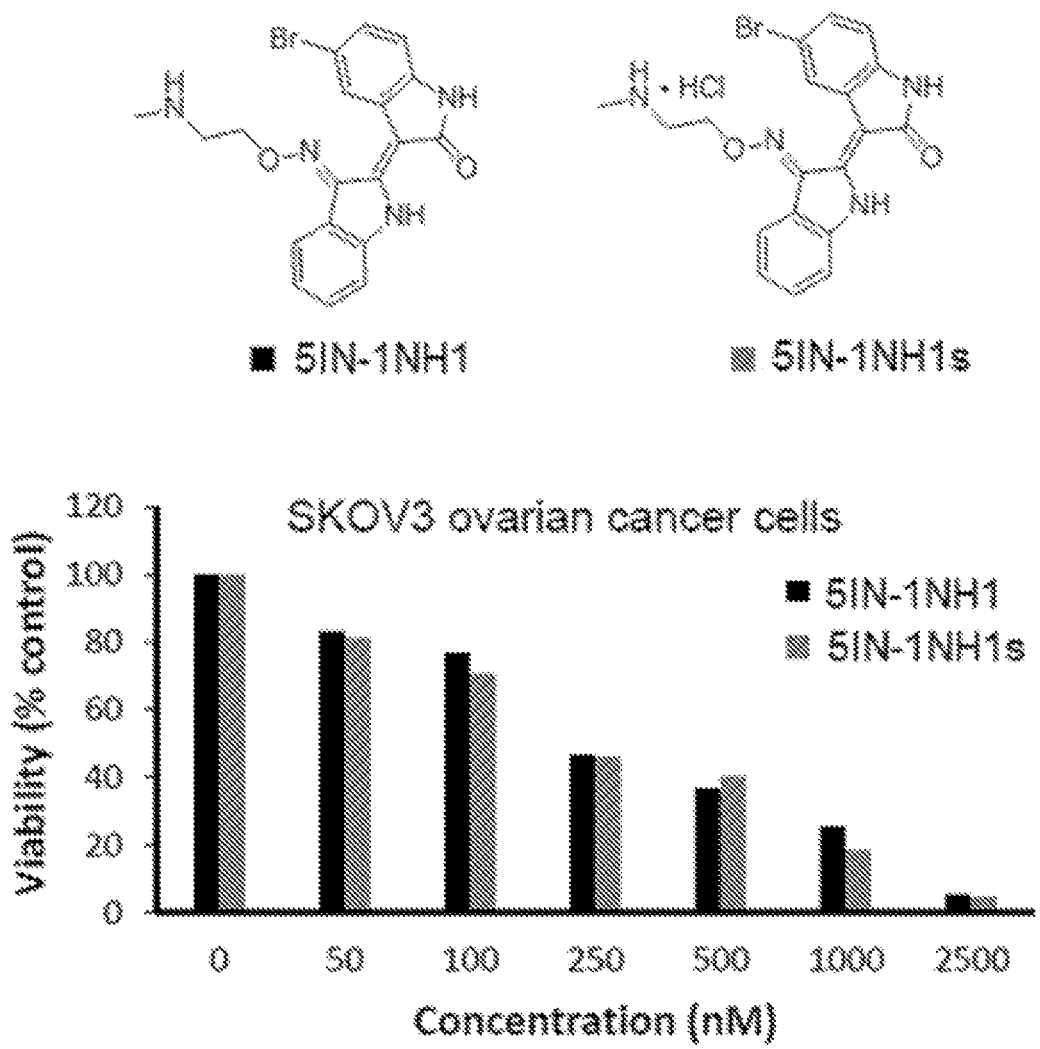
FIG. 3: $IC_{50}$ value determination for 50% inhibition of viability of solid tumor cells (ovarian cancer): SKOV3 ovarian cancer cells exposed to varying concentrations of compounds 5IN-1NH1 and 5IN-1NH1s; $IC_{50}$ values 5IN-1NH1: 174 nM, 5IN-1NH1s: 169.4 nM.
Figure 4A:
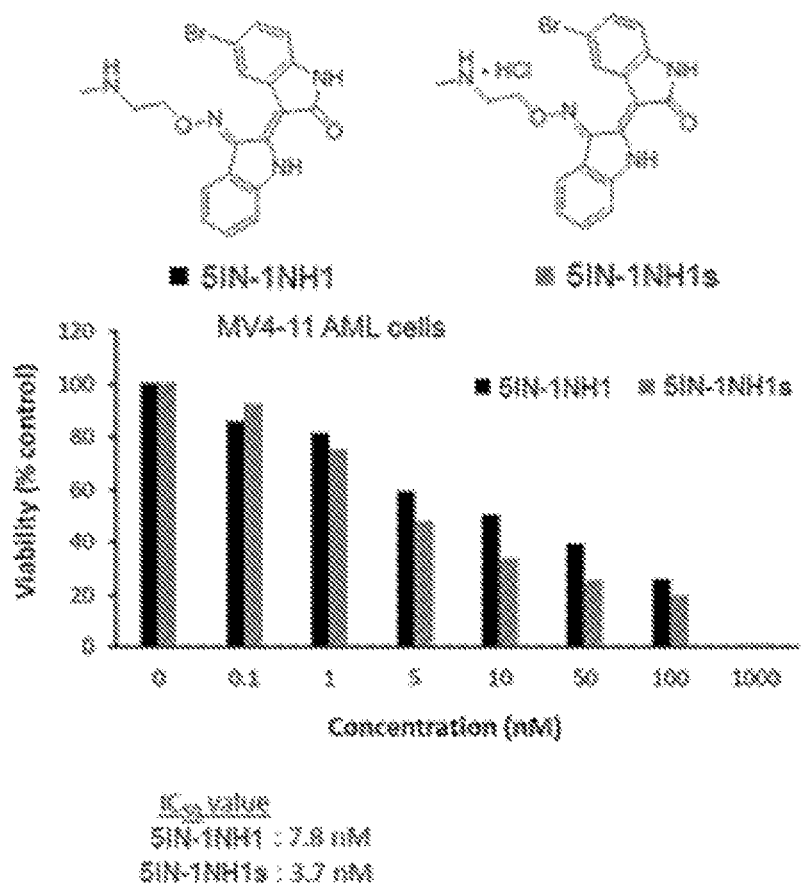
FIGS. 4A-4B: $IC_{50}$ value determination for 50% inhibition of viability of FLT3-ITD mutant kinase AML cells.
Figure 4B:
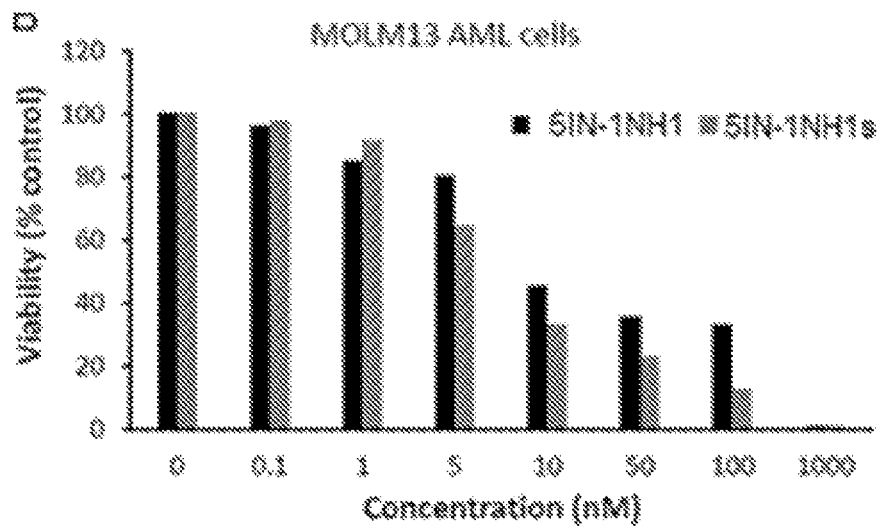

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include di- and multivalent radicals, having the number of carbon atoms designated (i.e., C$_1$-C$_{10}$ means one to ten carbons). Alkyl is not cyclized. Examples of saturated hydrocarbon radicals include, but are not limited to, groups such as methyl, ethyl, n-propyl, isopropyl, n-butyl, t-butyl, isobutyl, sec-butyl, (cyclohexyl) methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butyryl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Heteroalkyl is not cyclized. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Cycloalkyl and heteroalkyl are non-aromatic rings. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring).

A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of heteroaryl groups include pyridinyl, pyrimidinyl, thiophenyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocyloalkyl-heteroaryl, fused ring heterocycloalkyl-cycloalkyl, or fused ring heterocycloalkyl-heterocycloalkyl may each independently be unsubstituted or substituted with one or more of the substituents described herein.

The term "oxo," as used herein, means an oxygen that is double bonded to a carbon atom.

The term "alkylsulfonyl," as used herein, means a moiety having the formula —S(O$_2$)-R', where R' is a substituted or unsubstituted alkyl group as defined above. R' may have a specified number of carbons (e.g., "C$_1$-C$_4$ alkylsulfonyl").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R —SR', -halogen, —SiR'R"R'", —OC(O)R', —C(O)R', —CO$_2$R', —CONR'R", —OC(O)NR'R", —NR"C(O)R', —NR"—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR'NR'"R"", —CN, —NO$_2$, in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl.

Similar to the substituents described for the alkyl radical, substituents for the aryl and heteroaryl groups are varied and are selected from, for example: —OR', —NR'R", —SR', -halogen, —SiR"R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR'NR'"R"", —CN, —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula —T—C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula —A—(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, and unsubstituted heteroaryl.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention.

Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)-or (S)- or, as (D)- or (L)-for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C— or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}$H), iodine-125 ($^{125}$I), or carbon-14 ($^{14}$C). All isotopic variations of the compounds of the present invention, whether radioactive or not, are encompassed within the scope of the present invention.

The symbol "⌇" denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, the certain methods presented herein successfully treat cancer by decreasing the incidence of cancer and or causing remission of cancer. The term "treating," and conjugations thereof, include prevention of an injury, pathology, condition, or disease.

A "therapeutically effective amount" or "effective amount" is an amount sufficient for a compound to accomplish a stated purpose relative to the absence of the compound (e.g. achieve the effect for which it is administered, treat a disease, reduce enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a compound as described herein and a protein or kinase (e.g. FLT3). In embodiments contacting includes allowing a compound described herein to interact with a protein or enzyme that is involved in a signaling pathway (e.g. STAT pathway).

The term "modulation", "modulate", or "modulating" are used in accordance with their plain ordinary meaning and refer to the act of changing or varying one or more properties. For example, modulating may refer to decreasing the level of a target molecule or the function of a target molecule (e.g. a target may be a kinase (e.g. FLT3) and the function may be to phosphorylate a molecule or the target may be a kinase and the function may be the function of a downstream signaling pathway including a STAT, STAT3, or STAT5).

The terms "FLT3-kinase" or "FLT3" are used interchangeably herein and according to their common, ordinary meaning and refer to proteins of the same or similar names, homologs, isoforms, and functional fragments thereof, so long as such fragments retain FLT3 (e.g. fms-like tyrosine kinase 3) activity. The term includes any recombinant or naturally-occurring form of FLT3 (e.g. GI: 121114304: SEQ ID NO:1), FLT3 preprotein, FLT3 truncation, FLT3 domain (e.g. juxtamembrane domain, activation loop, transmembrane domain, or kinase domain), post-translationally modified FLT3, or variants thereof that maintain FLT3 activity (e.g. within at least 30%, 40%, 50%, 60%, 70%, 80%, 90%, 95%, or 100% activity compared to FLT3). A "FLT3-wild type kinase" as used herein refers to a full-length or functional fragment (e.g. at least 50 contiguous amino acids in length) of FLT3 having sequence identity (e.g. 70%, 75%, 80%, 85%, 90%, 95%, 96%, 97%, 98%, 99%, or 100%) to SEQ ID NO:1, that has FLT3 activity. FLT3-kinase is found in certain subtypes of AML and ALL as described herein and may include at least one mutation as described herein.

```
Sequence of SEQ ID NO: 1:
MPALARDGGQ LPLLVVFSAM IFGTITNQDL PVIKCVLINH

KNNDSSVGKS SSYPMVSESP EDLGCALRPQ SSGTVYEAAA

VEVDVSASIT LQVLVDAPGN ISCLWVFKHS SLNCQPHFDL

QNRGVVSMVI LKMTETQAGE YLLFIQSEAT NYTILFTVSI

RNTLLYTLRR PYFRKMENQD ALVCISESVP EPIVEWVLCD

SQGESCKEES PAVVKKEEKV LHELFGTDIR CCARNELGRE

CTRLFTIDLN QTPQTTLPQL FLKVGEPLWI RCKAVHVNHG

FGLTWELENK ALEEGNYFEM STYSTNRTMI RILFAFVSSV

ARNDTGYYTC SSSKHPSQSA LVTIVEKGFI NATNSSEDYE

IDQYEEFCFS VRFKAYPQIR CTWTFSRKSF PCEQKGLDNG

YSISKFCNHK HQPGEYIFHA ENDDAQFTKM FTLNIRRKPQ

VLAEASASQA SCFSDGYPLP SWTWKKCSDK SPNCTEEITE

GVWNRKANRK VFGQWVSSST LNMSEAIKGF LVKCCAYNSL

GTSCETILLN SPGPFPFIQD NISFYATIGV CLLFIVVLTL

LICHKYKKQF RYESQLQMVQ VTGSSDNEYF YVDFREYEYD

LKWEFPRENL EFGKVLGSGA FGKVMNATAY GISKTGVSIQ

VAVKMLKEKA DSSEREALMS ELKMMTQLGS HENIVNLLGA

CTLSGPIYLI FEYCCYGDLL NYLRSKREKF HRTWTEIFKE

HNFSFYPTFQ SHPNSSMPGS REVQIHPDSD QISGLHGNSF

HSEDEIEYEN QKRLEEEEDL NVLTFEDLLC FAYQVAKGME

FLEFKSCVHR DLAARNVLVT HGKVVKICDF GLARDIMSDS

NYVVRGNARL PVKWMAPESL FEGIYTIKSD VWSYGILLWE

IFSLGVNPYP GIPVDANFYK LIQNGFKMDQ PFYATEEIYI

IMQSCWAFDS RKRPSFPNLT SFLGCQLADA EEAMYQNVDG

RVSECPHTYQ NRRPFSREMD LGLLSPQAQV EDS.
```

A "FLT3-mutant kinase" as used herein refers to a FLT3-kinase, or functional fragments and homologs thereof, having an amino acid mutation in SEQ ID NO:1. A FLT3-mutant kinase as used herein, refers to a FLT3-mutant kinase found in AML or ALL as described herein, including embodiments thereof. Mutations to FLT3-kinase include addition or deletion of an amino acid or substitution of an amino acid such that the FLT3-mutant kinase retains FLT3 activity. For example, a FLT3-mutant kinase may have a point mutation within SEQ ID NO:1. The point mutation may be located in the FLT3 activation loop (e.g. residues between about 604 to about 690 of SEQ ID NO:1). Griffith, *Mol Cell*, 13, 169-178, 2004; Smith, *Blood*, 2013 Apr 18;121(16):3165-71. A FLT3-mutant kinase may have a point mutation located in the tyrosine kinase domain ("TKD") (e.g. residues between about 610 to about 943) herein referred to as a FLT3-TKD mutant kinase. A FLT3-TKD mutant does not have an ITD mutation as described herein. A FLT3-TKD mutant kinase is typically constitutively active in the presence or absence of ligand.

Point mutations in a FLT3-TKD mutant kinase include, for example, mutation of residues corresponding to D835, I836, D839, S840, N841, or Y842 of SEQ ID NO:1. Accordingly, a FLT3-mutant kinase may have a D835Aaa1 mutation, where Aaa1 is an amino acid other than Asp. Aaa1 may be His, Asn, Gly, Pro, Tyr, Ala, Val, or Glu. Aaa1 may be Tyr. In embodiments, a FLT3-mutant kinase may have a I836Aaa2 mutation, where Aaa2 is an amino acid other than Ile. Aaa2 may be Leu or Met. In embodiments, a FLT3-mutant kinase may have a D839Aaa3 mutation, where Aaa3 is an amino acid other than Asp. Aaa3 may be Gly. In embodiments, a FLT3-mutant kinase may have a S840Aaa4 mutation, where Aaa4 is an amino acid other than Ser. Aaa4 may be Gly. In embodiments, a FLT3-mutant kinase may have a N841Aaa5 mutation, where Aaa5 is an amino acid other than Asn. Aaa5 may be Ile, Lys, or Tyr. In embodiments, a FLT3-mutant kinase may have a Y842Aaa6 mutation, where Aaa6 is an amino acid other than Tyr. Aaa6 may be Cys or His.

A FLT3-mutant kinase may be characterized as a FLT3-kinase having a FLT3-internal tandem duplication mutation ("ITD"). The terms "FLT3-internal tandem duplication mutant kinase" or "FLT3-ITD mutant kinase" refer to in-frame internal sequence duplications of the juxtamembrane domain (e.g. residues between about 572 and about 603 in SEQ ID NO:1) which typically result in constitutive activation of FLT3. A FLT3-ITD mutant kinase may optionally have a mutation outside the ITD (e.g. a mutation within the tyrosine kinase domain). In embodiments, a FLT3-ITD having a mutation outside the ITD is referred to as a FLT3-ITD-TKD mutant kinase.

The terms "ABL1-kinase" or "ABL1" are used interchangeably herein and according to their common, ordinary meaning and refer to proteins of the same or similar names, homologs, isoforms, and functional fragments thereof, so long as such fragments retain ABL1-kinase (e.g. Abelson murine leukemia viral oncogene homolog 1) activity. The term includes any recombinant or naturally-occurring form of ABL1-kinase (e.g. GI: 85681908: SEQ ID NO:2), ABL1-kinase preprotein, ABL1-kinase truncation, ABL1-kinase domain, ABL1-kinase translocation, post-translationally modified ABL1-kinase, ABL1-kinase domain (e.g. P-loop, kinase domain, or A-loop), or variants thereof that maintain ABL1-kinase activity (e.g. within at least 30%, 40%, 50%, 60%, 70%, 80%, 90%, 95%, or 100% activity compared to ABL1-kinase). An "ABL1-wild type kinase" as used herein refers to a full-length or functional fragment (e.g. about 50 contiguous amino acids) of ABL1-kinase having sequence identity (e.g. at least 80%, 85%, 90%, 95%, 96%, 97%, 98%, 99% or 100%) to SEQ ID NO:2, that has ABL1-kinase activity. ABL1-kinase is found in certain subtypes of CML as described herein and may include at least one mutation as described herein.

```
Sequence of SEQ ID NO: 2:
MLEICLKLVGCKSKKGLSSSSSCYLEEALQRPVASDFEPQGLSEAARWNS

KENLLAGPSENDPNLFVALYDFVASGDNTLSITKGEKLRVLGYNHNGEWC

EAQTKNGQGWVPSNYITPVNSLEKHSWYHGPVSRNAAEYLLSSGINGSFL

VRESESSPGQRSISLRYEGRVYHYRINTASDGKLYVSSESRFNTLAELVH

HHSTVADGLITTLHYPAPKRNKPTVYGVSPNYDKWEMERTDITMKHKLGG

GQYGEVYEGVWKKYSLTVAVKTLKEDTMEVEEFLKEAAVMKEIKHPNLVQ

LLGVCTREPPFYIITEFMTYGNLLDYLRECNRQEVNAVVLLYMATQISSA

MEYLEKKNFIHRDLAARNCLVGENHLVKVADFGLSRLMTGDTYTAHAGAK

FPIKWTAPESLAYNKFSIKSDVWAFGVLLWEIATYGMSPYPGIDLSQVYE

LLEKDYRMERPEGCPEKVYELMRACWQWNPSDRPSFAEIHQAFETMFQES

SISDEVEKELGKQGVRGAVSTLLQAPELPTKTRTSRRAAEHRDTTDVPEM

PHSKGQGESDPLDHEPAVSPLLPRKERGPPEGGLNEDERLLPKDKKTNLF

SALIKKKKKTAPTPPKRSSSFREMDGQPERRGAGEEEGRDISNGALAFTP

LDTADPAKSPKPSNGAGVPNGALRESGGSGFRSPHLWKKSSTLTSSRLAT

GEEEGGGSSSKRFLRSCSASCVPHGAKDTEWRSVTLPRDLQSTGRQFDSS

TFGGHKSEKPALPRKRAGENRSDQVTRGTVTPPPRLVKKNEEAADEVFKD

IMESSPGSSPPNLTPKPLRRQVTVAPASGLPHKEEAGKGSALGTPAAAEP

VTPTSKAGSGAPGGTSKGPAEESRVRRHKHSSESPGRDKGKLSRLKPAPP

PPPAASAGKAGGKPSQSPSQEAAGEAVLGAKTKATSLVDAVNSDAAKPSQ

PGEGLKKPVLPATPKPQSAKPSGTPISPAPVPSTLPSASSALAGDQPSST

AFIPLISTRVSLRKTRQPPERIASGAITKGVVLDSTEALCLAISRNSEQM

ASHSAVLEAGKNLYTFCVSYVDSIQQMRNKFAFREAINKLENNLRELQIC

PATAGSGPAATQDFSKLLSSVKEISDIVQR.
```

An "ABL1-mutant kinase" as used herein refers to a ABL1-kinase, or functional fragments and homologs thereof, having an amino acid mutation in SEQ ID NO:2 or a translocation as described herein. ABL1-mutant kinase refers to a kinase found in CML as described herein, including embodiments thereof. Mutations to an ABL1-mutant kinase include addition or deletion of an amino acid or substitution of an amino acid such that the kinase retains its activity. For example, an ABL1-mutant kinase may have at least one point mutation within SEQ ID NO:2 as described below. In embodiments, the ABL1-mutant kinase is a "BCR-ABL1 mutant kinase". A BCR-ABL1 mutant kinase as used herein refers to an ABL1-kinase derived from a translocation between chromosomes 9 and 22 resulting in a fusion protein between BCR and ABL1. (SEQ ID NO:3). In embodiments, the BCR-ABL1 mutant kinase has at least 70%, 75%, 80%, 85%, 90%, 95%, 96%, 97%, 98%, 99% or 100% to SEQ ID NO:3. In embodiments, the BCR-ABL1 mutant kinase is derived from the ABL1 translocation t(9;22)(q34;q11) with BCR. Mutations of a BCR-ABL1 mutant kinase include addition or deletion of an amino acid or substitution of an amino acid such that the kinase retains its activity. For example, an BCR-ABL1-mutant kinase may have a point mutation within SEQ ID NO:3. In embodiments, the mutation may be located in a domain of the BCR-ABL1 mutant kinase (e.g. P-loop, kinase domain, or A-loop). In embodiments the point mutation may be located in at an amino acid position corresponding to Y253, E255, V268, V270, T272, Y274, D276, T277, M278, E282, F283, A288, M290, K291, E292, I293, P296, L298, V299, Q300, G303, V304, C305, T306, F311, I314, T315, E316, F317, M318, Y320, G321, D325, Y326, L327, R328, E329, Q333, E334, A337, V339, L342, M343, A344, I347, A350, M351, E352, E355, K357, N358, F359, I360, L364, E373, N374, K378, V379, A380, D381, F382, T389, T392, T394, A395, H396, A399, P402, or T406 of SEQ ID NO:2 or SEQ ID NO:3.

```
Sequence of SEQ ID NO: 3:
MLEICLKLVGCKSKKGLSSSSSCYLEEALQRPVASDFEPQGLSEAARWNS

KENLLAGPSENDPNLFVALYDFVASGDNTLSITKGEKLRVLGYNHNGEWC

EAQTKNGQGWVPSNYITPVNSLEKHSWYHGPVSRNAAEYPLSSGINGSFL
```

-continued

```
VRESESSPSQRSISLRYEGRVYHYRINTASDGKLYVSSESRFNTLAELVH

HHSTVADGLITTLHYPAPKRNKPTVYGVSPNYDKWEMERTDITMKHKLGG

GQYGEVYEGVWKKYSLTVAVKTLKEDTMEVEEFLKEAAVMKEIKHPNLVQ

LLGVCTREPPFYIITEFMTYGNLLDYLRECNRQEVNAVVLLYMATQISSA

MEYLEKKNFIHRDLAARNCLVGENHLVKVADFGLSRLMTGDTYTAHAGAK

FPIKWTAPESLAYNKFSIKSDVWAFGVLLWEIATYGMSPYPGIDRSQVYE

LLEKDYRMKRPEGCPEKVYELMRACWQWNPSDRPSFAEIHQAFETMFQES

SISDEVEKELGKQGVRGAVTTLLQAPELPTKTRTSRRAAEHRDTTDVPEM

PHSKGQGESDPLDHEPAVSPLLPRKERGPPEGGLNEDERLLPKDKKTNLF

SALIKKKKKTAPTPPKRSSSFREMDGQPERRGAGEEEGRDISNGALAFTP

LDTADPAKSPKPSNGAGVPNGALRESGGSGFRSPHLWKKSSTLTSSRLAT

GEEEGGGSSSKRFLRSCSVSCVPHGAKDTEWRSVTLPRDLQSTGRQFDSS

TFGGHKSEKPALPRKRAGENRSDQVTRGTVTPPPRLVKKNEEAADEVFKD

IMESSPGSSPPNLTPKPLRRQVTVAPASGLPHKEEAWKGSALGTPAAAEP

VTPTSKAGSGAPRGTSKGPAEESRVRRHKHSSESPGRDKGKLSKLKPAPP

PPPAASAGKAGGKPSQRPGQEAAGEAVLGAKTKATSLVDAVNSDAAKPSQ

PAEGLKKPVLPATPKPHPAKPSGTPISPAPVPLSTLPSASSALAGDQPSS

TAFIPLISTRVSLRKTRQPPERASGAITKGVVLDSTEALCLAISGNSEQM

ASHSAVLEAGKNLYTFCVSYVDSIQQMRNKFAFREAINKLENNLRELQIC

PASAGSGPAATQDFSKLLSSVKEISDIVQR.
```

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In some embodiments inhibition refers to reduction of a disease or symptoms of disease. In some embodiments, inhibition refers to a reduction in the activity of a particular protein or nucleic acid target. Thus, inhibition includes, at least in part, partially or totally blocking stimulation, decreasing, preventing, or delaying activation, or inactivating, desensitizing, or down-regulating signal transduction or enzymatic activity or the amount of a protein.

The phrase "tyrosine kinase-inhibitor resistant" when used in relation to a tyrosine kinase, refers to resistance of a tyrosine kinase such as FLT3-kinase (e.g. a FLT3-mutant kinase including FLT3-TKD mutant kinase or FLT3-ITD mutant kinase) or an ABL1-kinase (e.g. an ABL1-mutant kinase or BCR-ABL1 mutant kinase) to at least one tyrosine kinase inhibitor (e.g. a compound, polypeptide, amino acid, polynucleotide, nucleic acid, or antibody) intended to inhibit the activity or expression of the kinase (e.g. FLT3). When used with respect to cancers, the phrase refers to a cancer (e.g. AML, CML, or ALL) which is resistant to at least one tyrosine kinase inhibitor used in treatment. Thus, a tyrosine kinase-inhibitor resistant cancer as used herein may be a cancer that expresses or is caused at least in part by expression of a tyrosine kinase (e.g. a FLT3-mutant kinase, ABL1-mutant kinase or BCR-ABL1 mutant kinase as discussed herein) that is resistant to a tyrosine kinase inhibitor. In embodiments, the term refers to a tyrosine-kinase-inhibitor resistant AML. In embodiments, the term refers to a tyrosine-kinase-inhibitor resistant CML. In embodiments, the term refers to a tyrosine-kinase-inhibitor resistant ALL. Non-limiting examples of tyrosine kinase inhibitors include ABT-869, AG1295, AG1296, AGL2043, AS602868, sorafenib, lestaurtinib, AC220, TKI258, D64406, FI-700, Go6976, GTP-14564, Herbimycin A, IMC-EB10, IMC-NC7, Ki23819, KRN383, KW-2449, LS-104, MLN518, NVP-AST487, PKC412, SU5416, SU5614, sunitinib, imatinib (e.g. GLEEVEC®), dasatinib, CEP-701, or CGP-52421.

"AC220" or "Quizartinib" are used interchangeably and refer to their common and ordinary meaning as a tyrosine kinase inhibitor. Thus, an "AC220 drug resistant" kinase refers to a kinase having a mutation (e.g. a mutation of FLT3-kinase) that has sufficient activity in the presence of AC220 to impart cancer resistance. In embodiments, the AC220 drug resistant kinase is a AC220 drug resistant FLT3-mutant kinase (e.g. FLT3-TKD mutant kinase or FLT3-ITD mutant kinase). In embodiments, the AC220 drug resistant kinase is a FLT3-ITD mutant kinase as described herein and optionally includes at least one point mutation. The point mutation may be a mutation at residue corresponding to residues D835, I836, D839, S840, N841, or Y842 of SEQ ID NO:1 as described herein.

"Patient," "subject," "patient in need thereof," and "subject in need thereof" are herein used interchangeably and refer to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

"Disease" or "condition" refer to a state of being or health status of a patient or subject capable of being treated with a compound, pharmaceutical composition, or method provided herein. Examples contemplated herein of diseases, disorders, or conditions include, but are not limited to, cancer, lung cancer, breast cancer, ovarian cancer, leukemia, lymphoma, melanoma, pancreatic cancer, sarcoma, bladder cancer, bone cancer, brain cancer, cervical cancer, colon cancer, esophageal cancer, gastric cancer, liver cancer, head and neck cancer, kidney cancer, myeloma, thyroid cancer, prostate cancer, metastatic cancer, or carcinoma. In some instances, "disease" or "condition" refers to cancer. In some further instances, "cancer" refers to human cancers and carcinomas, sarcomas, adenocarcinomas, lymphomas, leukemias, melanomas, etc., including solid and lymphoid cancers, kidney, breast, lung, bladder, colon, ovarian, prostate, pancreas, stomach, brain, head and neck, skin, uterine, testicular, glioma, esophagus, liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), and/or multiple myeloma. In embodiments, the disease is AML. The AML may be AML expressing FLT3-mutant kinase, or AML having increased signal transduction activity in pathways involving a FLT3, a STAT, STAT3, or STAT5).

As used herein, the term "cancer" refers to all types of cancer, neoplasm or malignant tumors found in mammals, including leukemia, lymphoma, carcinomas and sarcomas.

Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g., hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, or melanoma. Additional examples include, cancer of the thyroid, endocrine system, brain, breast, cervix, colon, head & neck, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia. In embodiments the leukemia is acute myelogenous leukemia (AML), chronic myelogenous leukemia (CML), or precursor B-cell or T-cell acute lymphoblastic Leukemia (ALL).

The terms "acute myelogenous leukemia," "acute myeloid leukemia," or "AML" are used interchangeably and refer to leukemia characterized by the rapid accumulation of a population (e.g. clonal population) of abnormal myeloid cells in the bone marrow. AML may also be characterized by an increase in myeloid blast cells, which have failed to mature into normal haematopoietic cells due to, for example, a block in differentiation. In certain AML subtypes, AML is characterized by mutations of the protein kinase FLT3, as described herein, including embodiments thereof. AML characterized by mutations of FLT3 are herein referred to as "FLT3-AML." FLT3-AML patients typically have increased relapse rates and reduced overall survival.

Thus an "acute myeloid leukemia expressing a FLT3-kinase" as used herein refers to an AML cancer characterized by the overexpression or abnormal expression of a FLT3-kinase or expression of an aberrant FLT3-kinase (e.g. a FLT3-mutant kinase). An "acute myeloid leukemia expressing FLT3-ITD mutant kinase" as used herein refers to an AML cancer characterized by the expression of a FLT3-mutant kinase as described herein, that has a ITD mutation as described herein.

"Chronic myelogenous leukemia" or "CML" refers to leukemia characterized by the slow progression of production of abnormal myeloblasts, red blood cells or platelets. CML may be characterized by the presence of cytogenetic abnormalities including, for example, the Philadelphia chromosome (e.g. a translocation between chromosome 9 and 22 designated as t(9;22)(q34;q11). Kurzrock R, et al. *Ann Intern Med* 138 (10), 819-30, 2003; Goldman J M, *N Engl J Med* 349 (15), 1451-64, 2003; Deininger M W, *Blood* 96 (10), 3343-56, 2000. CML may be further characterized by mutations of ABL1-kinase or BCR-ABL1 mutant kinase as described herein, including embodiments thereof.

"Acute lymphoblastic leukemia" or "ALL" refers to lymphoid leukemias characterized by over production of B or T cell lymphoblasts. The ALL may be precursor B-cell ALL. Precursor B-cell ALL may be characterized by the expression of cytoplasmic CD79a, CD19, HLA-DR or other B cell-associated antigens. In embodiments, B-cell ALL is characterized by including expression of mutant-FLT3-kinases as described herein. The ALL may or T-cell ALL. T-cell ALL may be characterized by the expression of T cell-associated antigens including, for example, cytoplasmic CD3, CD7, CD2 or CDS. In embodiments, the T-cell ALL is Early T-cell precursor ALL and is identified in a children. ALL may be further characterized by mutations of the protein kinase, FLT3, as described herein, including embodiments thereof.

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abernethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

The term "associated" or "associated with" in the context of a substance or substance activity or function associated with a disease means that the disease is caused by (in whole or in part), a symptom of the disease is caused by (in whole or in part) the substance or substance activity or function, or a side-effect of the compound (e.g. toxicity) is caused by (in whole or in part) the substance or substance activity or function.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components. For example, binding of a kinase with a compound as described herein may result in a change in one or more protein-protein interactions of the kinase, resulting in changes in cell growth, proliferation, or survival. Exemplary signaling pathways include but are not limited to STAT signaling, MAPK signaling, and AKT signaling.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation).

The compositions of the present invention can be delivered transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

Pharmaceutical compositions may include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule, and/or reducing, eliminating, or slowing the progression of disease symptoms.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. cancer, lung cancer, breast cancer, ovarian cancer, leukemia, melanoma, pancreatic cancer, or prostate cancer), kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds described herein can be used in combination with one another, with other active agents, or with adjunctive agents that may not be effective alone, but may contribute to the efficacy of the active agent.

In embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In embodiments, co-administration can be accomplished by co-formulation, i.e., preparing a single pharmaceutical composition including both active agents. In embodiments, the active agents can be formulated separately. In another embodiment, the active and/or adjunctive agents may be linked or conjugated to one another.

"Anti-cancer agent" is used in accordance with its plain ordinary meaning and refers to a composition (e.g. compound, drug, antagonist, inhibitor, modulator) having anti-neoplastic properties or the ability to inhibit the growth or proliferation of cells. In embodiments, an anti-cancer agent is a chemotherapeutic. In embodiments, an anti-cancer agent is an agent identified herein having utility in methods of treating cancer. In embodiments, an anti-cancer agent is an agent approved by the FDA or similar regulatory agency of a country other than the USA, for treating cancer.

Examples of anti-cancer agents include, but are not limited to, MEK (e.g. MEK1, MEK2, or MEK1 and MEK2) inhibitors (e.g. XL518, CI-1040, PD035901, selumetinib/ AZD6244, GSK1120212/ trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5- azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (GLEEVEC®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. TAXOL™ (i.e. paclitaxel), TAXOTERE™ compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e.

desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (IRESSA™), erlotinib (TARCEVA™), cetuximab (ERBITUX™), lapatinib (TYKERB™), panitumumab (VECTIBIX™), vandetanib (CAPRELSA™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

I. COMPOSITIONS

Provided herein compositions having the formula:

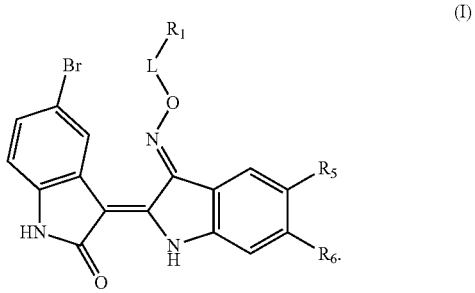

(I)

In the compound of formula (I), L is a bond, substituted or unsubstituted alkylene, or substituted or unsubstituted heteroalkylene. $R^1$ is hydrogen, halogen, —$CF_3$, —$CCl_3$, —$CBr_3$, —$CI_3$, —$OCF_3$, —$OCCl_3$, —$OCBr_3$, —$OCI_3$, —CN, —OH, —$NH_2$, —COOH, —C(O)$OR^4$, —$CONH_2$, —$NO_2$, —SH, —$NHNH_2$, —$NR^2R^3$, —$OR^4$, —$SR^4$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^2$ and $R^3$ are independently substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or $R^2$ and $R^3$ are optionally joined together to form a substituted or unsubstituted heterocycloalkyl or substituted or unsubstituted heteroaryl. $R^4$ is substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^5$ and $R^6$ are independently hydrogen, halogen, —$CF_3$, —$CCl_3$, —$CBr_3$, —$CI_3$, —$OCF_3$, —$OCCl_3$, —$OCBr_3$, —$OCI_3$, —CN, —OH, —$NH_2$, —COOH, —C(O)$OR^9$, —$CONH_2$, —$NO_2$, —SH, —$NHNH_2$, —$NR^7R^8$, —$OR^9$, —$SR^9$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^7$ and $R^8$ are independently substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, or $R^7$ and $R^8$ are optionally joined together to form a substituted or unsubstituted heterocycloalkyl or substituted or unsubstituted heteroaryl. $R^9$ is substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

L may be a bond or substituted or unsubstituted alkylene. In embodiments, L is substituted or unsubstituted alkylene. L may be unsubstituted alkylene. L may be unsubstituted $C_1$-$C_8$ alkylene. L may be unsubstituted $C_1$-$C_4$ alkylene. L may be unsubstituted $C_2$ alkylene. L may be unsubstituted methylene. In embodiments, L is a bond. In embodiments, L is independently a bond or $R^{47}$-substituted or unsubstituted alkylene. L may be substituted or unsubstituted heteroalkylene. L may be substituted or unsubstituted 2 to 8 membered heteroalkylene. L may be substituted or unsubstituted 2 to 6 membered heteroalkylene. L may be unsubstituted heteroalkylene. L may be unsubstituted 2 to 8 membered heteroalkylene. L may be unsubstituted 2 to 6 membered heteroalkylene.

$R^{47}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{48}$-substituted or unsubstituted alkyl, $R^{48}$-substituted or unsubstituted heteroalkyl, $R^{48}$-substituted or unsubstituted cycloalkyl, $R^{48}$-substituted or unsubstituted heterocycloalkyl, $R^{48}$-substituted or unsubstituted aryl, or $R^{48}$-substituted or unsubstituted heteroaryl.

$R^{48}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{49}$-substituted or unsubstituted alkyl, $R^{49}$-substituted or unsubstituted heteroalkyl, $R^{49}$-substituted or unsubstituted cycloalkyl, $R^{49}$-substituted or unsubstituted heterocycloalkyl, $R^{49}$-substituted or unsubstituted aryl, or $R^{49}$-substituted or unsubstituted heteroaryl.

In embodiments, $R^1$ is halogen, —$CF_3$, —$CCl_3$, —$CBr_3$, —$CI_3$, —$OCF_3$, —$OCCl_3$, —$OCBr_3$, —$OCI_3$, —CN, —OH, —$NH_2$, —COOH, —C(O)$OR^4$, —$CONH_2$, —$NO_2$, —SH, —$NHNH_2$, —$NR^2R^3$, —$OR^4$, —$SR^4$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, $R^1$ is —$NR^2R^3$. In embodiments, $R^1$ is substituted alkyl. $R^1$ may be substituted $C_1$-$C_8$ alkyl. In embodiments, $R^1$ is substituted $C_1$-$C_4$ alkyl. $R^1$ may be substituted ethyl. In embodiments, $R^1$ is a substituted methyl. In embodiments, $R^1$ is not hydrogen. In embodiments, $R^1$ is not —OH. In embodiments, $R^1$ is not —$NH_2$.

In embodiments, $R^1$ is independently hydrogen, halogen, —$CF_3$, —CN, —OH, —$NH_2$, —COOH, —$CONH_2$, —$NO_2$, —SH, —$NHNH_2$, —$OCF_3$, —$OCHF_2$, $R^{20}$-substituted or unsubstituted alkyl, $R^{20}$-substituted or unsubstituted heteroalkyl, $R^{20}$-substituted or unsubstituted cycloalkyl, $R^{20}$-substituted or unsubstituted heterocycloalkyl, $R^{20}$-substituted or unsubstituted aryl, or $R^{20}$-substituted or unsubstituted heteroaryl.

In embodiments, $R^1$ is independently halogen, —$CF_3$, —CN, —OH, —$NH_2$, —COOH, —$CONH_2$, —$NO_2$, —SH, —$NHNH_2$, —$OCF_3$, —$OCHF_2$, $R^{20}$-substituted or unsubstituted alkyl, $R^{20}$-substituted or unsubstituted heteroalkyl, $R^{20}$-substituted or unsubstituted cycloalkyl, $R^{20}$-substituted or unsubstituted heterocycloalkyl, $R^{20}$-substituted or unsubstituted aryl, or $R^{20}$-substituted or unsubstituted heteroaryl.

In embodiments, $R^1$ is substituted or unsubstituted $C_1$-$C_{20}$ alkyl. $R^1$ may be $R^{20}$-substituted or unsubstituted $C_1$-$C_{20}$ alkyl. $R^1$ may be substituted or unsubstituted $C_1$-$C_{10}$ alkyl. $R^1$ may be $R^{20}$-substituted or unsubstituted $C_1$-$C_{10}$ alkyl. $R^1$ may be substituted or unsubstituted $C_1$-$C_8$ alkyl. $R^1$ may be $R^{20}$-substituted or unsubstituted $C_1$-$C_8$ alkyl. $R^1$ may be $R^{20}$-substituted or unsubstituted $C_1$-$C_5$ alkyl. $R^1$ may be $R^{20}$-substituted or unsubstituted $C_1$-$C_5$ alkyl.

In embodiments, $R^1$ is substituted or unsubstituted 2 to 20 membered heteroalkyl. $R^1$ may be $R^{20}$-substituted or unsubstituted 2 to 20 membered heteroalkyl. $R^1$ may be substituted or unsubstituted 2 to 10 membered heteroalkyl. $R^1$ may be $R^{20}$-substituted or unsubstituted 2 to 10 membered heteroalkyl. $R^1$ may be substituted or unsubstituted 2 to 8 membered heteroalkyl. $R^1$ may be $R^{20}$-substituted or unsubstituted 2 to 8 membered heteroalkyl. $R^1$ may be substituted or unsubstituted 2 to 6 membered heteroalkyl. $R^1$ may be $R^{20}$-substituted or unsubstituted 2 to 6 membered heteroalkyl.

In embodiments, $R^1$ is substituted or unsubstituted 3 to 20 membered cycloalkyl. $R^1$ may be $R^{20}$-substituted or unsubstituted 3 to 20 membered cycloalkyl. $R^1$ may be substituted or unsubstituted 3 to 10 membered cycloalkyl. $R^1$ may be $R^{20}$-substituted or unsubstituted 3 to 10 membered cycloalkyl. $R^1$ may be substituted or unsubstituted 3 to 8 membered cycloalkyl. $R^1$ may be $R^{20}$-substituted or unsubstituted 3 to 8 membered cycloalkyl. $R^1$ may be substituted or unsubstituted 3 to 6 membered cycloalkyl. $R^1$ may be $R^{20}$-substituted or unsubstituted 3 to 6 membered cycloalkyl. $R^1$ may be substituted or unsubstituted 5 membered cycloalkyl. $R^1$ may be $R^{20}$-substituted or unsubstituted 5 membered cycloalkyl. $R^1$ may be substituted or unsubstituted 6 membered cycloalkyl. $R^1$ may be $R^{20}$-substituted or unsubstituted 6 membered cycloalkyl.

In embodiments, $R^1$ is substituted or unsubstituted 3 to 20 membered heterocycloalkyl. $R^1$ may be $R^{20}$-substituted or unsubstituted 3 to 20 membered heterocycloalkyl. $R^1$ may be substituted or unsubstituted 3 to 10 membered heterocycloalkyl. $R^1$ may be $R^{20}$-substituted or unsubstituted 3 to 10 membered heterocycloalkyl. $R^1$ may be substituted or unsubstituted 3 to 8 membered heterocycloalkyl. $R^1$ may be $R^{20}$-substituted or unsubstituted 3 to 8 membered heterocycloalkyl. $R^1$ may be substituted or unsubstituted 3 to 6 membered heterocycloalkyl. $R^1$ may be $R^{20}$-substituted or unsubstituted 3 to 6 membered heterocycloalkyl. $R^1$ may be substituted or unsubstituted 5 membered heterocycloalkyl. $R^1$ may be $R^{20}$-substituted or unsubstituted 5 membered heterocycloalkyl. $R^1$ may be substituted or unsubstituted 6 membered heterocycloalkyl. $R^1$ may be $R^{20}$-substituted or unsubstituted 6 membered heterocycloalkyl.

In embodiments, $R^1$ is substituted or unsubstituted 5 to 10 membered aryl. $R^1$ may be $R^{20}$-substituted or unsubstituted 5 to 10 membered aryl. $R^1$ may be substituted or unsubstituted 5 to 8 membered aryl. $R^1$ may be $R^{20}$-substituted or unsubstituted 5 to 8 membered aryl. $R^1$ may be substituted or unsubstituted 6 membered aryl. $R^1$ may be $R^{20}$-substituted or unsubstituted 6 membered aryl.

In embodiments, $R^1$ is substituted or unsubstituted 5 to 10 membered heteroaryl. $R^1$ may be $R^{20}$-substituted or unsubstituted 5 to 10 membered heteroaryl. $R^1$ may be substituted or unsubstituted 5 to 8 membered heteroaryl. $R^1$ may be $R^{20}$-substituted or unsubstituted 5 to 8 membered heteroaryl. $R^1$ may be substituted or unsubstituted 6 membered heteroaryl. $R^1$ may be $R^{20}$-substituted or unsubstituted 6 membered heteroaryl.

$R^{20}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{21}$-substituted or unsubstituted alkyl, $R^{21}$-substituted or unsubstituted heteroalkyl, $R^{21}$-substituted or unsubstituted cycloalkyl, $R^{21}$-substituted or unsubstituted heterocycloalkyl, $R^{21}$-substituted or unsubstituted aryl, or $R^{21}$-substituted or unsubstituted heteroaryl.

$R^{21}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCHF$_2$, $R^{22}$-substituted or unsubstituted alkyl, $R^{22}$-substituted or unsubstituted heteroalkyl, $R^{22}$-substituted or unsubstituted cycloalkyl, $R^{22}$-substituted or unsubstituted heterocycloalkyl, $R^{22}$-substituted or unsubstituted aryl, or $R^{22}$-substituted or unsubstituted heteroaryl.

In embodiments, $R^2$ is independently substituted or unsubstituted alkyl. $R^2$ may independently be substituted or unsubstituted $C_1$-$C_8$ alkyl. $R^2$ may independently be substituted $C_1$-$C_8$ alkyl. $R^2$ may independently be unsubstituted $C_1$-$C_8$ alkyl. $R^2$ may independently be substituted or unsubstituted $C_1$-$C_4$ alkyl. $R^2$ may independently be substituted $C_1$-$C_4$ alkyl. $R^2$ may independently be unsubstituted $C_1$-$C_4$ alkyl. $R^2$ may independently be —OH substituted or unsubstituted $C_1$-$C_4$ alkyl. $R^2$ may independently be substituted or unsubstituted methyl. $R^2$ may independently be substituted or unsubstituted ethyl. $R^2$ may independently be substituted or unsubstituted propyl. In embodiments, $R^2$ is independently $R^{23}$-substituted or unsubstituted alkyl, $R^{23}$-substituted or unsubstituted heteroalkyl, $R^{23}$-substituted or unsubstituted cycloalkyl, $R^{23}$-substituted or unsubstituted heterocycloalkyl, $R^{23}$-substituted or unsubstituted aryl, or $R^{23}$-substituted or unsubstituted heteroaryl.

In embodiments, $R^2$ is substituted or unsubstituted $C_1$-$C_{20}$ alkyl. $R^2$ may be $R^{23}$-substituted or unsubstituted $C_1$-$C_{20}$ alkyl. $R^2$ may be substituted or unsubstituted $C_1$-$C_{10}$ alkyl. $R^2$ may be $R^{23}$-substituted or unsubstituted $C_1$-$C_{10}$ alkyl. $R^2$ may be substituted or unsubstituted $C_1$-$C_8$ alkyl. $R^2$ may be $R^{23}$-substituted or unsubstituted $C_1$-$C_8$ alkyl. $R^2$ may be substituted or unsubstituted $C_1$-$C_5$ alkyl. $R^2$ may be $R^{23}$-substituted or unsubstituted $C_1$-$C_5$ alkyl.

In embodiments, $R^2$ is substituted or unsubstituted 2 to 20 membered heteroalkyl. $R^2$ may be $R^{23}$-substituted or unsubstituted 2 to 20 membered heteroalkyl. $R^2$ may be substituted or unsubstituted 2 to 10 membered heteroalkyl. $R^2$ may be $R^{23}$-substituted or unsubstituted 2 to 10 membered heteroalkyl. $R^2$ may be substituted or unsubstituted 2 to 8 membered heteroalkyl. $R^2$ may be $R^{23}$-substituted or unsubstituted 2 to 8 membered heteroalkyl. $R^2$ may be substituted or unsubstituted 2 to 6 membered heteroalkyl. $R^2$ may be $R^{23}$-substituted or unsubstituted 2 to 6 membered heteroalkyl.

In embodiments, $R^2$ is substituted or unsubstituted 3 to 20 membered cycloalkyl. $R^2$ may be $R^{23}$-substituted or unsubstituted 3 to 20 membered cycloalkyl. $R^2$ may be substituted or unsubstituted 3 to 10 membered cycloalkyl. $R^2$ may be $R^{23}$-substituted or unsubstituted 3 to 10 membered cycloalkyl. $R^2$ may be substituted or unsubstituted 3 to 8 membered cycloalkyl. $R^2$ may be $R^{23}$-substituted or unsubstituted 3 to 8 membered cycloalkyl. $R^2$ may be substituted or unsubstituted 3 to 6 membered cycloalkyl. $R^2$ may be $R^{23}$-substituted or unsubstituted 3 to 6 membered cycloalkyl. $R^2$ may be substituted or unsubstituted 5 membered cycloalkyl. $R^2$ may be $R^{23}$-substituted or unsubstituted 5 membered cycloalkyl. $R^2$ may be substituted or unsubstituted 6 membered cycloalkyl. $R^2$ may be $R^{23}$-substituted or unsubstituted 6 membered cycloalkyl.

In embodiments, $R^2$ is substituted or unsubstituted 3 to 20 membered heterocycloalkyl. $R^2$ may be $R^{23}$-substituted or unsubstituted 3 to 20 membered heterocycloalkyl. $R^2$ may be substituted or unsubstituted 3 to 10 membered heterocycloalkyl. $R^2$ may be $R^{23}$-substituted or unsubstituted 3 to 10 membered heterocycloalkyl. $R^2$ may be substituted or unsubstituted 3 to 8 membered heterocycloalkyl. $R^2$ may be $R^{23}$-substituted or unsubstituted 3 to 8 membered heterocycloalkyl. $R^2$ may be substituted or unsubstituted 3 to 6 membered heterocycloalkyl. $R^2$ may be $R^{23}$-substituted or unsubstituted 3 to 6 membered heterocycloalkyl. $R^2$ may be substituted or unsubstituted 5 membered heterocycloalkyl. $R^2$ may be $R^{23}$-substituted or unsubstituted 5 membered heterocycloalkyl. $R^2$ may be substituted or unsubstituted 6 membered heterocycloalkyl. $R^2$ may be $R^{23}$-substituted or unsubstituted 6 membered heterocycloalkyl.

In embodiments, $R^2$ is substituted or unsubstituted 5 to 10 membered aryl. $R^2$ may be $R^{23}$-substituted or unsubstituted 5 to 10 membered aryl. $R^2$ may be substituted or unsubstituted 5 to 8 membered aryl. $R^2$ may be $R^{23}$-substituted or unsubstituted 5 to 8 membered aryl. $R^2$ may be substituted or unsubstituted 6 membered aryl. $R^2$ may be $R^{23}$-substituted or unsubstituted 6 membered aryl.

In embodiments, $R^2$ is substituted or unsubstituted 5 to 10 membered heteroaryl. $R^2$ may be $R^{23}$-substituted or unsubstituted 5 to 10 membered heteroaryl. $R^2$ may be substituted or unsubstituted 5 to 8 membered heteroaryl. $R^2$ may be $R^{23}$-substituted or unsubstituted 5 to 8 membered heteroaryl. $R^2$ may be substituted or unsubstituted 6 membered heteroaryl. $R^2$ may be $R^{23}$-substituted or unsubstituted 6 membered heteroaryl.

$R^{23}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCHF$_2$, $R^{24}$-substituted or unsubstituted alkyl, $R^{24}$-substituted or unsubstituted heteroalkyl, $R^{24}$-substituted or unsubstituted cycloalkyl, $R^{24}$-substituted or unsubstituted heterocycloalkyl, $R^{24}$-substituted or unsubstituted aryl, or $R^{24}$-substituted or unsubstituted heteroaryl. $R^{23}$ may independently be —OH. $R^{23}$ may independently be unsubstituted methyl. $R^{23}$ may independently be $R^{24}$-substituted or unsubstituted heteroalkyl. $R^{23}$ may independently be $R^{24}$-substituted or unsubstituted alkyl. $R^{23}$ may independently be $R^{24}$-substituted or unsubstituted $C_1$-$C_4$ alkyl.

$R^{24}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCHF$_2$, $R^{25}$-substituted or unsubstituted alkyl, $R^{25}$-substituted or unsubstituted heteroalkyl, $R^{25}$-substituted or unsubstituted cycloalkyl, $R^{25}$-substituted or unsubstituted heterocycloalkyl, $R^{25}$-substituted or unsubstituted aryl, or $R^{25}$-substituted or unsubstituted heteroaryl. $R^{24}$ may independently be —OH.

In embodiments, $R^3$ is independently substituted or unsubstituted alkyl. $R^3$ may independently be substituted or unsubstituted $C_1$-$C_8$ alkyl. $R^3$ may independently be substituted $C_1$-$C_8$ alkyl. $R^3$ may independently be unsubstituted $C_1$-$C_8$ alkyl. $R^3$ may independently be substituted or unsubstituted $C_1$-$C_4$ alkyl. $R^3$ may independently be substituted $C_1$-$C_4$ alkyl. $R^3$ may independently be unsubstituted $C_1$-$C_4$ alkyl. $R^3$ may independently be —OH substituted or unsubstituted $C_1$-$C_4$ alkyl. $R^3$ may independently be substituted or unsubstituted methyl. $R^3$ may independently be substituted or unsubstituted ethyl. $R^3$ may independently be substituted or unsubstituted propyl. In embodiments, $R^3$ is independently $R^{26}$-substituted or unsubstituted alkyl, $R^{26}$-substituted or unsubstituted heteroalkyl, $R^{26}$-substituted or unsubstituted cycloalkyl, $R^{26}$-substituted or unsubstituted heterocycloalkyl, $R^{26}$-substituted or unsubstituted aryl, or $R^{26}$-substituted or unsubstituted heteroaryl.

In embodiments, $R^3$ is substituted or unsubstituted $C_1$-$C_{20}$ alkyl. $R^3$ may be $R^{26}$-substituted or unsubstituted $C_1$-$C_{20}$ alkyl. $R^3$ may be substituted or unsubstituted $C_1$-$C_{10}$ alkyl. $R^3$ may be $R^{26}$-substituted or unsubstituted $C_1$-$C_{10}$ alkyl. $R^3$ may be substituted or unsubstituted $C_1$-$C_8$ alkyl. $R^3$ may be $R^{26}$-substituted or unsubstituted $C_1$-$C_8$ alkyl. $R^3$ may be substituted or unsubstituted $C_1$-$C_5$ alkyl. $R^3$ may be $R^{26}$-substituted or unsubstituted $C_1$-$C_5$ alkyl.

In embodiments, $R^3$ is substituted or unsubstituted 2 to 20 membered heteroalkyl. $R^3$ may be $R^{26}$-substituted or unsubstituted 2 to 20 membered heteroalkyl. $R^3$ may be substituted or unsubstituted 2 to 10 membered heteroalkyl. $R^3$ may be $R^{26}$-substituted or unsubstituted 2 to 10 membered heteroalkyl. $R^3$ may be substituted or unsubstituted 2 to 8 membered heteroalkyl. $R^3$ may be $R^{26}$-substituted or unsubstituted 2 to 8 membered heteroalkyl. $R^3$ may be substituted or unsubstituted 2 to 6 membered heteroalkyl. $R^3$ may be $R^{26}$-substituted or unsubstituted 2 to 6 membered heteroalkyl.

In embodiments, $R^3$ is substituted or unsubstituted 3 to 20 membered cycloalkyl. $R^3$ may be $R^{26}$-substituted or unsubstituted 3 to 20 membered cycloalkyl. $R^3$ may be substituted or unsubstituted 3 to 10 membered cycloalkyl. $R^3$ may be $R^{26}$-substituted or unsubstituted 3 to 10 membered cycloalkyl. $R^3$ may be substituted or unsubstituted 3 to 8 membered cycloalkyl. $R^3$ may be $R^{26}$-substituted or unsubstituted 3 to 8 membered cycloalkyl. $R^3$ may be substituted or unsubstituted 3 to 6 membered cycloalkyl. $R^3$ may be $R^{26}$-substituted or unsubstituted 3 to 6 membered cycloalkyl. $R^3$ may be substituted or unsubstituted 5 membered cycloalkyl. $R^3$ may be $R^{26}$-substituted or unsubstituted 5 membered cycloalkyl. $R^3$ may be substituted or unsubstituted 6 membered cycloalkyl. $R^3$ may be $R^{26}$-substituted or unsubstituted 6 membered cycloalkyl.

In embodiments, $R^3$ is substituted or unsubstituted 3 to 20 membered heterocycloalkyl. $R^3$ may be $R^{26}$-substituted or unsubstituted 3 to 20 membered heterocycloalkyl. $R^3$ may be substituted or unsubstituted 3 to 10 membered heterocycloalkyl. $R^3$ may be $R^{26}$-substituted or unsubstituted 3 to 10 membered heterocycloalkyl. $R^3$ may be substituted or unsubstituted 3 to 8 membered heterocycloalkyl. $R^3$ may be $R^{26}$-substituted or unsubstituted 3 to 8 membered heterocycloalkyl. $R^3$ may be substituted or unsubstituted 3 to 6 membered heterocycloalkyl. $R^3$ may be $R^{26}$-substituted or unsubstituted 3 to 6 membered heterocycloalkyl. $R^3$ may be substituted or unsubstituted 5 membered heterocycloalkyl. $R^3$ may be $R^{26}$-substituted or unsubstituted 5 membered heterocycloalkyl. $R^3$ may be substituted or unsubstituted 6 membered heterocycloalkyl. $R^3$ may be $R^{26}$-substituted or unsubstituted 6 membered heterocycloalkyl.

In embodiments, $R^3$ is substituted or unsubstituted 5 to 10 membered aryl. $R^3$ may be $R^{26}$-substituted or unsubstituted 5 to 10 membered aryl. $R^3$ may be substituted or unsubstituted 5 to 8 membered aryl. $R^3$ may be $R^{26}$-substituted or unsubstituted 5 to 8 membered aryl. $R^3$ may be substituted or unsubstituted 6 membered aryl. $R^3$ may be $R^{26}$-substituted or unsubstituted 6 membered aryl.

In embodiments, $R^3$ is substituted or unsubstituted 5 to 10 membered heteroaryl. $R^3$ may be $R^{26}$-substituted or unsubstituted 5 to 10 membered heteroaryl. $R^3$ may be substituted or unsubstituted 5 to 8 membered heteroaryl. $R^3$ may be $R^{26}$-substituted or unsubstituted 5 to 8 membered heteroaryl. $R^3$ may be substituted or unsubstituted 6 membered heteroaryl. $R^3$ may be $R^{26}$-substituted or unsubstituted 6 membered heteroaryl.

$R^{26}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{27}$-substituted or unsubstituted alkyl, $R^{27}$-substituted or unsubstituted heteroalkyl, $R^{27}$-substituted or unsubstituted cycloalkyl, $R^{27}$-substituted or unsubstituted heterocycloalkyl, $R^{27}$-substituted or unsubstituted aryl, or $R^{27}$-substituted or unsubstituted heteroaryl. $R^{26}$ may independently be —OH. $R^{26}$ may independently be unsubstituted methyl. $R^{23}$ may independently be $R^{24}$-substituted or unsubstituted heteroalkyl. $R^{26}$ may independently be $R^{27}$-substituted or unsubstituted alkyl. $R^{26}$ may independently be $R^{27}$-substituted or unsubstituted $C_1$-$C_4$ alkyl.

$R^{27}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{28}$-substituted or unsubstituted alkyl, $R^{28}$-substituted or unsubstituted heteroalkyl, $R^{28}$-substituted or unsubstituted cycloalkyl, $R^{28}$-substituted or unsubstituted heterocycloalkyl, $R^{28}$-substituted or unsubstituted aryl, or $R^{28}$-substituted or unsubstituted heteroaryl. $R^{27}$ may independently be —OH.

In embodiments, $R^2$ and $R^3$ are joined together to form a substituted or unsubstituted heterocycloalkyl or substituted or unsubstituted heteroaryl. $R^2$ and $R^3$ may be joined together to form a substituted or unsubstituted heterocycloalkyl. $R^2$ and $R^3$ may be joined together to form a substituted or unsubstituted 3 to 8 membered heterocycloalkyl. $R^2$ and $R^3$ may be joined together to form a substituted 3 to 8 membered heterocycloalkyl. $R^2$ and $R^3$ may be joined together to form a substituted or unsubstituted 5 to 7 membered heterocycloalkyl. $R^2$ and $R^3$ may be joined together to form a substituted 5 to 7 membered heterocycloalkyl. $R^2$ and $R^3$ may be joined together to form a substituted or unsubstituted 4 membered heterocycloalkyl. $R^2$ and $R^3$ may be joined together to form a substituted or unsubstituted 5 membered heterocycloalkyl. $R^2$ and $R^3$ may be joined together to form a substituted or unsubstituted 6 membered heterocycloalkyl.

$R^2$ and $R^3$ may be joined together to form a $R^{23}$-substituted or unsubstituted 5 to 7 membered heterocycloalkyl. $R^2$ and $R^3$ may be joined together to form a $R^{23}$-substituted or unsubstituted 4 membered heterocycloalkyl. $R^2$ and $R^3$ may be joined together to form an $R^{23}$-substituted or unsubstituted 5 to 7 membered heterocycloalkyl, wherein $R^{23}$ is independently a substituted or unsubstituted alkyl or substituted or unsubstituted heteroalkyl. $R^2$ and $R^3$ may be joined together to form an $R^{23}$-substituted 5 to 7 membered heterocycloalkyl, wherein $R^{23}$ is independently a substituted or unsubstituted $C_1$-$C_8$ alkyl or substituted or unsubstituted 2 to 8 membered heteroalkyl.

In embodiments, $R^2$ and $R^3$ are joined together to form a substituted or unsubstituted pyrrolidinyl. In embodiments, $R^2$ and $R^3$ are joined together to form a substituted or unsubstituted piperazinyl. In embodiments, $R^2$ and $R^3$ are joined together to form a $R^{23}$-substituted or unsubstituted pyrrolidinyl. In embodiments, $R^2$ and $R^3$ are joined together to form a $R^{23}$-substituted or unsubstituted piperazinyl. $R^{23}$ is as described herein, including embodiments thereof In embodiments, $R^4$ is independently $R^{29}$-substituted or unsubstituted alkyl, $R^{29}$-substituted or unsubstituted heteroalkyl, $R^{29}$-substituted or unsubstituted cycloalkyl, $R^{29}$- substituted or unsubstituted heterocycloalkyl, $R^{29}$-substituted or unsubstituted aryl, or $R^{29}$-substituted or unsubstituted heteroaryl.

$R^{29}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{30}$-substituted or unsubstituted alkyl, $R^{30}$-substituted or unsubstituted heteroalkyl, $R^{30}$-substituted or unsubstituted cycloalkyl, $R^{30}$-substituted or unsubstituted heterocycloalkyl, $R^{30}$-substituted or unsubstituted aryl, or $R^{30}$-substituted or unsubstituted heteroaryl.

$R^{30}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{31}$-substituted or unsubstituted alkyl, $R^{31}$-substituted or unsubstituted heteroalkyl, $R^{31}$-substituted or unsubstituted cycloalkyl, $R^{31}$-substituted or unsubstituted heterocycloalkyl, $R^{31}$-substituted or unsubstituted aryl, or $R^{31}$-substituted or unsubstituted heteroaryl.

$R^5$ may independently be halogen, —$CF_3$, —$CCl_3$, —$CBr_3$, —$CI_3$, —$OCF_3$, —$OCCl_3$, —$OCBr_3$, —$OCI_3$, —CN, —OH, —$NH_2$, —COOH, —C(O)$OR^9$, —$CONH_2$, —$NO_2$, —SH, —$NHNH_2$, —$NR^7R^8$, —$OR^9$, —$SR^9$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, $R^5$ is independently —F. In embodiments, $R^5$ is independently —Cl. In embodiments, $R^5$ is independently —I. In embodiments, $R^5$ is independently —Br. In embodiments, $R^5$ is —$NR^7R^8$.

In embodiments, $R^5$ is —C(O)$OCH_3$. In embodiments, $R^5$ is —$OCH_3$. In embodiments, $R^5$ is —$OCH(CH_3)_2$. In embodiments, $R^5$ is —CN. In embodiments, $R^5$ is —$NO_2$. In embodiments, $R^5$ is —$NH_2$. In embodiments, $R^5$ is halogen. In embodiments, $R^5$ is independently hydrogen. In embodiments, $R^5$ is independently unsubstituted methyl. In embodiments, $R^5$ is independently —$OCF_3$. In embodiments, $R^5$ is independently —NHAc. In embodiments, $R^5$ is independently —OH. In embodiments, $R^5$ is unsubstituted alkyl. $R^5$ may be unsubstituted $C_1$-$C_8$ alkyl. In embodiments, $R^5$ is unsubstituted $C_1$-$C_4$ alkyl. $R^5$ may be unsubstituted ethyl. In embodiments, $R^5$ is an unsubstituted methyl. In embodiments, $R^5$ is independently hydrogen, halogen, —$CF_3$, —CN, —OH, —$NH_2$, —COOH, —$CONH_2$, —$NO_2$, —SH, —$NHNH_2$, —$OCF_3$, —$OCHF_2$, $R^{32}$-substituted or unsubstituted alkyl, $R^{32}$-substituted or unsubstituted heteroalkyl, $R^{32}$-substituted or unsubstituted cycloalkyl, $R^{32}$-substituted or unsubstituted heterocycloalkyl, $R^{32}$-substituted or unsubstituted aryl, or $R^{32}$-substituted or unsubstituted heteroaryl. In embodiments, $R^5$ is independently halogen, —$CF_3$, —CN, —OH, —$NH_2$, —SH, —COOH, —$CONH_2$, —$NO_2$, —SH, —$NHNH_2$, —$OCF_3$, —$OCHF_2$, $R^{32}$-substituted or unsubstituted alkyl, R32-substituted or unsubstituted heteroalkyl, $R^{32}$-substituted or unsubstituted cycloalkyl, $R^{32}$-substituted or unsubstituted heterocycloalkyl, $R^{32}$-substituted or unsubstituted aryl, or $R^{32}$-substituted or unsubstituted heteroaryl. In embodiments $R^5$ is not hydrogen.

Each $R^{32}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{33}$-substituted or unsubstituted alkyl, $R^{33}$-substituted or unsubstituted heteroalkyl, $R^{33}$-substituted or unsubstituted cycloalkyl, $R^{33}$-substituted or unsubstituted heterocycloalkyl, $R^{33}$-substituted or unsubstituted aryl, or $R^{33}$-substituted or unsubstituted heteroaryl.

Each $R^{33}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{34}$-substituted or unsubstituted alkyl, $R^{34}$-substituted or unsubstituted heteroalkyl, $R^{34}$-substituted or unsubstituted cycloalkyl, $R^{34}$-substituted or unsubstituted heterocycloalkyl, $R^{34}$-substituted or unsubstituted aryl, or $R^{34}$-substituted or unsubstituted heteroaryl.

$R^6$ may independently be halogen, —$CF_3$, —$CCl_3$, —$CBr_3$, —$CI_3$, —$OCF_3$, —$OCCl_3$, —$OCBr_3$, —$OCI_3$, —CN, —OH, —$NH_2$, —COOH, —C(O)$OR^9$, —$CONH_2$, —$NO_2$, —SH, —$NHNH_2$, —$NR^7R^8$, —$OR^9$, —$SR^9$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, $R^6$ is independently —F. In embodiments, $R^6$ is independently —Cl. In embodiments, $R^6$ is independently —I. In embodiments, $R^6$ is independently —Br. In embodiments, $R^6$ is —$NR^7R^8$.

In embodiments, $R^6$ is —C(O)$OCH_3$. In embodiments, $R^6$ is —$OCH_3$. In embodiments, $R^6$ is —$OCH(CH_3)_2$. In embodiments, $R^6$ is —CN. In embodiments, $R^6$ is —$NO_2$. In embodiments, $R^6$ is —$NH_2$. In embodiments, $R^6$ is halogen. In embodiments, $R^6$ is independently hydrogen. In embodiments, $R^6$ is independently unsubstituted methyl. In embodiments, $R^6$ is independently —$OCF_3$. In embodiments, $R^6$ is independently —NHAc. In embodiments, $R^6$ is independently —OH. In embodiments, $R^6$ is unsubstituted alkyl. $R^6$ may be unsubstituted $C_1$-$C_8$ alkyl. In embodiments, $R^6$ is unsubstituted $C_1$-$C_4$ alkyl. $R^6$ may be unsubstituted ethyl. In embodiments, $R^6$ is an unsubstituted methyl. In embodiments, $R^6$ is independently hydrogen, halogen, —$CF_3$, —CN, —OH, —$NH_2$, —COOH, —$CONH_2$, —$NO_2$, —SH, —$NHNH_2$, —$OCF_3$, —$OCHF_2$, $R^{35}$-substituted or unsubstituted alkyl, $R^{35}$-substituted or unsubstituted heteroalkyl, $R^{35}$-substituted or unsubstituted cycloalkyl, $R^{35}$-substituted or unsubstituted heterocycloalkyl, $R^{35}$-substituted or unsubstituted aryl, or $R^{35}$-substituted or unsubstituted heteroaryl. In embodiments, $R^6$ is independently halogen, —$CF_3$, —CN, —OH, —$NH_2$, —COOH, —$CONH_2$, —$NO_2$, —SH, —$NHNH_2$, —$OCF_3$, —$OCHF_2$, $R^{35}$-substituted or unsubstituted alkyl, $R^{35}$-substituted or unsubstituted heteroalkyl, $R^{35}$-substituted or unsubstituted cycloalkyl, $R^{35}$-substituted or unsubstituted heterocycloalkyl, $R^{35}$-substituted or unsubstituted aryl, or $R^{35}$-substituted or unsubstituted heteroaryl. In embodiments, $R^5$ and $R^6$ are independently hydrogen. In embodiments, $R^6$ is not hydrogen.

Each $R^{35}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{36}$-substituted or unsubstituted alkyl, $R^{36}$-substituted or unsubstituted heteroalkyl, $R^{36}$-substituted or unsubstituted cycloalkyl, $R^{36}$-substituted or unsubstituted heterocycloalkyl, $R^{36}$-substituted or unsubstituted aryl, or $R^{36}$-substituted or unsubstituted heteroaryl.

Each $R^{36}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCHF_2$, $R^{37}$-substituted or unsubstituted alkyl, $R^{37}$-substituted or unsubstituted heteroalkyl, $R^{37}$-substituted or unsubstituted cycloalkyl, $R^{37}$-substituted or unsubstituted heterocycloalkyl, $R^{37}$-substituted or unsubstituted aryl, or $R^{37}$-substituted or unsubstituted heteroaryl.

In embodiments, $R^7$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCHF_2$, $R^{38}$-substituted or unsubstituted alkyl, $R^{38}$-substituted or unsubstituted heteroalkyl, $R^{38}$-substituted or unsubstituted cycloalkyl, $R^{38}$-substituted or unsubstituted heterocycloalkyl, $R^{38}$-substituted or unsubstituted aryl, or $R^{38}$-substituted or unsubstituted heteroaryl.

$R^{38}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCHF_2$, —$S(O)_2CHCH_2$, —$NHS(O)_2CHCH_2$, $R^{39}$-substituted or unsubstituted alkyl, $R^{39}$-substituted or unsubstituted heteroalkyl, $R^{39}$-substituted or unsubstituted cycloalkyl, $R^{39}$-substituted or unsubstituted heterocycloalkyl, $R^{39}$-substituted or unsubstituted aryl, or $R^{39}$-substituted or unsubstituted heteroaryl. $R^{38}$ may independently be —OH. $R^{38}$ may independently be unsubstituted methyl. $R^{38}$ may independently be $R^{39}$-substituted or unsubstituted heteroalkyl. $R^{38}$ may independently be $R^{39}$-substituted or unsubstituted alkyl. $R^{38}$ may independently be $R^{39}$-substituted or unsubstituted $C_1$-$C_4$ alkyl.

$R^{39}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCHF_2$, —$S(O)_2CHCH_2$, —$NHS(O)_2CHCH_2$, $R^{40}$-substituted or unsubstituted alkyl, $R^{40}$-substituted or unsubstituted heteroalkyl, $R^{40}$-substituted or unsubstituted cycloalkyl, $R^{40}$-substituted or unsubstituted heterocycloalkyl, $R^{40}$-substituted or unsubstituted aryl, or $R^{40}$-substituted or unsubstituted heteroaryl.

In embodiments, $R^8$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCHF_2$, $R^{41}$-substituted or unsubstituted alkyl, $R^{41}$-substituted or unsubstituted heteroalkyl, $R^{41}$-substituted or unsubstituted cycloalkyl, $R^{41}$-substituted or unsubstituted heterocycloalkyl, $R^{41}$-substituted or unsubstituted aryl, or $R^{41}$-substituted or unsubstituted heteroaryl.

$R^{41}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCHF_2$, —$S(O)_2CHCH_2$, —$NHS(O)_2CHCH_2$, $R^{42}$-substituted or unsubstituted alkyl, $R^{42}$-substituted or unsubstituted heteroalkyl, $R^{42}$-substituted or unsubstituted cycloalkyl, $R^{42}$-substituted or unsubstituted heterocycloalkyl, $R^{42}$-substituted or unsubstituted aryl, or $R^{42}$-substituted or unsubstituted heteroaryl.

$R^{42}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCHF_2$, —$S(O)_2CHCH_2$, —$NHS(O)_2CHCH_2$, $R^{43}$-substituted or unsubstituted alkyl, $R^{43}$-substituted or unsubstituted heteroalkyl, $R^{43}$-substituted or unsubstituted cycloalkyl, $R^{43}$-substituted or unsubstituted heterocycloalkyl, $R^{43}$-substituted or unsubstituted aryl, or $R^{43}$-substituted or unsubstituted heteroaryl.

In embodiments, $R^7$ and $R^8$ are joined together to form a substituted or unsubstituted heterocycloalkyl or substituted or unsubstituted heteroaryl. $R^7$ and $R^8$ may be joined together to form a substituted or unsubstituted heterocycloalkyl. $R^7$ and $R^8$ may be joined together to form a substituted or unsubstituted 3 to 8 membered heterocycloalkyl. $R^7$ and $R^8$ may be joined together to form a substituted 3 to 8 membered heterocycloalkyl. $R^7$ and $R^8$ may be joined together to form a substituted or unsubstituted 5 to 7 membered heterocycloalkyl. $R^7$ and $R^8$ may be joined together to form a substituted 5 to 7 membered heterocycloalkyl. $R^7$ and $R^8$ may be joined together to form an $R^{38}$-substituted 5 to 7 membered heterocycloalkyl, wherein $R^{38}$ is as described herein above. $R^7$ and $R^8$ may be joined together to form an $R^{38}$-substituted 5 to 7 membered heterocycloalkyl, wherein $R^{38}$ is independently a substituted or unsubstituted alkyl or substituted or unsubstituted heteroalkyl. $R^7$ and $R^8$ may be joined together to form an $R^{38}$-substituted 5 to 7 membered heterocycloalkyl, wherein $R^{38}$ is independently a substituted or unsubstituted $C_1$-$C_8$ alkyl or substituted or unsubstituted 2 to 8 membered heteroalkyl. $R^7$ and $R^8$ may be joined together to form a substituted or unsubstituted pyrrolidinyl. $R^7$ and $R^8$ may be joined together to form a substituted or unsubstituted piperazinyl.

In embodiments, $R^9$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCHF_2$, $R^{44}$-substituted or unsubstituted alkyl, $R^{44}$-substituted or unsubstituted heteroalkyl, $R^{44}$-substituted or unsubstituted cycloalkyl, $R^{44}$-substituted or unsubstituted heterocycloalkyl, $R^{44}$-substituted or unsubstituted aryl, or $R^{44}$-substituted or unsubstituted heteroaryl.

$R^{44}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCHF_2$, $R^{45}$-substituted or unsubstituted alkyl, $R^{45}$-substituted or unsubstituted heteroalkyl, $R^{45}$-substituted or unsubstituted cycloalkyl, $R^{45}$-substituted or unsubstituted heterocycloalkyl, $R^{45}$-substituted or unsubstituted aryl, or $R^{45}$-substituted or unsubstituted heteroaryl.

$R^{45}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCHF_2$, $R^{46}$-substituted or unsubstituted alkyl, $R^{46}$-substituted or unsubstituted heteroalkyl, $R^{46}$-substituted or unsubstituted cycloalkyl, $R^{46}$-substituted or unsubstituted heterocycloalkyl, $R^{46}$-substituted or unsubstituted aryl, or $R^{46}$-substituted or unsubstituted heteroaryl.

Each $R^{22}$, $R^{25}$, $R^{28}$, $R^{31}$, $R^{34}$, $R^{37}$, $R^{40}$, $R^{43}$, $R^{46}$, and $R^{49}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, the compound of formula (I) has the formula:

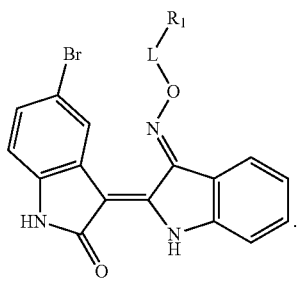
(II)

The compound of formula (I) or formula (II), including pharmaceutically acceptable salts thereof, provided herein, may include a protonated nitrogen cation. The of formula (I) or formula (II), including pharmaceutically acceptable salts thereof, provided herein, may include a plurality of protonated nitrogen cations.

In embodiments, the compound of formula (I) has the formula:

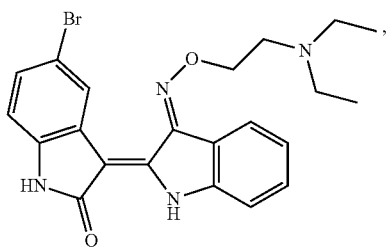
(1276)

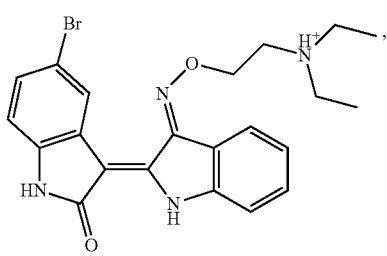
(1277)

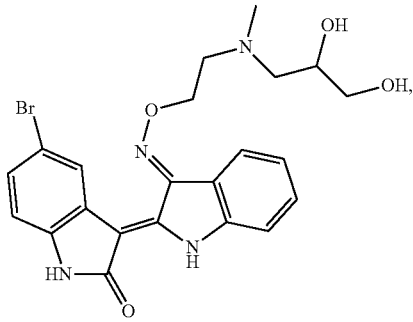
(1278)

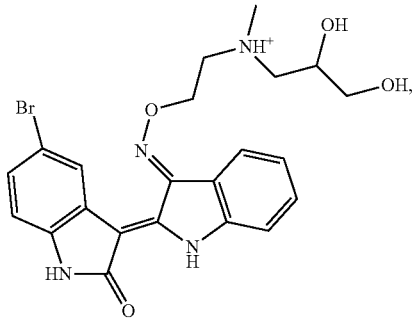
(1279)

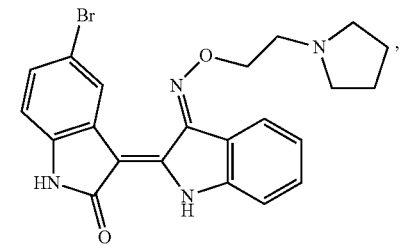
(1280)

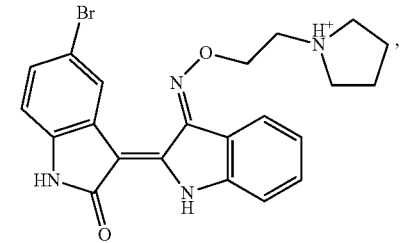
(1281)

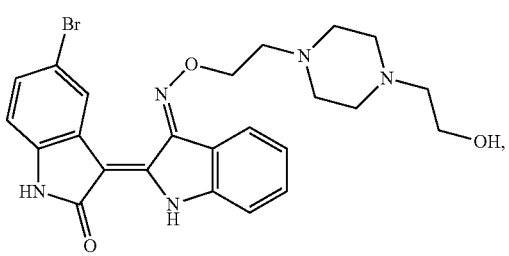
(1282)

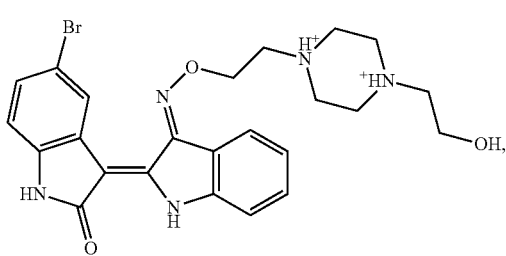
(1283)
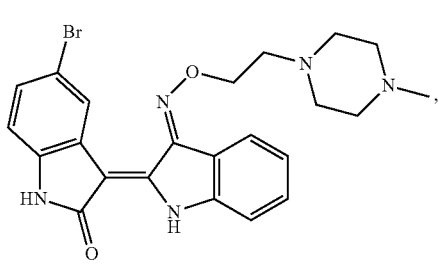
(1284)
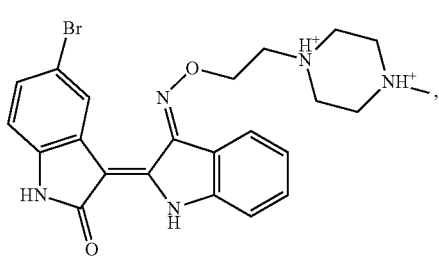
(1285)
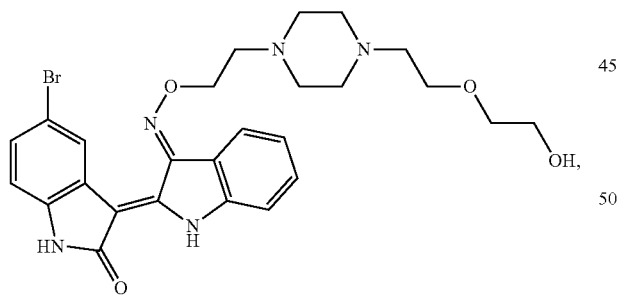
(1286)
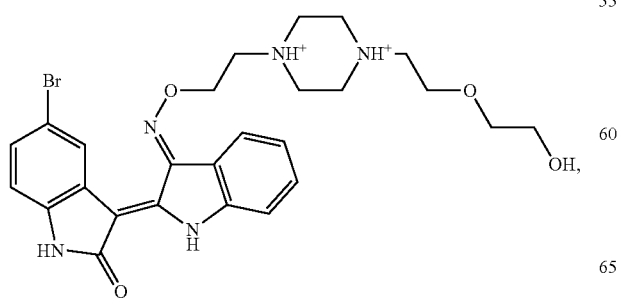
(1287)
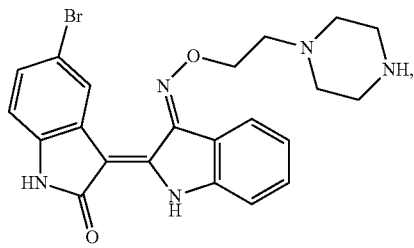
(1288)
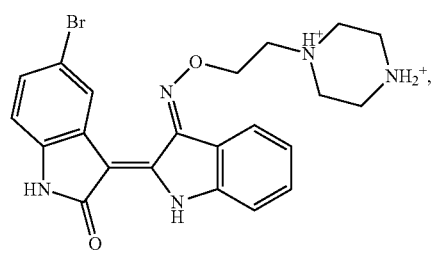
(1289)
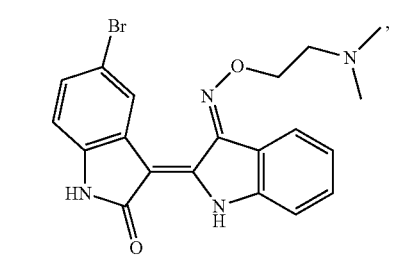
(1501)
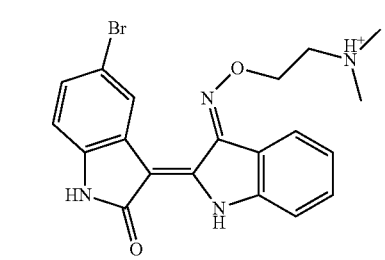
(1501p)
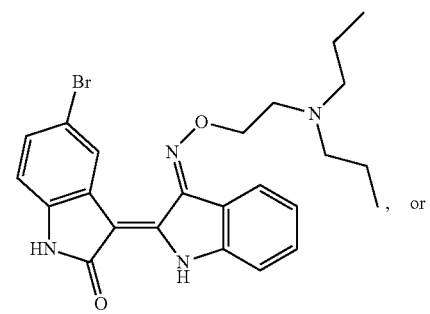
(1502) , or (1502p)
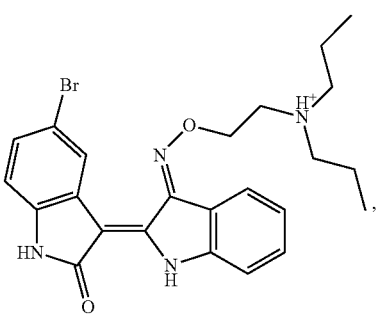
including pharmaceutically acceptable salts thereof.
In embodiments, the compound of formula (I) has the formula:
(XNH5)
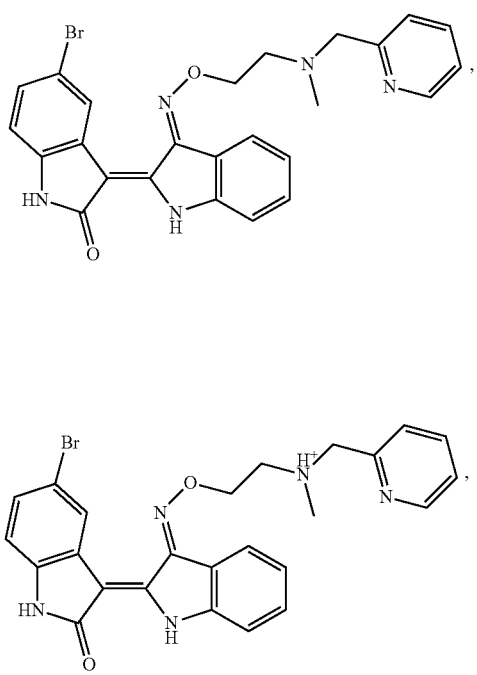
(XNH6)
(XNH6p)
(XNH7)
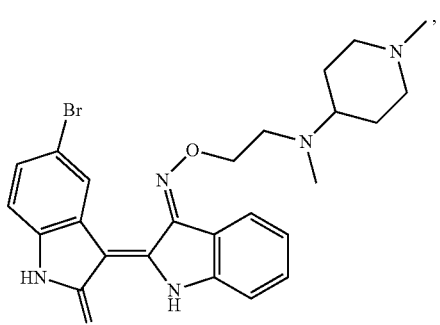
(XNH7p)
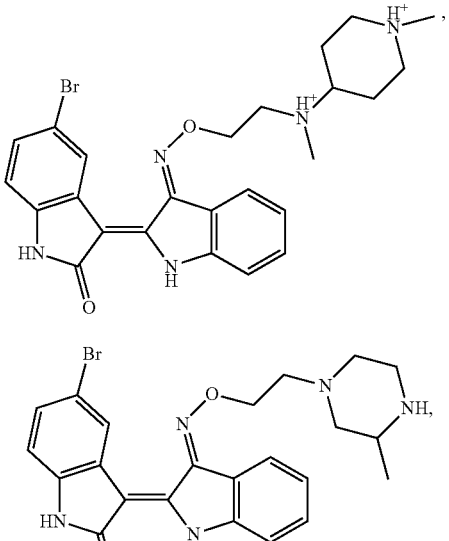
(XNH9)
(XNH9p)
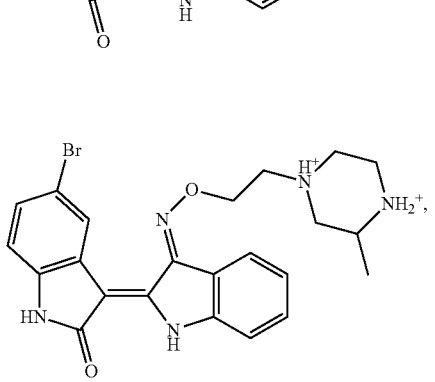
(XNH10)
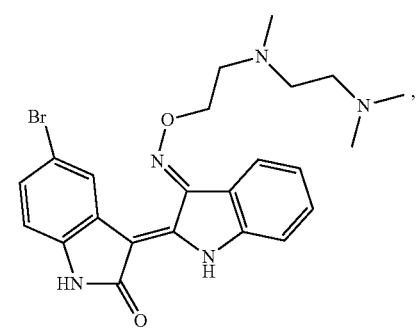

-continued

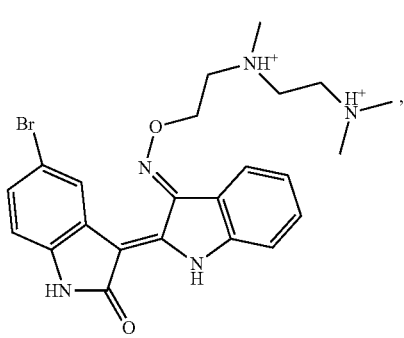
(XNH10p)

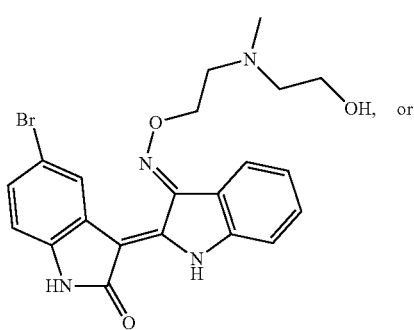
(XNH12)

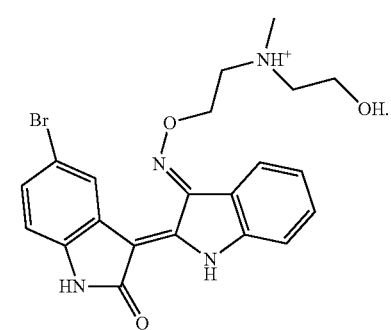
(XNH12p)

In embodiments, the compound has the formula 1276, or a pharmaceutically acceptable salt thereof. In embodiments, the compound has the formula 1277, or a pharmaceutically acceptable salt thereof. In embodiments, the compound has the formula 1278, or a pharmaceutically acceptable salt thereof. In embodiments, the compound has the formula 1279, or a pharmaceutically acceptable salt thereof. In embodiments, the compound has the formula 1280, or a pharmaceutically acceptable salt thereof. In embodiments, the compound has the formula 1281, or a pharmaceutically acceptable salt thereof. In embodiments, the compound has the formula 1282, or a pharmaceutically acceptable salt thereof. In embodiments, the compound has the formula 1283, or a pharmaceutically acceptable salt thereof. In embodiments, the compound has the formula 1284, or a pharmaceutically acceptable salt thereof. In embodiments, the compound has the formula 1285, or a pharmaceutically acceptable salt thereof. In embodiments, the compound has the formula 1286, or a pharmaceutically acceptable salt thereof. In embodiments, the compound has the formula 1287, or a pharmaceutically acceptable salt thereof. In embodiments, the compound has the formula 1288, or a pharmaceutically acceptable salt thereof. In embodiments, the compound has the formula (1289). In embodiments, the compound has the formula 1501, or a pharmaceutically acceptable salt thereof. In embodiments, the compound has the formula 1501p, or a pharmaceutically acceptable salt thereof. In embodiments, the compound has the formula 1502, or a pharmaceutically acceptable salt thereof. In embodiments, the compound has the formula 1502p, or a pharmaceutically acceptable salt thereof. In embodiments, the compound has the formula XNH5, or a pharmaceutically acceptable salt thereof. In embodiments, the compound has the formula XNH6, or a pharmaceutically acceptable salt thereof. In embodiments, the compound has the formula XNH6p, or a pharmaceutically acceptable salt thereof. In embodiments, the compound has the formula XNH7, or a pharmaceutically acceptable salt thereof. In embodiments, the compound has the formula XNH7p, or a pharmaceutically acceptable salt thereof. In embodiments, the compound has the formula XNH9, or a pharmaceutically acceptable salt thereof. In embodiments, the compound has the formula XNH9p, or a pharmaceutically acceptable salt thereof. In embodiments, the compound has the formula XNH10, or a pharmaceutically acceptable salt thereof. In embodiments, the compound has the formula XNH10p, or a pharmaceutically acceptable salt thereof. In embodiments, the compound has the formula XNH12, or a pharmaceutically acceptable salt thereof. In embodiments, the compound has the formula XNH12p, or a pharmaceutically acceptable salt thereof.

The compound of formula (I) may be provided as a component of a pharmaceutical composition. The pharmaceutical composition may include a pharmaceutically acceptable excipient. Thus, in embodiments, the method includes administering the compound of formula (I) to treat cancer in the subject. In embodiments, the pharmaceutical composition includes a second active agent (e.g. anti-cancer agent).

Also provided herein are compositions having the formula:

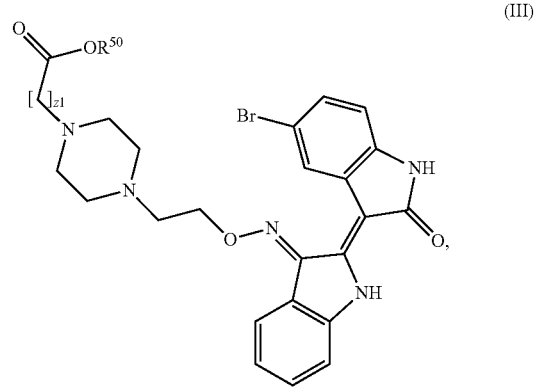
(III)

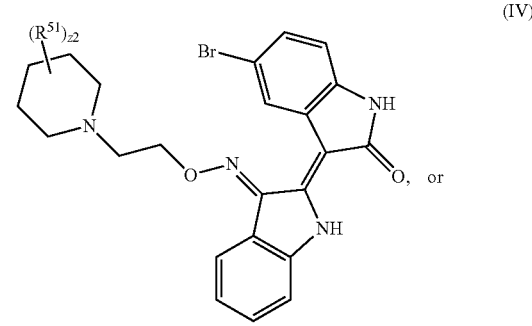
(IV)

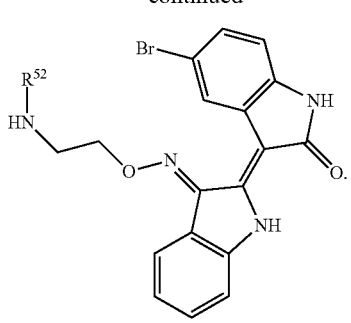

(V)

In the compound of formula (III), $R^{50}$ is hydrogen, halogen, —$CF_3$, —CN, —OH, —$NH_2$, —COOH, —$CH_2COOH$, —$CONH_2$, —$NO_2$, —SH, —$OCF_3$, —$OCHF_2$, or unsubstituted alkyl. In the compound of formula (IV), $R^{51}$ is hydrogen, oxo, halogen, —$CF_3$, —CN, —OH, —$NR^{51A}R^{51B}$, —COOH, —$CH_2COOH$, —$CONH_2$, —$NO_2$, —SH, —$OCF_3$, —$OCHF_2$, unsubstituted alkyl, or unsubstituted heteroalkyl. $R^{51A}$ and $R^{51B}$ are independently hydrogen or substituted or unsubstituted (e.g. unsubstituted) alkyl (e.g. $C_1$-$C_{10}$ alkyl). In the compound of formula (V), $R^{52}$ is halogen, —$CF_3$, —CN, —OH, —$NH_2$, —COOH, —$CONH_2$, or unsubstituted alkyl. The symbols z1 and z2 are independently 0, 1, 2, 3, 4, or 5. The compounds of formula (III), (IV), or (V) include pharmaceutically acceptable salts thereof. In embodiments, the compounds of formula (III), (IV), or (V) include a protonated nitrogen cation. In embodiments, the compounds of formula (III), (IV), or (V) include two or more protonated nitrogen cations.

In embodiments, $R^{50}$ is hydrogen, halogen, —$CF_3$, —CN, —OH, —$NH_2$, —COOH, —$CH_2COOH$, —$CONH_2$, —$NO_2$, —SH, —$OCF_3$, —$OCHF_2$. $R^{50}$ may be hydrogen, halogen, —$CF_3$, —$NH_2$, or —$CONH_2$. $R^{50}$ may be hydrogen, halogen, or unsubstituted alkyl. $R^{50}$ may be hydrogen or unsubstituted alkyl. $R^{50}$ may be hydrogen or $C_1$-$C_5$ unsubstituted alkyl. $R^{50}$ may be unsubstituted $C_1$-$C_5$ alkyl. $R^{50}$ may be hydrogen, methyl, ethyl, or propyl. $R^{50}$ may be methyl, ethyl, or propyl. The symbol z1 may be 0, 1, or 2. The symbol z1 may be 1 or 2.

In embodiments, $R^{51}$ is hydrogen, oxo, halogen, —$CF_3$, —CN, —OH, —$NH_2$, —COOH, —$CH_2COOH$, —$CONH_2$, —$NO_2$, —SH, —$OCF_3$, —$OCHF_2$. In embodiments, $R^{51}$ is hydrogen, unsubstituted alkyl, or unsubstituted heteroalkyl. In embodiments, $R^{51}$ is unsubstituted alkyl, or unsubstituted heteroalkyl. $R^{51}$ may be hydrogen, oxo, halogen, —$CF_3$, —CN, —OH, —$NH_2$, —COOH, —$CH_2COOH$, —$CONH_2$, —$NO_2$, or unsubstituted alkyl. $R^{51}$ may be hydrogen, —$CH_2COOH$, unsubstituted alkyl or unsubstituted heteroalkyl. $R^{51}$ may be —$CH_2COOH$, unsubstituted alkyl or unsubstituted heteroalkyl. $R^{51}$ may be hydrogen, —$CH_2COOH$, unsubstituted $C_1$-$C_5$ alkyl or unsubstituted 2 to 6 membered heteroalkyl. $R^{51}$ may be —$CH_2COOH$, unsubstituted $C_1$-$C_5$ alkyl or unsubstituted 2 to 6 membered heteroalkyl. $R^{51}$ may be hydrogen. $R^{51}$ may be —$CH_2COOH$. In embodiments, $R^{51}$ is not hydrogen. In embodiments, $R^{51}$ is not —$CH_2COOH$.

$R^{51}$ may be unsubstituted alkyl. $R^{51}$ may be hydrogen or unsubstituted alkyl. $R^{51}$ may be hydrogen or unsubstituted $C_1$-$C_5$ alkyl. $R^{51}$ may be unsubstituted $C_1$-$C_5$ alkyl. $R^{51}$ may be hydrogen or methyl, ethyl or propyl. $R^{51}$ may be methyl, ethyl, or propyl. $R^{51}$ may be unsubstituted heteroalkyl. $R^{51}$ may be hydrogen or unsubstituted heteroalkyl. $R^{51}$ may be hydrogen or 2 to 6 membered heterocycloalkyl. $R^{51}$ may be 2 to 6 membered heterocycloalkyl. The symbol z2 may be 0, 1, or 2.

$R^{51A}$ and $R^{51B}$ may be hydrogen. In embodiments, at least one of $R^{51A}$ and $R^{51B}$ is not hydrogen. $R^{51A}$ and $R^{51B}$ may independently be hydrogen or substituted or unsubstituted alkyl. $R^{51A}$ and $R^{51B}$ may independently be substituted or unsubstituted alkyl. $R^{51A}$ and $R^{51B}$ may independently be unsubstituted alkyl. $R^{51A}$ and $R^{51B}$ may independently be hydrogen or substituted or unsubstituted $C_1$-$C_{10}$ alkyl. $R^{51A}$ and $R^{51B}$ may independently be substituted or unsubstituted $C_1$-$C_{10}$ alkyl. $R^{51A}$ and $R^{51B}$ may independently be unsubstituted $C_1$-$C_{10}$ alkyl. $R^{51A}$ and $R^{51B}$ may independently be hydrogen or substituted or unsubstituted $C_1$-$C_8$ alkyl. $R^{51A}$ and $R^{51B}$ may independently be substituted or unsubstituted $C_1$-$C_8$ alkyl. $R^{51A}$ and $R^{51B}$ may independently be unsubstituted $C_1$-$C_8$ alkyl. $R^{51A}$ and $R^{51B}$ may independently be hydrogen or substituted or unsubstituted $C_1$-$C_5$ alkyl. $R^{51A}$ and $R^{51B}$ may independently be substituted or unsubstituted $C_1$-$C_5$ alkyl. $R^{51A}$ and $R^{51B}$ may independently be unsubstituted $C_1$-$C_5$ alkyl. $R^{51A}$ and $R^{51B}$ may independently be hydrogen or methyl, ethyl or propyl. $R^{51A}$ and $R^{51B}$ may independently be methyl, ethyl or propyl. $R^{51A}$ and $R^{51B}$ may independently be hydrogen or methyl. $R^{51A}$ and $R^{51B}$ may be methyl. $R^{51A}$ and $R^{51B}$ may independently be hydrogen or unsubstituted ethyl. $R^{51A}$ and $R^{51B}$ may be unsubstituted ethyl. $R^{51A}$ and $R^{51B}$ may independently be hydrogen or unsubstituted propyl. $R^{51A}$ and $R^{51B}$ may be unsubstituted propyl. Where either or both of $^{R5}$ and $R^{51B}$ are substituted alkyl, they may be independently substituted with oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{52}$ is halogen, —$CF_3$, —CN, —OH, —$NH_2$, —COOH, —$CONH_2$. In embodiments, $R^{52}$ is unsubstituted alkyl. $R^{52}$ may be unsubstituted $C_1$-$C_5$ alkyl. $R^{52}$ may be methyl, ethyl, or propyl. $R^{52}$ may be methyl. $R^{52}$ may be ethyl. $R^{52}$ may be propyl. In embodiments, $R^{52}$ is a linear (e.g. unbranched) alkyl. In embodiments, $R^{52}$ is not a branched alkyl.

In embodiments, the compound of formula (III), (IV), or (V) has the formula:

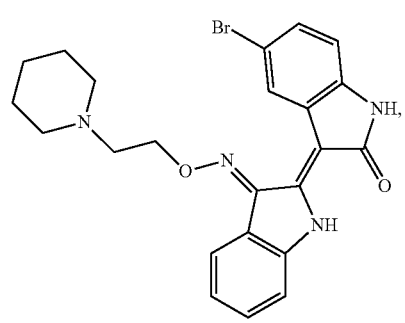

(5IN-6NC1)

-continued
(5IN-6NC1p)
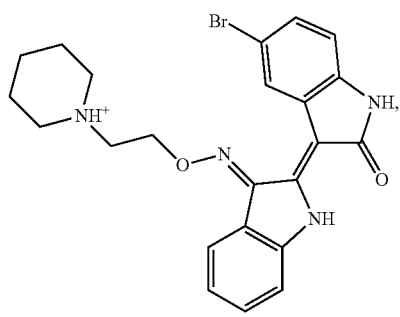
(5IN-1NH1)
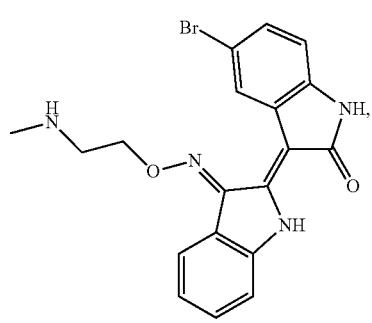
(5IN-1NH1p)
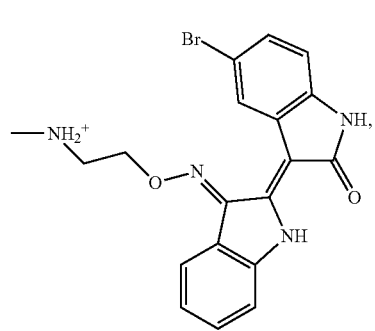
(5IN-6NNC6)
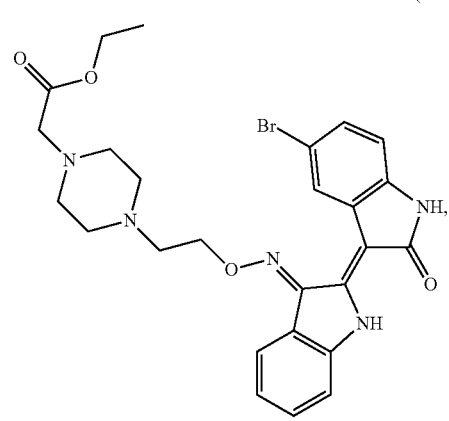
(5IN-6NNC6p)
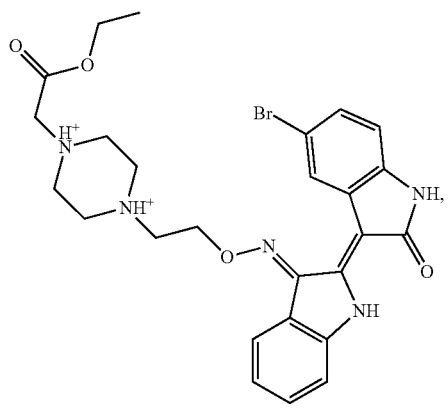
(5IN-6NNC7)
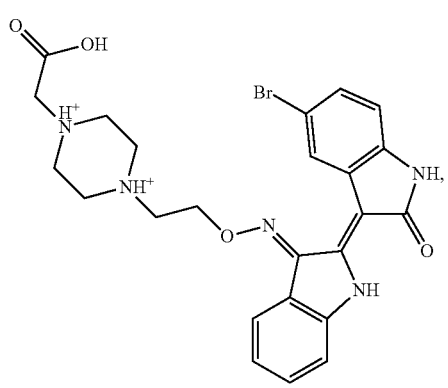
(5IN-6NNC7p)
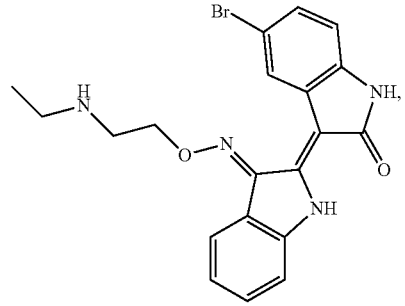
(5IN-1NH2)

(5IN-1NH2p)
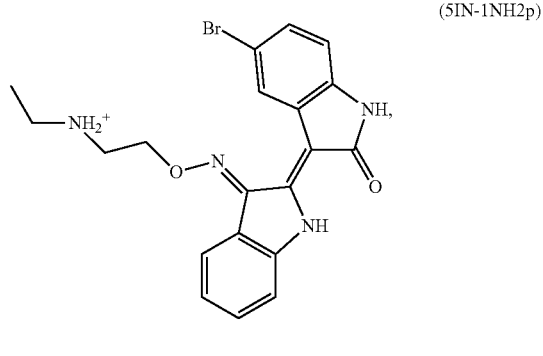
(5IN-1NH1)
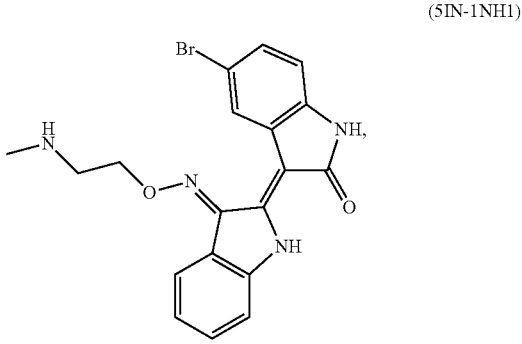
(5IN-6NC2)
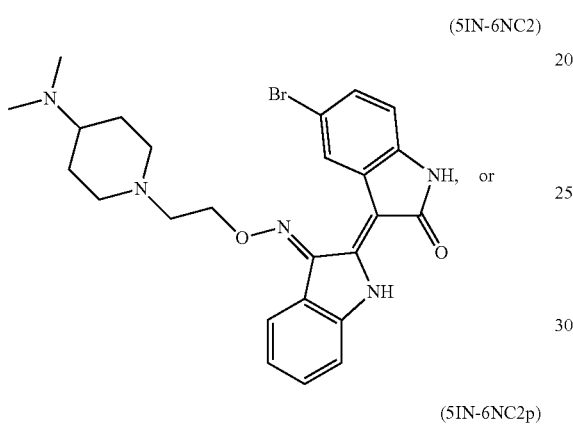
(5IN-6NNC6)
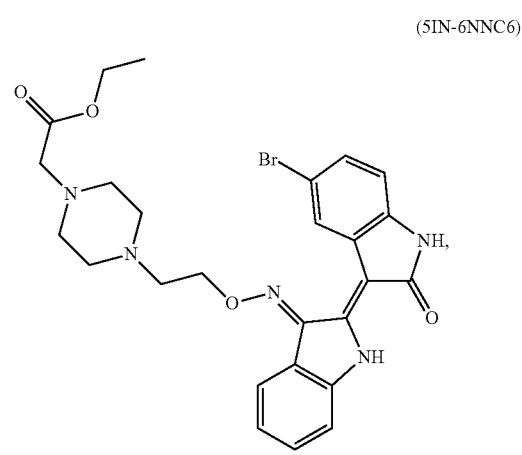
(5IN-6NC2p)
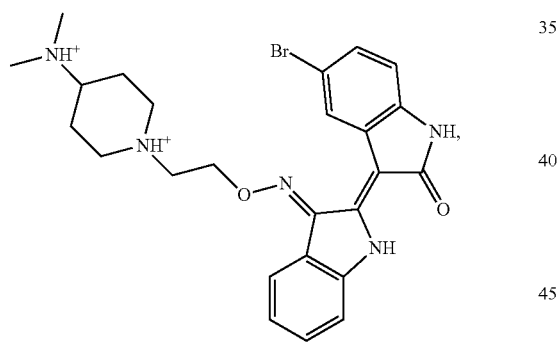
(5IN-6NNC7)
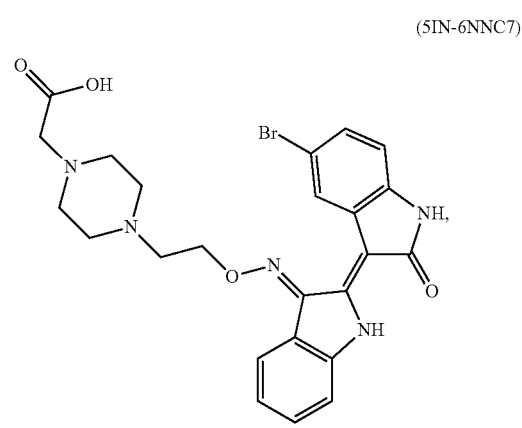
including pharmaceutically acceptable salts thereof
In embodiments, the compound of formula (III), (IV), or (V) has the formula:
(5IN-6NC1)
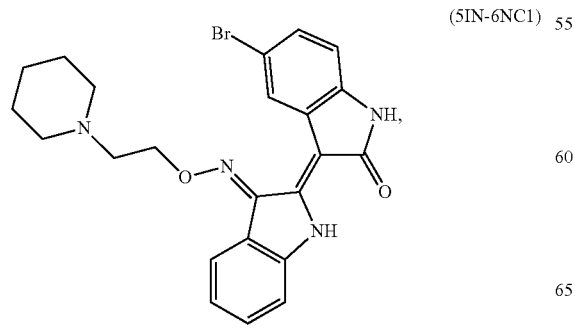
(5IN-1NH2)
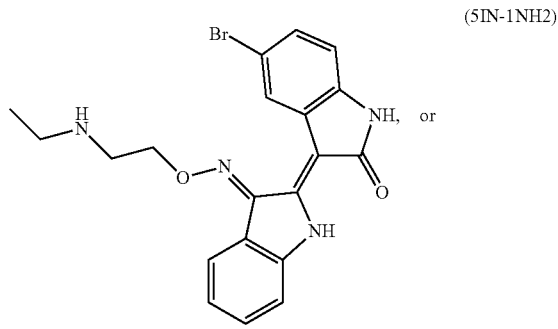
or (5IN-6NC2)

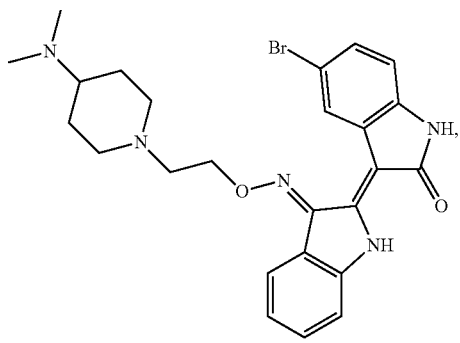

including pharmaceutically acceptable salts thereof

In embodiments, the compound has the formula 5IN-6NC1, including pharmaceutically acceptable salts thereof. In embodiments, the compound has the formula 5IN-1NH1, including pharmaceutically acceptable salts thereof, including pharmaceutically acceptable salts thereof. In embodiments, the compound has the formula 5IN-6NNC6, including pharmaceutically acceptable salts thereof. In embodiments, the compound has the formula 5IN-6NNC7, including pharmaceutically acceptable salts thereof. In embodiments, the compound has the formula 5IN-1NH2, including pharmaceutically acceptable salts thereof. In embodiments, the compound has the formula 5IN-6NC2, including pharmaceutically acceptable salts thereof In embodiments, the compound has the formula:

(5IN-1NH1s)

The compounds described herein may be provided as a pharmaceutical composition. The pharmaceutical composition may include a pharmaceutically acceptable excipient as described herein. In embodiments, the pharmaceutical composition includes at least one additional active agent, such as, for example, an anti-cancer agent described herein. In embodiments, the pharmaceutical composition includes one or more of the compounds described herein, e.g. formula (I), (II), (III), (IV), or (V) including embodiments thereof.

II. METHODS OF TREATMENT

1. Methods of Treating Cancer

The compounds described herein are useful methods of treating cancer. Such methods include administering to a subject in need thereof an effective amount of a compound having formula (III), (IV), or (V), including embodiments and pharmaceutically acceptable salts thereof. In embodiments, the compound has the formula 5IN-6NC1, 5IN-1NH1, 5IN-1NH1s, 5IN-6NNC6, 5IN-6NNC7, 5IN-1NH2, or 5IN-6NC2, including pharmaceutically acceptable salts thereof. In embodiments, the compound has the formula 5IN-6NC1 including pharmaceutically acceptable salts thereof. In embodiments, the compound has the formula 5IN-1NH1 including pharmaceutically acceptable salts thereof. In embodiments, the compound has the formula 5IN-1NH1s. In embodiments, the compound has the formula 5IN-6NNC6 including pharmaceutically acceptable salts thereof. In embodiments, the compound has the formula 5IN-6NNC7 including pharmaceutically acceptable salts thereof. In embodiments, the compound has the formula 5IN-1NH2 including pharmaceutically acceptable salts thereof. In embodiments, the compound has the formula 5IN-6NC2 including pharmaceutically acceptable salts thereof.

The cancer may be, for example, lung cancer, breast cancer, ovarian cancer, leukemia, lymphoma, melanoma, pancreatic cancer, sarcoma, bladder cancer, bone cancer, brain cancer, cervical cancer, colon cancer, esophageal cancer, gastric cancer, liver cancer, head and neck cancer, kidney cancer, myeloma, thyroid cancer, or prostate cancer. In embodiments, the cancer is lung cancer, breast cancer, ovarian cancer, leukemia, pancreatic cancer, colon cancer, liver cancer, kidney cancer, prostate cancer, or melanoma. The cancer may be lung cancer. The cancer may be breast cancer. The cancer may be ovarian cancer. The cancer may be prostate cancer. The cancer may be melanoma. The cancer may be leukemia.

2. Methods of Treating FLT3-AML

Also provided herein are methods of treating acute myeloid leukemia expressing FLT3-kinase in a subject in need thereof. In one aspect, the method includes administering an effective amount of a compound having the formula (I), including embodiments thereof. In the compound of formula (I), L, $R^1$ $R^2$, $R^3$ are as described herein, including embodiments thereof. In embodiments, the compound has formula (1289).

In another aspect, is a method of treating acute myeloid leukemia expressing FLT3-kinase in a subject in need thereof by administering an effective amount of a compound having the formula (II), (III), or (IV), as described herein, including embodiments thereof. In embodiments, the method includes administering an effective amount of a compound having the formula:

(5IN-6NC1)

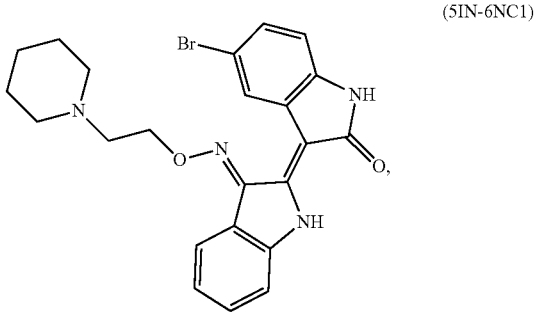

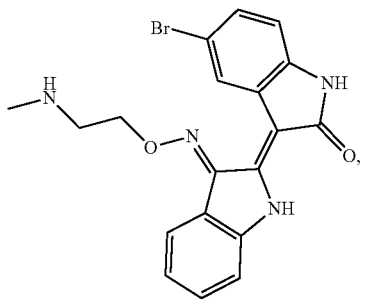

(5IN-1NH1)

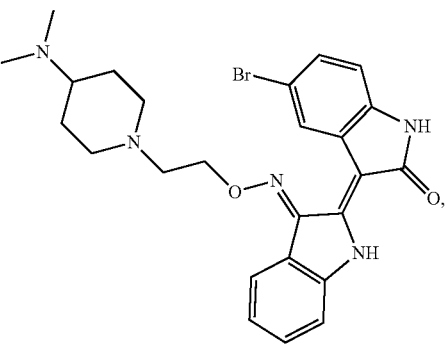

(5IN-6NC2)

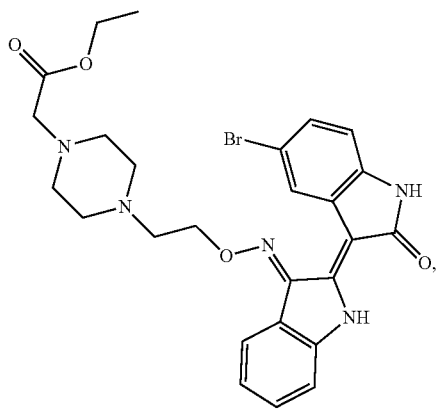

(5IN-6NNC6)

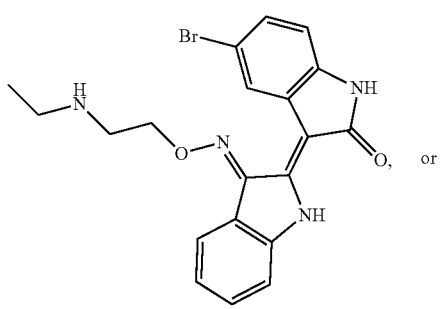

(5IN-6NNC7)

(5IN-1NH2)

including pharmaceutically acceptable salts thereof.

In another aspect, is a method of treating acute myeloid leukemia expressing FLT3-kinase in a subject in need thereof by administering an effective amount of a compound having the formula (1289), (5IN-6NC1), (5IN-1NH1), (5IN-1NH1s), (5IN-6NNC6), (5IN-6NNC7), (5IN-1NH2), or (5IN-6NC2)—including embodiments thereof.

In embodiments, the compound has the formula (5IN-1NH1) or (5IN-1NH1s). In embodiments, the compound has the formula (1289).

In embodiments, the compound of formula (I), (II), (III), (IV), or (V), including embodiments thereof is administered as a pharmaceutical composition. Thus, in embodiments, the compound of formula (III), (IV), or (V), including embodiments thereof, is administered as a pharmaceutical composition. The pharmaceutical composition is as described herein and may include a pharmaceutically acceptable excipient.

In embodiments of the methods described herein, the compounds described herein are co-administered with a second active agent. In embodiments, the second active agent is a second compound having the formula (I), (II), (III), (IV), or (V) as described herein, including embodiments and pharmaceutically acceptable salts thereof. The second compound may be administered at a therapeutically effective amount to the subject in need thereof. In embodiments, the second active agent is an effective amount of an anti-cancer agent. Thus, in embodiments, the compound is co-administered with an effective amount of an anti-cancer agent. In embodiments, the anti-cancer agent is a chemotherapeutic agent (e.g. a chemical composition or compound having antineoplastic properties or the ability to inhibit the growth or proliferation of cells).

In embodiments of the methods described herein, the FLT3-kinase may be a FLT3-wildtype kinase (i.e. a FLT kinase having SEQ ID NO:1, or a functional fragment thereof), or a FLT3-mutant kinase. The FLT3-kinase may be a FLT3-mutant kinase. In embodiments, the FLT3-mutant kinase is a FLT3-TKD mutant kinase and includes a mutation at an amino acid residue position corresponding to D835, I836, D839, S840, N841, or Y842 of SEQ ID NO:1 as described herein. Thus, FLT3-TKD mutant kinase may include a mutation at an amino acid residue position corresponding to D835 of SEQ ID NO:1 as described herein. The FLT3-TKD mutant kinase may include a mutation at an amino acid residue position corresponding to I836 of SEQ ID NO:1 as described herein. The FLT3-TKD mutant kinase may include a mutation at an amino acid residue position corresponding to D839 of SEQ ID NO:1 as described herein. The FLT3-TKD mutant kinase may include a mutation at an amino acid residue position corresponding to S840 of SEQ ID NO:1 as described herein. The FLT3-TKD mutant kinase may include a mutation at an amino acid residue position corresponding to N841 of SEQ ID NO:1 as described herein. The FLT3-TKD mutant kinase may include a mutation at an amino acid residue position corresponding to Y842 of SEQ ID NO:1 as described herein. In embodiments, the FLT3-TKD mutant kinase includes at least two mutations of the amino acid residues corresponding to positions D835, I836, D839, S840, N841, or Y842 of SEQ ID NO:1 as described herein. In embodiments, the FLT3-TKD mutant kinase includes at least three mutations of the amino acid residues corresponding to positions D835, I836, D839, S840, N841, or Y842 of SEQ ID NO:1 as described herein. In embodiments, the FLT3-TKD mutant kinase includes at least four mutations of the amino acid residues corresponding to positions D835, I836, D839, S840, N841, or Y842 of SEQ ID NO:1 as described herein. In embodiments, the FLT3-TKD mutant kinase includes at least five mutations of the amino acid residues corresponding to positions D835, I836, D839, S840, N841, or Y842 of SEQ ID NO:1 as described herein. In embodiments, the FLT3-TKD mutant kinase includes mutation of each amino acid residue corresponding to positions D835, I836, D839, S840, N841, or Y842 of SEQ ID NO:1 as described herein.

In embodiments, the FLT3-TKD mutant kinase includes at least one mutation at an amino acid residue position corresponding to D835, D839, or Y842 of SEQ ID NO:1. In embodiments, the FLT3-TKD mutant kinase includes at least two mutations at amino acid residue positions corresponding to D835, D839, or Y842 of SEQ ID NO:1. In embodiments, the FLT3-TKD mutant kinase includes mutation at amino acid residue positions corresponding to D835, D839, or Y842 of SEQ ID NO:1.

In embodiments, the FLT3-TKD mutant kinase includes a D835Y, D835H, D835V or D835E mutation at the residue corresponding to D835 of SEQ ID NO:1. In embodiments, the FLT3-TKD mutant kinase includes deletion of the residue corresponding to D835. In embodiments, the FLT3-TKD mutant kinase includes a I836L or I836M mutation at the residue corresponding to I836 of SEQ ID NO:1. In embodiments, the FLT3-TKD mutant kinase includes deletion of the residue corresponding to I836. In embodiments, the FLT3-TKD mutant kinase includes a D839G mutation at the residue corresponding to D839 of SEQ ID NO:1.

In embodiments, the FLT3-mutant kinase is a FLT3-ITD mutant kinase as described herein. In embodiments, the FLT3-ITD mutant kinase includes at least one mutation of the residues corresponding to positions D835, I836, D839, S840, N841, or Y842 of SEQ ID NO:1 (i.e. the FLT3-mutant kinase is a FLT3-ITD-TKD mutant kinase) as described herein. The FLT3-ITD mutant kinase may include at least two mutations of the residues corresponding to positions D835, I836, D839, S840, N841, or Y842 of SEQ ID NO:1 as described herein. In embodiments, the FLT3-ITD mutant kinase includes at least one mutation of the residues corresponding to positions D835, D839, or Y842 of SEQ ID NO:1 (i.e. the FLT3-mutant kinase is a FLT3-ITD-TKD mutant kinase) as described herein. The FLT3-ITD mutant kinase may include at least two mutations of the residues corresponding to positions D835, D839, or Y842 of SEQ ID NO:1 as described herein. The FLT-ITD may include mutation of the residues corresponding to position D835, D839, and Y842 of SEQ ID NO:1 as described herein.

In embodiments, the FLT3-mutant kinase is tyrosine kinase inhibitor resistant (activity and/or expression of the FLT3-mutant kinase is not sufficiently inhibited by a tyrosine kinase inhibitor thereby imparting resistance to a tyrosine kinase inhibitor). The tyrosine kinase inhibitor may be as described herein, including embodiments thereof. In embodiments, the FLT3-mutant kinase is AC220 drug resistant. In embodiments, the AC220 drug resistant FLT3-mutant kinase is FLT3-ITD mutant kinase.

Also provided herein are methods of treating acute myeloid leukemia expressing FLT3-mutant kinase, wherein the FLT3-mutant kinase is a FLT3-TKD mutant kinase as described herein in a subject in need thereof. In one aspect, the method includes administering an effective amount of a compound having the formula (I), including embodiments and pharmaceutically acceptable salts thereof (e.g. formula (II) and embodiments thereof and pharmaceutically acceptable salts thereof). In another aspect, the method includes administering an effective amount of a compound having the formula (III), (IV), or (V) including embodiments and pharmaceutically acceptable salts thereof.

Also provided herein are methods of treating acute myeloid leukemia expressing FLT3-mutant kinase, wherein the FLT3-mutant kinase is a FLT3-ITD mutant kinase as described herein in a subject in need thereof. In one aspect, the method includes administering an effective amount of a compound having the formula (I), including embodiments and pharmaceutically acceptable salts thereof (e.g. formula (II) and embodiments thereof and pharmaceutically acceptable salts thereof). In another aspect, the method includes administering an effective amount of a compound having the formula (III), (IV), or (V) including embodiments and pharmaceutically acceptable salts thereof.

FLT3, AML, ITD, FLT3-TKD mutant kinase, and FLT3-ITD mutant kinase are as described herein, including embodiments thereof. In embodiments, the compound has the formula (III), (IV), or (V), as described herein, including embodiments and pharmaceutically acceptable salts thereof. The compound may be a compound of formula (1289), 5IN-6NC1, 5IN-1NH1, 5IN-6NNC6, 5IN-6NNC7, 5IN-1NH2, or 5IN-6NC2, including pharmaceutically acceptable salts thereof. In embodiments, the compound has the formula 5IN-1NH1 or 5IN-1NH1s as described herein. The compound may have the formula (1289). The compound may have the formula 5IN-6NC1, including pharmaceutically acceptable salts thereof. The compound may have the formula 5IN-1NH1, including pharmaceutically acceptable salts thereof. The compound may have the formula 5IN-1NH1. The compound may have the formula 5IN-6NNC6, including pharmaceutically acceptable salts thereof. The compound may have the formula 5IN-6NNC7, including pharmaceutically acceptable salts thereof. The compound may have the formula 5IN-1NH2, including pharmaceutically acceptable salts thereof. The compound may have the formula 5IN-6NC2, including pharmaceutically acceptable salts thereof

3. Methods of Treating ALL

Also provided herein are methods of treating acute lymphoblastic Leukemia (ALL), which expresses FLT3-kinase, in a subject in need thereof. In one aspect method includes administering an effective amount of a compound having formula (I) or (II), including embodiments thereof and pharmaceutically acceptable salts thereof. In another aspect, the method includes administering an effective amount of a compound having formula (III), (IV), or (V) as described herein including embodiments thereof and pharmaceutically acceptable salts thereof. The ALL may be precursor B-cell ALL or T-cell ALL as described herein. FLT3-kinase is as described herein, including embodiments thereof. Thus the FLT3-kinase may be a FLT3-mutant kinase (e.g. FLT3-ITD mutant kinase or FLT3-TKD mutant kinase). The compound may be a compound of formula (1289), 5IN-6NC1, 5IN-1NH1, 5IN-6NNC6, 5IN-6NNC7, 5IN-1NH2, or 5IN-6NC2, including pharmaceutically acceptable salts thereof. The compound may have the formula (1289), including pharmaceutically acceptable salts thereof. The compound may have the formula 5IN-6NC1, including pharmaceutically acceptable salts thereof. The compound may have the formula 5IN-1NH1, including pharmaceutically acceptable salts thereof. The compound may have the formula SIN-1NH1s. The compound may have the formula 5IN-6NNC6, including pharmaceutically acceptable salts thereof. The compound may have the formula 5IN-6NNC7, including pharmaceutically acceptable salts thereof. The compound may have the formula 5IN-1NH2, including pharmaceutically acceptable salts thereof. The compound may have the formula 5IN-6NC2, including pharmaceutically acceptable salts thereof.

4. Methods of Treating CML

Also provided herein are methods of treating chronic myelogenous leukemia (CML) expressing ABL1-kinase. In one aspect, the method includes administering an effective amount of a compound having formula (III), (IV), or (V), including pharmaceutically acceptable salts and embodiments thereof. In yet another aspect, the method includes administering an effective amount of a compound having formula 5IN-1NH1 or 5IN-1NH1s. In embodiments, the ABL1-kinase is a ABL1-mutant kinase. The mutant-ABL1 kinase may have a mutation of an amino acid residue as described herein (e.g. a mutation within SEQ ID NO:2). In embodiments, the ABL1-mutant kinase is a BCR-ABL1 mutant kinase has a mutation of an amino acid residue within SEQ ID NO:3. In embodiments, the mutation is of an amino acid corresponding to residue Y253, E255, V268, V270, T272, Y274, D276, T277, M278, E282, F283, A288, M290, K291, E292, I293, P296, L298, V299, Q300, G303, V304, C305, T306, F311, I314, T315, E316, F317, M318, Y320, G321, D325, Y326, L327, R328, E329, Q333, E334, A337, V339, L342, M343, A344, I347, A350, M351, E352, E355, K357, N358, F359, I360, L364, E373, N374, K378, V379, A380, D381, F382, T389, T392, T394, A395, H396, A399, P402, or T406 of SEQ ID NO:2 or SEQ ID NO:3.

In embodiments, the mutation is a D233H, T243S, M244V, L248V, G249D, G250E, G251S, Q252H, Y253(F/H), E255(K/V), V256L, Y257(F/R), F259S, K262E, D263G, K264R, S265R, V268A, V270A, T272A, Y274(C/R), D276N, T277P, M278K, E282G, F283S, A288(T/V), M290T, K291R, E292G, I293T, P296S, L298(M/P), V299L, Q300R, G303E, V304(A/D), C305(S/Y), T306A, F311L, I314V, T315(A/I), E316G, F317(I/L/V), M318T, Y320(C/H), G321E, D325H, Y326C, L327P, R328K, E329V, Q333L, A337V, V339G, L342E, M343(V/T), A344(T/V), I347V, A350T, M351T, E352(A/K), E355G, K357E, N358 (D/S), F359(C/I/V), I360(K/T), L364H, E373K, N374D, K378R, V379I, A380(T/V), D381G, F382L, T389S, T392A, T394A, A395G, H396(K/R/P), A399G, P402T or T406A mutation corresponding to residue numbers in SEQ ID NO:2 or SEQ ID NO:3. In embodiments, the mutation is a G250E, Q252H, Y253H, E255(K/V), V299L, T315(A/I), F317(I/LN), M351T, F359(C/I/V), or H396R mutation corresponding to residue numbers in SEQ ID NO:2 or SEQ ID NO:3. In embodiments, the mutation is a Y253H, E255(K/V), V299L, T315(A/I), F317(I/LN), or F359(C/I/V) mutation corresponding to residue numbers in SEQ ID NO:2 or SEQ ID NO:3. In embodiments, the mutations is a T315(A/I) mutation corresponding to residue numbers in SEQ ID NO:2 or SEQ ID NO:3. In embodiments, the mutation is a T315I mutation.

In embodiments, the BCR-ABL1 mutant kinase is tyrosine kinase inhibitor resistant (i.e. activity and/or expression of the ABL1 kinase or BCR-ABL1 mutant kinase is not inhibited by a tyrosine kinase inhibitor). The tyrosine kinase inhibitor may be as described herein, including embodiments thereof. In embodiments, the ABL1 kinase or BCR-ABL1 mutant kinase is imatinib drug resistant (e.g. a BCR-ABL1 mutant having a mutation (e.g. a T315I mutation) that has activity in the presence of imatinib).

The compound of formula (III), (IV), or (V) is as described as set forth above and described in the compositions section. The compound may have the formula 5IN-6NC1, including pharmaceutically acceptable salts thereof. The compound may have the formula 5IN-1NH1, including pharmaceutically acceptable salts thereof. The compound may have the formula 5IN-1NH1s. The compound may have the formula 5IN-6NNC6, including pharmaceutically acceptable salts thereof. The compound may have the formula 5IN-6NNC7, including pharmaceutically acceptable salts thereof. The compound may have the formula 5IN-1NH2, including pharmaceutically acceptable salts thereof. The compound may have the formula 5IN-6NC2, including pharmaceutically acceptable salts thereof.

III. METHODS OF MODULATING FLT3-KINASE ACTIVITY

Provided herein are methods of modulating activity of a FLT3-kinase. In one aspect, the method includes contacting a FLT3-kinase with a compound having formula (I), including embodiments and pharmaceutically acceptable salts thereof. In another aspect, the method includes contacting a FLT3-kinase with a compound having formula (III), (IV), or (V), including embodiments and pharmaceutically acceptable salts thereof In embodiments, the activity of FLT3-kinase is decreased (e.g. inhibited) after contacting the FLT3-kinase with a compound described herein (e.g. formula (I), (II), (III), (IV), or (V), including embodiments and pharmaceutically acceptable salts thereof). The compound may be a compound of formula (1289), 5IN-6NC1, 5IN-1NH1, 5IN-1NH1s, 5IN-6NNC6, 5IN-6NNC7, 5IN-1NH2, or 5IN-6NC2, including pharmaceutically acceptable salts thereof. The compound may have the formula (1289), including pharmaceutically acceptable salts thereof. The compound may have the formula 5IN-6NC1, including pharmaceutically acceptable salts thereof. The compound may have the formula 5IN-1NH1, including pharmaceutically acceptable salts thereof. The compound may have the formula 5IN-1NH1s. The compound may have the formula 5IN-6NNC6, including pharmaceutically acceptable salts thereof. The compound may have the formula 5IN-6NNC7, including pharmaceutically acceptable salts thereof. The compound may have the formula 5IN-1NH2, including pharmaceutically acceptable salts thereof. The compound may have the formula 5IN-6NC2, including pharmaceutically acceptable salts thereof.

The FLT3-kinase may be a FLT3-mutant kinase, as described herein, including embodiments thereof (e.g. a FLT3-TKD mutant kinase or FLT3-ITD mutant kinase, as described herein, including embodiments thereof).

IV. METHODS OF MODULATING TYPE III RECEPTOR TYROSINE KINASES

Provided herein are methods of modulating activity of a type III receptor tyrosine kinase. In one aspect, the method includes contacting a type III receptor tyrosine kinase with a compound having formula (III), (IV), or (V), including embodiments and pharmaceutically acceptable salts thereof. In another aspect, the method includes contacting a type III receptor tyrosine kinase with a compound having formula (I) or (II), including embodiments and pharmaceutically acceptable salts thereof The type III receptor tyrosine kinase may be FLT3 (including FLT3-mutant kinases described herein such as, for example, a FLT3-TKD mutant kinase or FLT3-ITD mutant kinase), c-Kit, FMS, PDGFRα, or PDGFRβ.

In embodiments, the activity of type III receptor tyrosine kinase is decreased (e.g. inhibited) after contacting the type III receptor tyrosine kinase with a compound described herein (e.g. formula (I), (II), (III), (IV), or (V), including embodiments and pharmaceutically acceptable salts thereof). The compound may be a compound of formula (1289), 5IN-6NC1, 5IN-1NH1, 5IN-1NH1s, 5IN-6NNC6, 5IN-6NNC7, 5IN-1NH2, or 5IN-6NC2, including pharmaceutically acceptable salts thereof. The compound may have the formula (1289), including pharmaceutically acceptable salts thereof. The compound may have the formula 5IN-6NC1, including pharmaceutically acceptable salts thereof. The compound may have the formula 5IN-1NH1, including pharmaceutically acceptable salts thereof. The compound may have the formula 5IN-1NH1s. The compound may have the formula 5IN-6NNC6, including pharmaceutically acceptable salts thereof. The compound may have the formula 5IN-6NNC7, including pharmaceutically acceptable salts thereof. The compound may have the formula 5IN-1NH2, including pharmaceutically acceptable salts thereof. The compound may have the formula 5IN-6NC2, including pharmaceutically acceptable salts thereof

V. EXAMPLES:

1. Example 1

FLT3-internal tandem duplication (ITD) mutations in juxtamembrane domain are detected in approximately 25% of AML patients. In addition, point mutations are observed in approximately 5%-10% of AML patients. Among these point mutations, the FLT3-D835Y mutation is predominant. The ITD mutation constitutively activates FLT3 and is associated with poor outcomes and higher relapse rate of AML in patients. FLT3 is also applicable to B-precursor cell acute lymphoblastic Leukemia (ALL) and T-cell ALL.

Figure 9A:
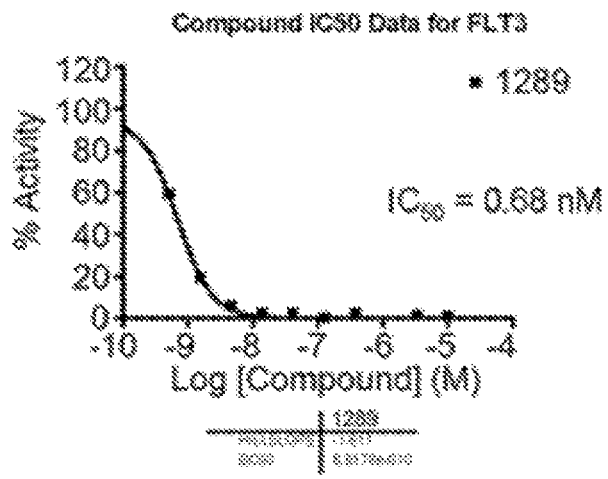
FIGS. 9A-9C: Compound (1289) inhibits FLT3 (FIG. 9A), FLT3 (D835Y) mutant (FIG. 9C) and FLT3-ITD mutant (FIG. 9B) kinase activities in vitro.
Figure 9B:
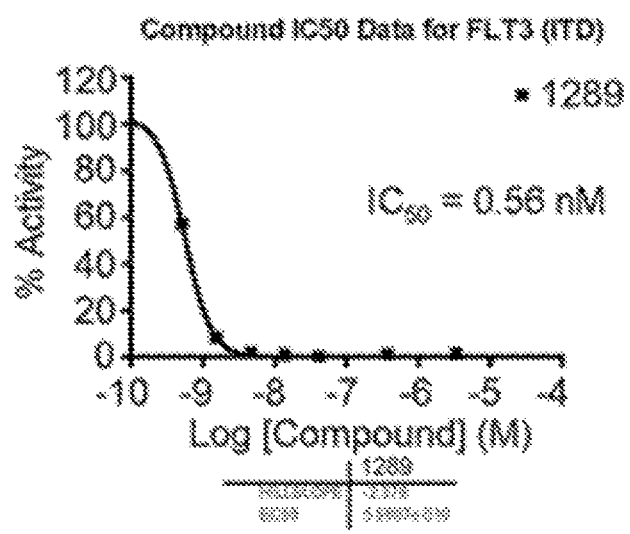
Figure 9C:
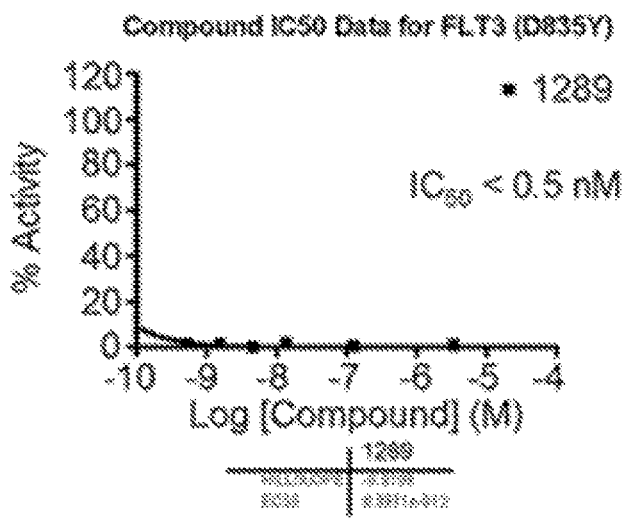

Formula (1289) [i.e., compound (1289)], a 5-bromo indirubin derivative, possesses potent tyrosine kinase inhibition activities. In particular, compound (1289) is potent against AML cell lines that are driven by FLT3 receptor kinase and mutant forms of FLT3 receptor kinases. It was discovered, inter alia, that compound (1289) possesses potent antitumor activities in MV4-11 and MOLM13 AML cells that harbor fms-like tyrosine kinase 3 (FLT3)-ITD mutations. This ITD mutation is believed to be a driver of this specific form of refractory AML. In addition, it was discovered, inter alia, that compound (1289) inhibits FLT3, FLT3-ITD mutant kinase, D835Y mutant FLT3-kinase activities in vitro. See FIGS. 6A-6B and FIGS. 7A-7B. Indeed, compound (1289) shows efficacy in vivo using MV4-11 AML SQ xenografts. See FIGS. 9A-9C. These findings suggest that 5-bromo indirubin derivatives (5-BIRDs), including compound (1289), are promising molecularly targeted therapeutic agents for treating AML and, more specifically, patients with FLT3 mutated AML-based cancers.

Compound (1289) showed strong antitumor activities against MV4-11 and MOLM13 AML cells with $IC_{50}$=1.8 nM and 2.3 nM, respectively. Compound (1289) was found to inhibit FLT3, FLT-ITD mutant, and D835Y mutant FLT3-kinase activities in vitro. Indeed, the compound potently inhibits these kinase activities in vitro with $IC_{50}$=0.68 nM, 0.56 nM and <0.5 nM, respectively. Furthermore, it was discovered, inter alia, that compound (1289) blocked phosphorylation of signal transducer and activator of transcription 5 (STAT5) and Erk1/2 in FLT-ITD mutated AML cells, suggesting that compound (1289) inhibits multiple FLT3 downstream signaling pathways such as STAT5 and MAPK/ERK. These results are well correlated with reduction of AML cell viability. Accordingly, compound (1289) could be used as a molecularly targeted agent for FLT3 and FLT3 mutant-based cancers.

2. Example 2

Compound (1289) inhibits activities of FMS, PDGFR α, PDGFR β and c-KIT in vitro. See Table 1. The kinase assays were performed with recombinant FMS, PDGFRα, PDGFRβ and c-KIT proteins. Briefly, proteins, freshly prepared substrates and $^{33}P$-ATP (specific activity 0.01 μCi/μl final) were mixed in reaction buffer (20 mM HEPES pH 7.5, 10 mM $MgCl_2$, 1 mM EGTA, 0.02% Brij35, 0.02 mg/ml BSA, 0.1 mM $Na_3VO_4$, 2 mM DTT) in the presence of DMSO as control or compound (1289). The mixtures were reacted for 120 min at room temperature. Samples were transferred onto P81 ion exchange paper and filters were extensively washed with 0.75% phosphoric acid. The radioactivities were monitored.

TABLE 1

| $IC_{50}$ values for compound (1289) for class III receptor tyrosine kinase family members in vitro. ||
| --- | --- |
| Class III Receptor Tyrosine Kinase | $IC_{50}$ (nM) |
| FMS | 7.6 |
| PDGFR α | 13.6 |
| PDGFR β | 1.2 |
| c-KIT | 47.7 |

3. Example 3

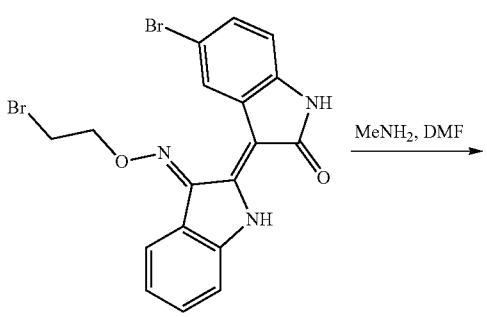

MeNH₂, DMF

-continued

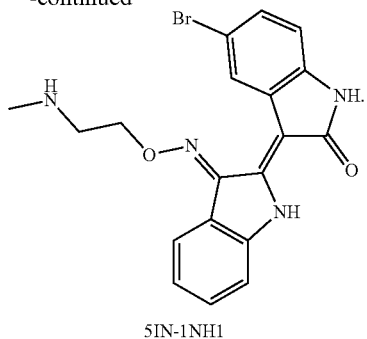

5IN-1NH1

To a stirred solution of starting material (SM) (23 mg, 0.05 mmol) in DMF (0.6 mL) were added 40% MeNH$_2$ (20 equiv). After 60 h at room temperature, water was added and the solid was filtered to give the product 5IN-1NH1 (17.4 mg, 84%). $^1$H NMR (400 MHz, CDCl$_3$) δ11.71 (b, 1H), 10.88 (b, 1H), 8.84 (d, J=2.0 Hz, 1H), 8.14 (d, J=7.8 Hz, 1H), 7.48-7.40 (m, 2H), 7.28 (dd, J=2.0, 8.2 Hz, 1H), 7.09-7.01 (m, 1H), 6.84 (d, J=8.2 Hz, 1H), 4.63 (t, J=5.6 Hz, 2H), 3.05 (t, J=5.6 Hz, 2H), 2.36 (s, 3H); $^{13}$C NMR (100 MHz, CDCl$_3$) δ170.9, 151.8, 145.8, 145.5, 138.0, 133.4, 128.8, 128.6, 125.7, 124.9, 122.4, 116.6, 112.9, 112.5, 111.0, 99.2, 76.8, 50.5, 36.7; HRMS C$_{19}$H$_{17}$BrN$_4$O$_2$ [M+H]$^+$ calc'd 413.0608, found. 413.0604.

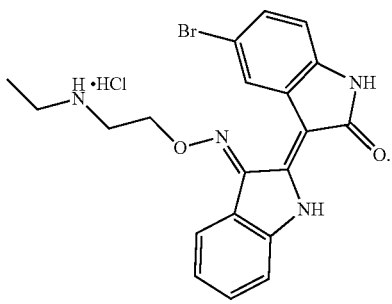 [SMILES: CCNCCO/N=C1/C(=C2/C(=O)Nc3ccc(Br)cc32)Nc2ccccc21]

5IN-1NH1s $^1$H NMR (400 MHz, CDCl$_3$) δ11.71 (b, 1H), 10.95 (b, 1H), 8.90 (b, 2H), 8.76 (d, J=2.0 Hz, 1H), 8.24 (d, J=7.4 Hz, 1H), 7.48-7.36 (m, 2H), 7.30 (dd, J=2.0, 8.2 Hz, 1H), 7.01-7.09 (m, 1H), 6.86 (d, J=8.2 Hz, 1H), 4.83 (t, J=4.8 Hz, 2H), 3.60-3.50 (m, 2H), 2.66 (t, J=5.2 Hz, 3H); $^{13}$C NMR (100 MHz, CDCl$_3$) δ170.9, 152.9, 146.1, 145.1, 138.2, 133.8, 129.7, 128.9, 125.9, 124.8, 122.3, 116.4, 112.9, 112.6, 111.2, 99.8, 72.4, 47.3, 33.4.

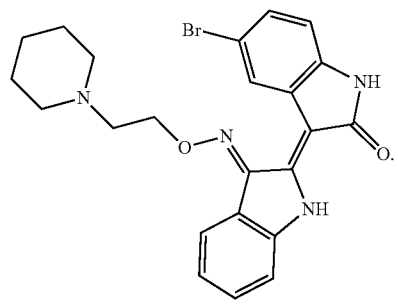

5IN-6NC1

$^1$H NMR (400 MHz, CDCl$_3$) δ11.71 (b, 1H), 10.88 (b, 1H), 8.83 (d, J=2.0 Hz, 1H), 8.15 (d, J=7.8 Hz, 1H), 7.48-7.40 (m, 2H), 7.28 (dd, J=2.0, 8.2 Hz, 1H), 7.09-7.01 (m, 1H), 6.84 (d, J=8.2 Hz, 1H), 4.68 (t, J=5.8 Hz, 2H), 3.40-3.30 (m, 4H), 2.87 (t, J=5.6 Hz, 2H), 1.50-1.40 (m, 4H), 1.40-1.30 (m, 2H); $^{13}$C NMR (100 MHz, CDCl$_3$) δ170.9, 151.8, 145.8, 145.4, 138.0, 133.4, 128.7, 128.6, 125.7, 124.9, 122.4, 116.6, 112.9, 112.6, 111.0, 99.2, 75.1, 57.6, 54.8, 26.1, 24.3; HRMS C$_{23}$H$_{23}$BrN$_4$O$_2$ [M+H]$^+$ calc'd 467.1077, found. 467.1080.

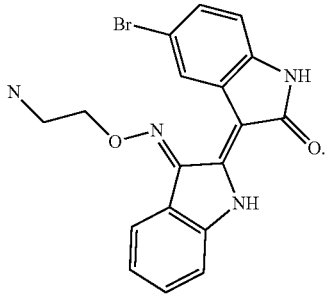

5IN-1NH2

$^1$H NMR (400 MHz, CDCl$_3$) δ11.71 (b, 1H), 10.88 (b, 1H), 8.84 (d, J=2.0 Hz, 1H), 8.14 (d, J=7.8 Hz, 1H), 7.48-7.40 (m, 2H), 7.28 (dd, J=2.0, 8.2 Hz, 1H), 7.09-7.01 (m, 1H), 6.84 (d, J=8.2 Hz, 1H), 4.63 (t, J=5.6 Hz, 2H), 3.12 (t, J=5.6 Hz, 2H), 2.65 (q, J=7.2 Hz, 2H), 1.00 (t, J=7.2 Hz, 3H); $^{13}$C NMR (100 MHz, CDCl$_3$) δ170.9, 151.8, 145.8, 145.5, 138.0, 133.4, 128.8, 128.6, 125.7, 124.9, 122.4, 116.6, 112.9, 112.5, 111.0, 99.2, 76.9, 48.1, 43.9, 15.4; HRMS C$_{20}$H$_{19}$BrN$_4$O$_2$ [M+H]$^+$ calc'd 427.0764, found. 427.0754

4. Example 4:

The kinase assays were performed with recombinant proteins. Briefly, proteins, freshly prepared substrates and $^{33}$P-ATP (specific activity 0.01 μCi/μl final) were mixed in reaction buffer (20 mM HEPES pH 7.5, 10 mM MgCl$_2$, 1 mM EGTA, 0.02% Brij35, 0.02 mg/ml BSA, 0.1 mM Na$_3$VO$_4$, 2 mM DTT) in the presence of DMSO as control or 5IN-1NH1s. The mixtures were reacted for 120 min at room temperature. Samples were transferred onto P81 ion exchange paper and filters were extensively washed with 0.75% phosphoric acid. The radioactivities were monitored. IC$_{50}$ values were determined using GraphPad Prism software.

TABLE 2

| Kinase profiling in vitro for 5IN-1NH1s. | |
|---|---|
| Kinase | IC$_{50}$ (nM) |
| ABL1 | 434 |
| ABL1 (T315I) | 3400 |
| AKT1 | 327 |
| Aurora A | 217 |
| BRAF | 7410 |
| c-MET | >10 |
| c-Src | 13.8 |
| CDK2/cyclin A | 1.08 |
| EGFR | >10 |
| GSK3β | 1.18 |
| IGF1R | 31.8 |
| JAK2 | 169 |

TABLE 2-continued

Kinase profiling in vitro for 5IN-1NH1s.

| Kinase | IC$_{50}$ (nM) |
| --- | --- |
| KDR/vEGFR2 | 245 |
| Mtor/frap1 | >10 |

5. Example 5

The kinase assays were performed with recombinant class III receptor tyrosine kinase family proteins. Briefly, proteins, freshly prepared substrates and $^{33}$P-ATP (specific activity 0.01 μCi/μl final) were mixed in reaction buffer (20 mM HEPES pH 7.5, 10 mM MgCl$_2$, 1 mM EGTA, 0.02% Brij35, 0.02 mg/ml BSA, 0.1 mM Na$_3$VO$_4$, 2 mM DTT) in the presence of DMSO as control or 5IN-1NH1s. The mixtures were reacted for 120 min at room temperature. Samples were transferred onto P81 ion exchange paper and filters were extensively washed with 0.75% phosphoric acid. The radioactivities were monitored. IC$_{50}$ values were determined using GraphPad Prism software. Compound 5IN-1NHls selectively inhibits FLT3 and mutated FLT3 kinases.

TABLE 3

In vitro effects of 5IN-1NH1s on class III receptor tyrosine kinase family.

| Kinase | IC$_{50}$ (nM) |
| --- | --- |
| FLT3 | 1.39 |
| FLT3 (D835Y) | <0.5 |
| FLT3 (ITD) | 1.09 |
| c-Kit | 321 |
| FMS | 16 |
| PDGFR α | 72.2 |
| PDGFR β | 9.1 |

6. Example 6

Figures 5A, 5B:
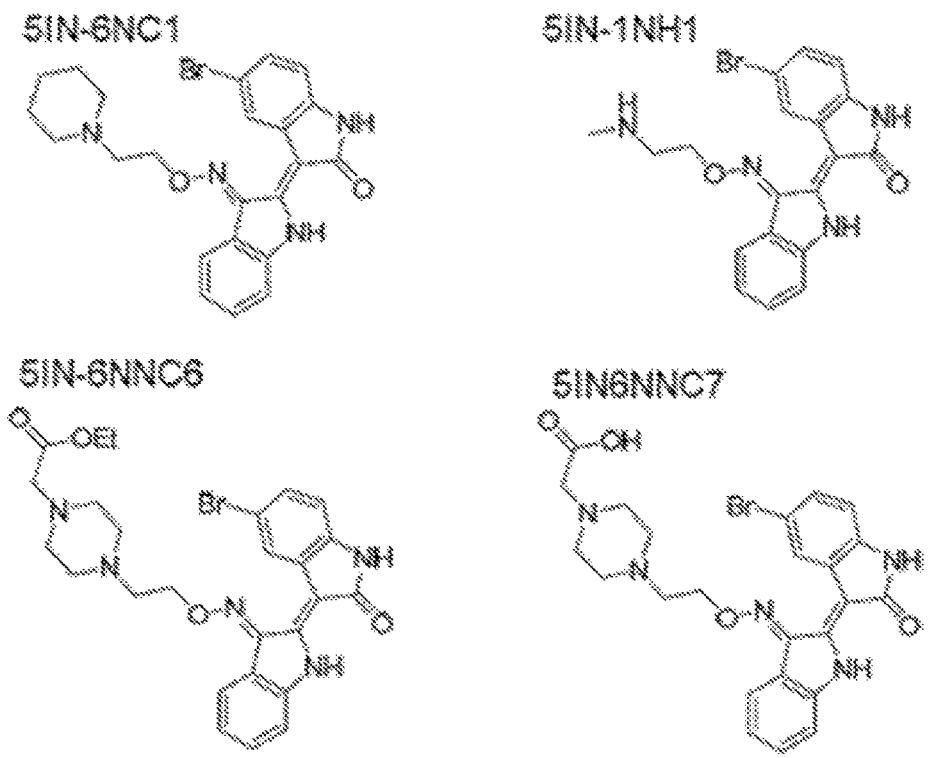
FIGS. 5A-5B: Determination of $IC_{50}$ values of compounds for solid tumor and T315I ABL1 mutant CML cells.
Figure 6A:
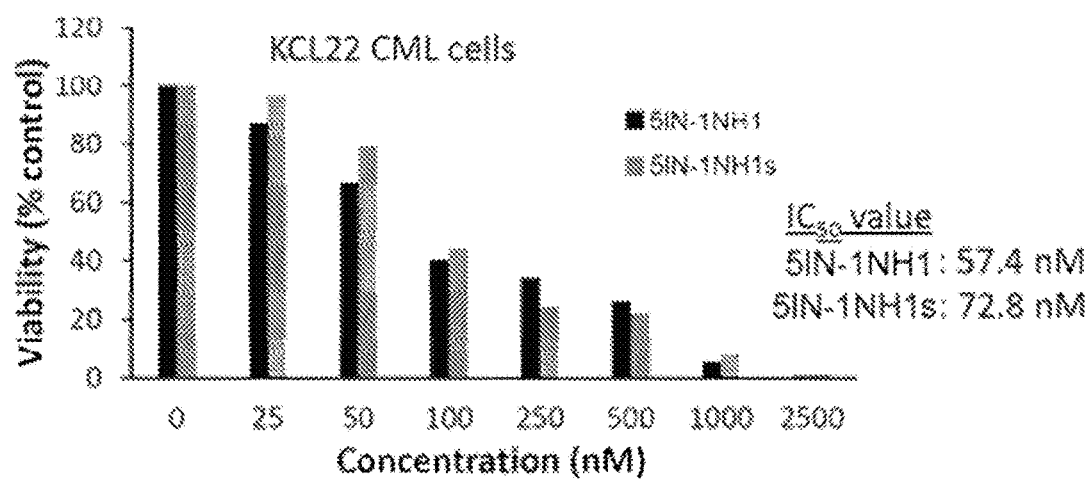
FIGS. 6A-6B: Determination of $IC_{50}$ values of 5IN-1NH1 and 5IN-1NH1s using KCL22 and T315I ABL1 mutant KCL22 CML cells.
Figure 6B:
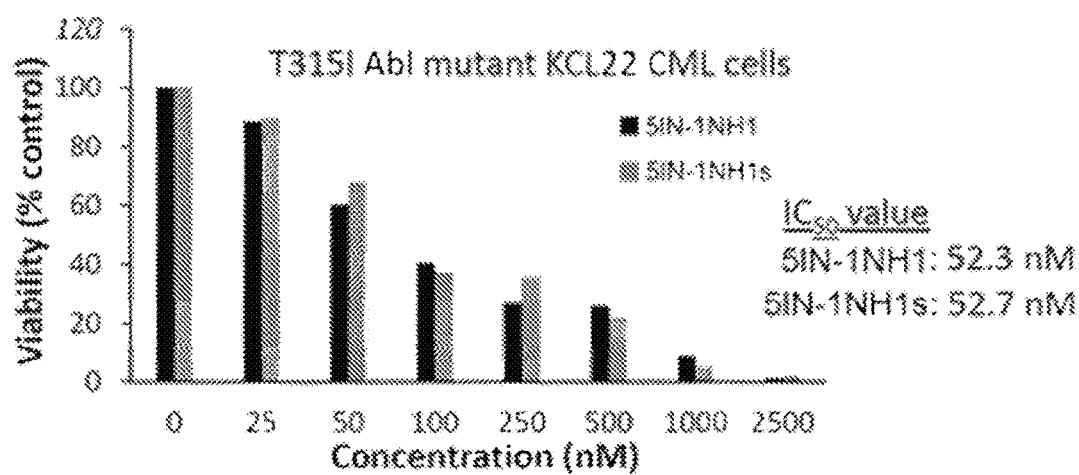
Figure 7A:
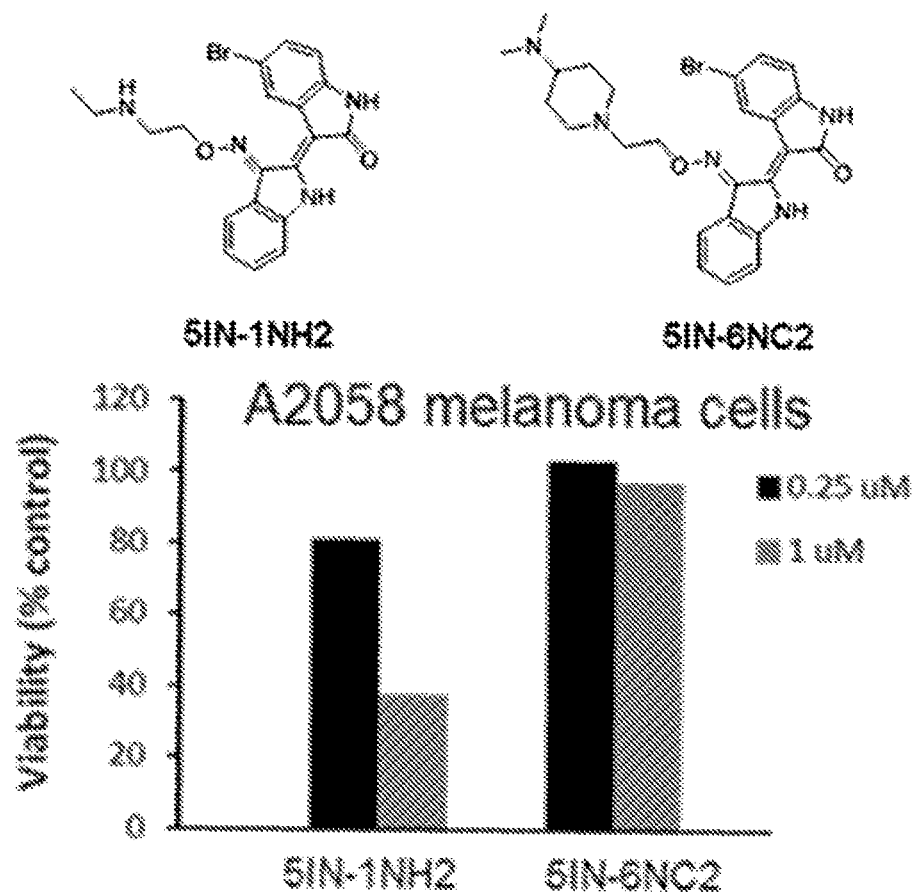
FIGS. 7A-7B: Effects on viability of solid tumor cells (melanoma and prostate cancer) for compounds 5IN-1NH2 and 5IN-6NC2.
Figure 7B:
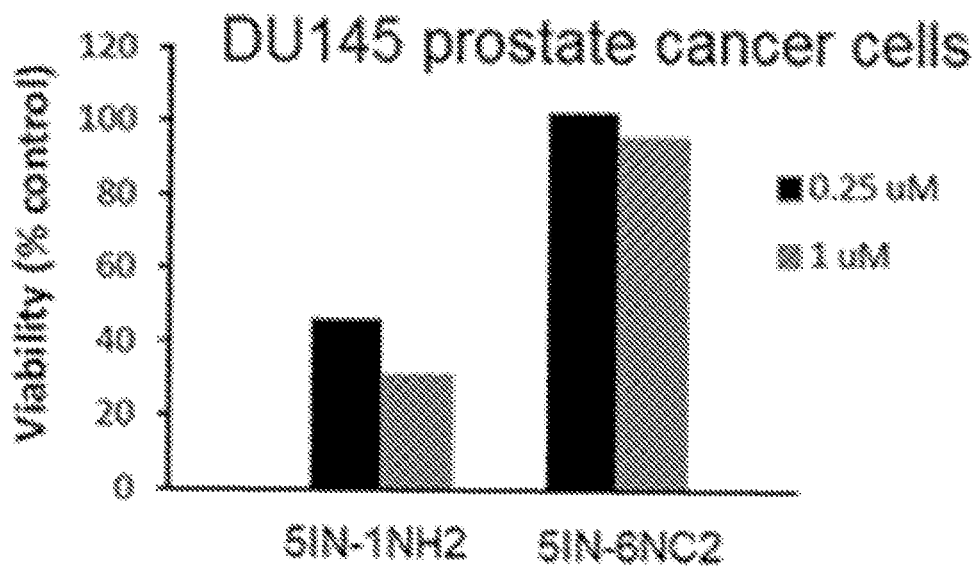

It was discovered and disclosed herein that compounds 5IN-1NH1 and 5IN-1NH1s display considerable potency against T315I ABL1 mutant KCL22 CML cells. See FIG. 5B. In fact, 5IN-1NH1 is around 10-fold more potent against T315I KCL22 CML cells than compound (1289). Current and second generation CML drugs (e.g. imatinib, dasatinib, nilotinib) cannot inhibit T315I mutant ABL1 protein and thus, do not kill this mutant CML cells. Thus, these current therapies are ineffective at treating CML. Thus compounds 5IN-1NH1 and 5IN-1NH2 represent a new class of therapies for the treatment of CML having mutated ABL1 protein.

7. Example 7

MTS assays were performed for cell viability. Human cancer cells were seeded in 96-well plates (2500 cells/well for solid tumors, 5000 cells/well for blood tumors), incubated overnight at 37° C. in 5% CO$_2$, and exposed to 5IN-1NH1 or 5IN-1NHls in a dose-dependent manner for 48 h. See FIGS. 1A-1B, 2A-2B, 3, 4A-4B, and 6A-6B. Dimethyl sulfoxide (DMSO) was used as the vehicle control. Viable cell numbers were determined by tetrazolium conversion to its formazan dye and absorbance was measured at 490 nm using an automated ELISA plate reader. Each experiment was performed in quadruplicate. IC$_{50}$ values were determined using CalcuSyn software (BIO-SOFT®, Cambridge GB).

Human DU145 prostate cancer, A2058 melanoma, SKOV3 ovarian cancer and T315I ABL1 mutant KCL22 CML cells were seeded in 96-well plates (2500 cells/well for solid tumors, 5000 cells/well for blood tumors), incubated overnight at 37° C. in 5% CO$_2$, and exposed to 5IN-6NC1, 5IN-1NH1, 5IN-6NNC6, or 5IN-6NNC7 in a dose-dependent manner for 48 h. See FIG. 5B. Dimethyl sulfoxide (DMSO) was used as the vehicle control. Viable cell numbers were determined by tetrazolium conversion to its formazan dye and absorbance was measured at 490 nm using an automated ELISA plate reader. Each experiment was performed in quadruplicate. IC$_{50}$ values were determined using CalcuSyn software.

MTS assays were performed for cell viability; human A2058 melanoma (FIG. 7A) and DU145 prostate cancer (FIG. 7B) cancer cells (2500/well) were seeded in 96-well plates, incubated overnight at 37° C. in 5% (v/v) CO$_2$ and exposed to 5IN-1NH2 and 5IN-6NC2 at 0.25 uM or 1 uM concentration for 48 h. See FIGS. 7A-7B. DMSO was used as the vehicle control; cell viability was determined by tetrazolium conversion to its formazan dye and absorbance was measured at 490 nm using an automated ELISA plate reader; each experiment was performed in quadruplicate.

Figure 8:
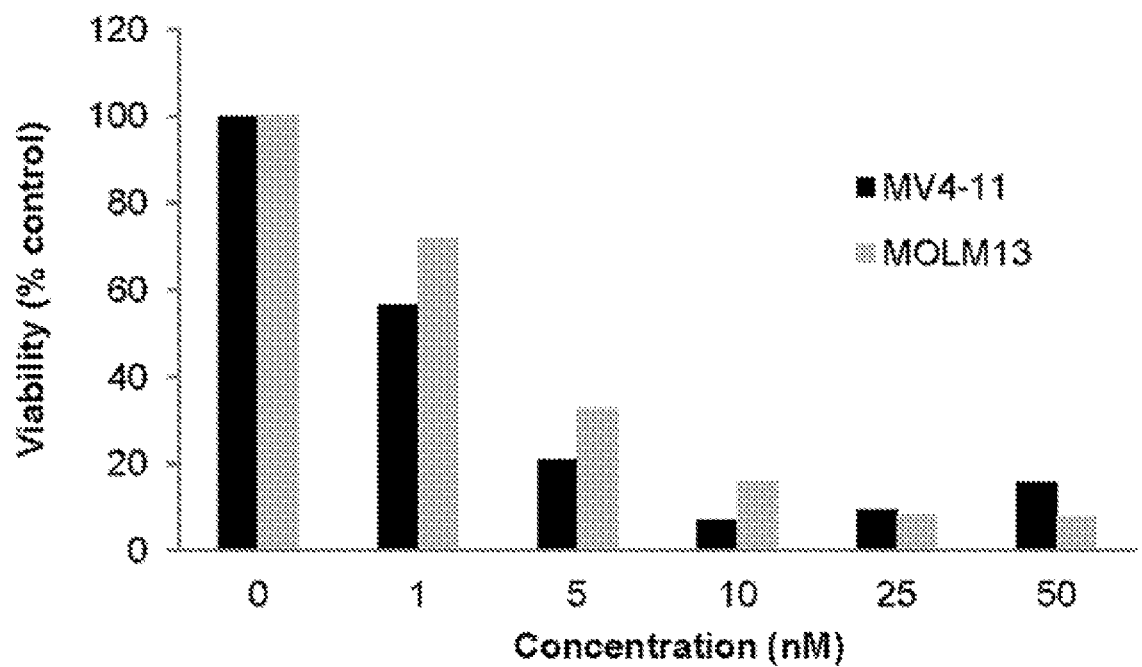
FIG. 8: Compound (1289) [i.e., formula (1289)] inhibits viabilities of MV4-11 and MOLM13 AML cells that harbor an internal tandem duplication (ITD) mutation.

Compound (1289) inhibits viabilities of MV4-11 and MOLM13 AML cells that harbor an internal tandem duplication (ITD) mutation. MTS assays were performed for cell viability. Human MV4-11 and MOLM13 AML cells (5000/well) were seeded in 96-well plates, incubated overnight at 37° C. in 5% CO$_2$, and exposed to compound (1289) in a dose-dependent manner for 48 h. See FIG. 8. Dimethyl sulfoxide (DMSO) was used as the vehicle control. Viable cell numbers were determined by tetrazolium conversion to its formazan dye and absorbance was measured at 490 nm using an automated ELISA plate reader. Each experiment was performed in quadruplicate. IC$_{50}$ values were determined using CalcuSyn software.

Kinase assays were performed with recombinant FLT3, mutated FLT3-ITD and D835I mutant FLT3 kinases. See FIGS. 9A-9C. Briefly, proteins, freshly prepared substrates and $^{33}$P-ATP (specific activity 0.01 μCi/μl final) were mixed in reaction buffer (20 mM HEPES pH 7.5, 10 mM MgCl$_2$, 1 mM EGTA, 0.02% Brij35, 0.02 mg/ml BSA, 0.1 mM Na$_3$VO$_4$, 2 mM DTT) in the presence of DMSO as control or compound (1289). The mixtures were reacted for 120 min at room temperature. Samples were transferred onto P81 ion exchange paper and filters were extensively washed with 0.75% phosphoric acid. The radioactivities were monitored. IC$_{50}$ values were determined using GraphPad Prism software.

Figure 10A:
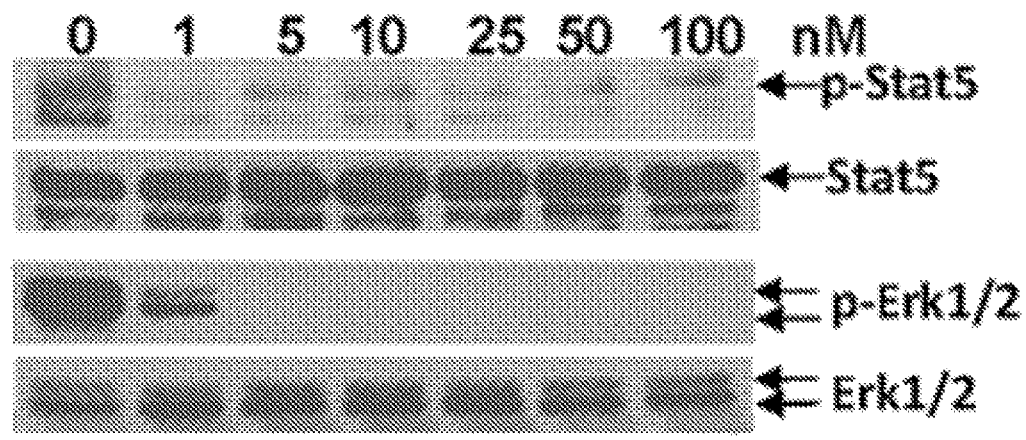
FIGS. 10A-10B: Compound (1289) blocks phosphorylation of signal transducer and activator of transcription 5 (STAT5) and Erk1/2.
Figure 10B:
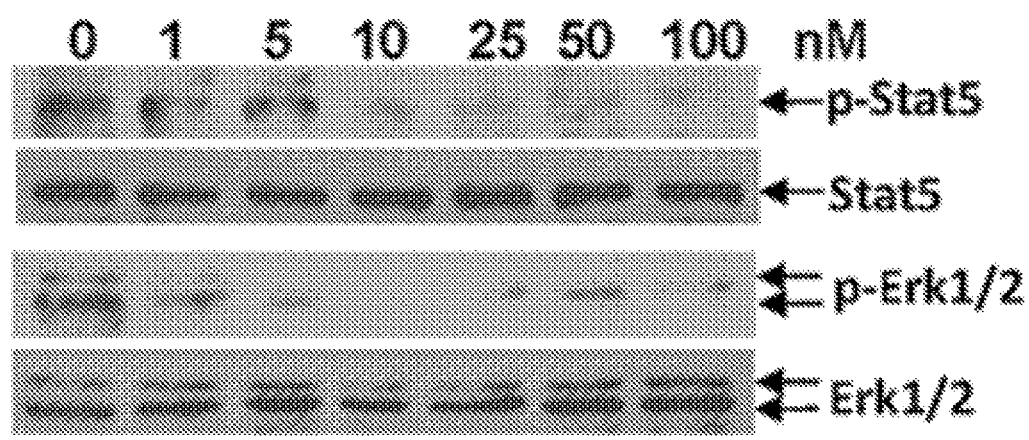

Western blot analyses were performed with specific antibodies. Briefly, human MV4-11 and MOLM13 AML cells were treated with compound (1289) in a dose-dependent manner for 4h. See FIGS. 10A-10B. Whole-cell lysates (40 ug) were resolved by SDS-PAGE. Primary phospho-specific antibodies to p-Stat5 and p-Erk1/3 were diluted in TBS (pH 7.5) with 5% (w/v) BSA and 0.1% (v/v) Tween-20 over night at 4° C. Primary specific antibodies to Stat5 and Erk1/3 were diluted in PBS (pH 7.5) with 5% (w/v) nonfat milk and 0.1% (v/v) Tween-20 overnight at 4° C. Horseradish peroxidase-conjugated secondary antibodies were incubated in PBS (pH 7.5) with 5% (w/v) nonfat milk and 0.1% (v/v) Tween-20 for 1 h at room temperature. Positive immunoreactive proteins were detected using the ECL system.

Figure 11A:
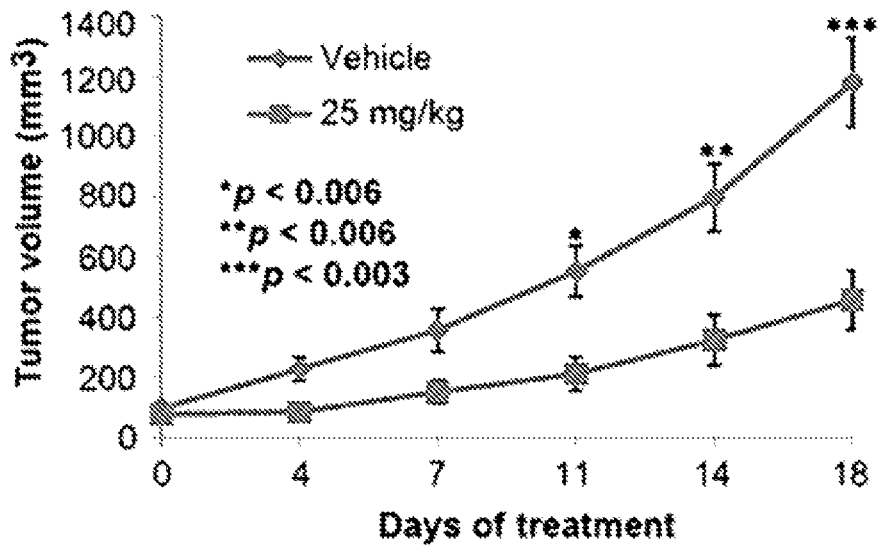
FIGS. 11A-11B.
Figure 11B:
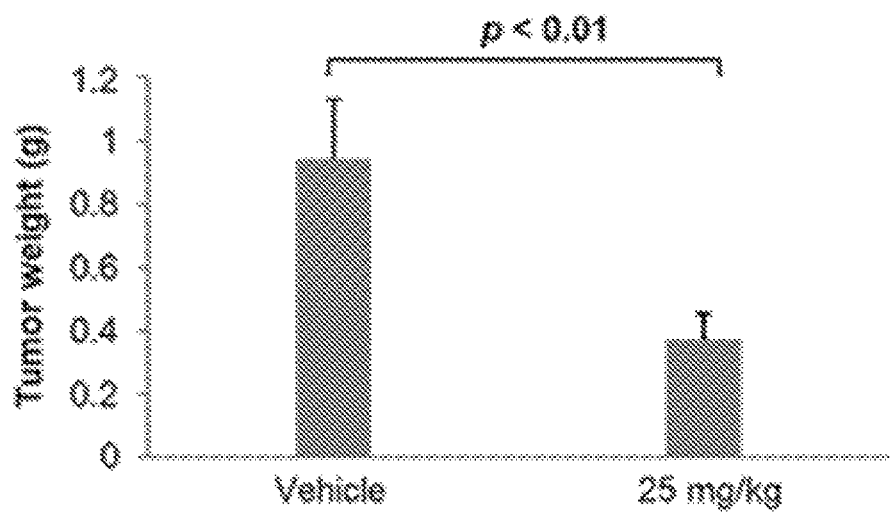

Human MV4-11 AML cells (5×10$^6$) were resuspended in serum-free RPMI1640 medium and subcutaneously injected into the flank of 5-6 weeks old NOD/SCID/ IL-2rg(ko) (NSG) female mouse. When palpable tumor sizes reached at approximately 100 mm³, mice were randomly divided into two groups (vehicle =7, treatment =7). Then, compound (1289) was orally administered at 25 mg/kg with vehicle (10% DMSO +30% SOLUTOL® +60% Saline), twice daily for 18 days. See FIGS. 11A-11B. Tumor volumes were calculated by the formula 1/2a×b², where a is the long diameter, and b is the short diameter. Tumor volumes correlate with tumor weights. The statistical significance of group differences was analyzed using a Student's t-test with the two-tailed distribution. P values less than 0.05 were considered statistically significant.

VI. EMBODIMENTS

Embodiments disclosed herein include the following.

Embodiment 1. A compound having formula:

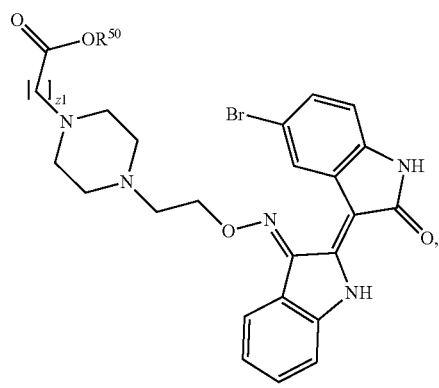

(III)

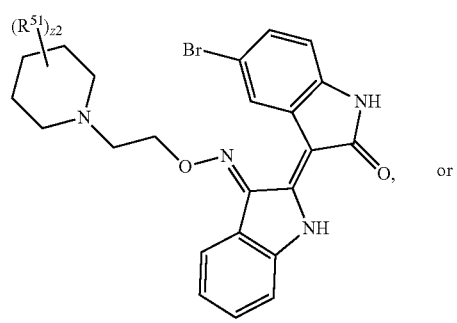

(IV)

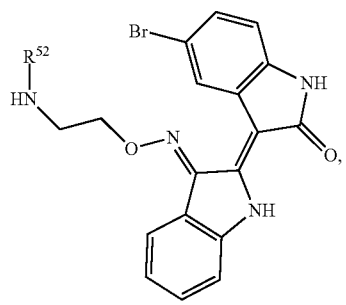

(V)

wherein $R^{50}$ is hydrogen, oxo, halogen, —CF$_3$, —CN, —OH, —NH$_2$, —COOH, —CH$_2$COOH, —CONH$_2$, —NO$_2$, —SH, —OCF$_3$, —OCHF$_2$, or unsubstituted alkyl; $R^{51}$ is hydrogen, oxo, halogen, —CF$_3$, —CN, —OH, —NR$^{51A}$R$^{51B}$, —COOH, —CH$_2$COOH, —CONH$_2$, —NO$_2$, —SH, —OCF$_3$, —OCHF$_2$, unsubstituted alkyl, or unsubstituted heteroalkyl; $R^{51A}$ and $R^{51B}$ are independently hydrogen or unsubstituted alkyl; $R^{52}$ is halogen, —CF$_3$, —CN, —OH, —NH$_2$, —COOH, —CONH$_2$, or unsubstituted alkyl; z1 and z2 are independently 0, 1, 2, 3, 4, or 5, including pharmaceutically acceptable salts thereof.

Embodiment 2. The compound of embodiment 1, wherein $R^{50}$ is hydrogen or unsubstituted alkyl.

Embodiment 3. The compound of any one of embodiments 1 to 2, wherein $R^{50}$ is hydrogen or unsubstituted $C_1$-$C_5$ alkyl.

Embodiment 4. The compound of any one of embodiments 1 to 3, wherein $R^{50}$ is hydrogen, methyl, ethyl, or propyl.

Embodiment 5. The compound of any one of embodiments 1 to 4, wherein z1 is 1 or 2.

Embodiment 6. The compound of any one of embodiments 1 to 5, wherein $R^{51}$ is hydrogen, oxo, halogen, —CF$_3$, —CN, —OH, —NH$_2$, —COOH, —CH$_2$COOH, —CONH$_2$, —NO$_2$, or unsubstituted alkyl.

Embodiment 7. The compound of any one of embodiments 1 to 6, wherein $R^{51}$ is —CH$_2$COOH, unsubstituted alkyl or unsubstituted heteroalkyl.

Embodiment 8. The compound of any one of embodiments 1 to 7, wherein $R^{51}$ is —CH$_2$COOH, unsubstituted $C_1$-$C_5$ alkyl or unsubstituted 2 to 6 membered heteroalkyl.

Embodiment 9. The compound of any one of embodiments 1 to 8, wherein z2 is 0, 1, or 2.

Embodiment 10. The compound of any one of embodiments 1 to 9, wherein $R^{52}$ is halogen, —OH, —NH$_2$, —COOH, —CONH$_2$, or unsubstituted alkyl.

Embodiment 11. The compound of any one of embodiments 1 to 10, wherein $R^{52}$ is unsubstituted alkyl.

Embodiment 12. The compound of any one of embodiments 1 to 11, wherein $R^{52}$ is unsubstituted $C_1$-$C_5$ alkyl.

Embodiment 13. The compound of any one of embodiments 1 to 10, wherein $R^{52}$ is —NR$^{51A}$R$^{51B}$, wherein $R^{51A}$ and $R^{51B}$ are independently unsubstituted $C_1$-$C_5$ alkyl.

Embodiment 14. The compound of any one of embodiments 1 to 13, wherein said compound has the formula:

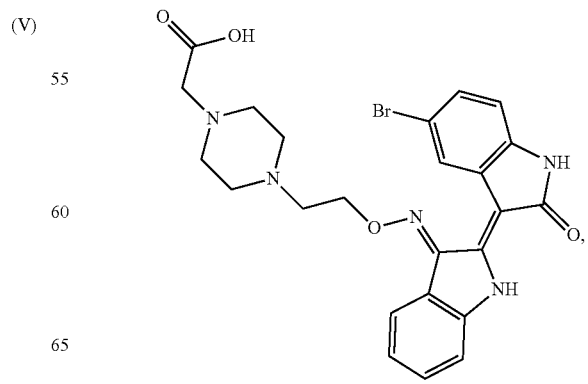

-continued
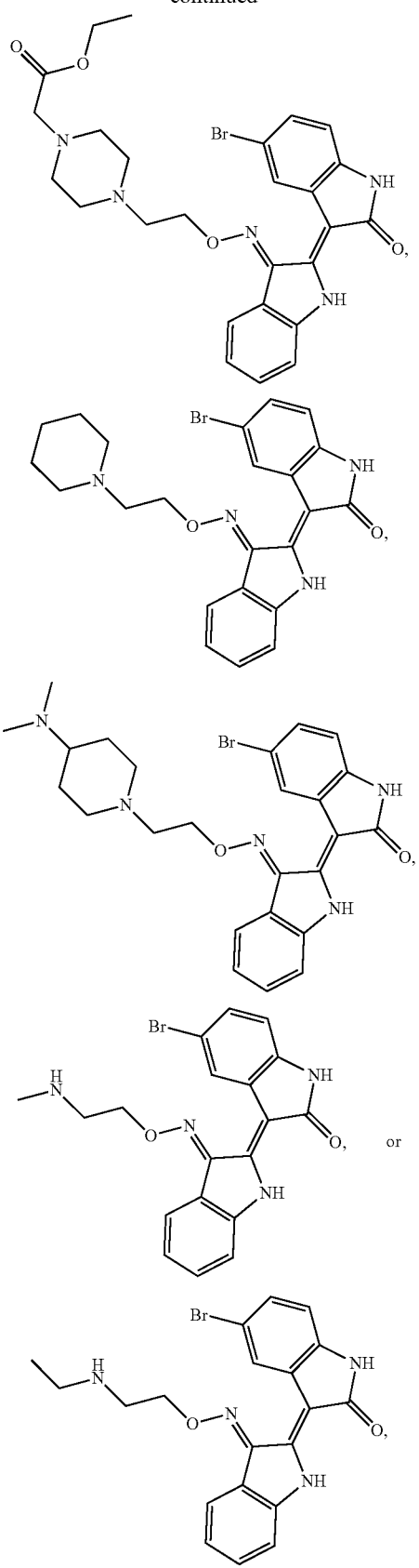
including pharmaceutically acceptable salts thereof.
Embodiment 15. A method of treating cancer, said method comprising administering to a subject in need thereof an effective amount of a compound of one of embodiments 1 to 14.
Embodiment 16. The method of embodiment 15, wherein said compound has the formula:
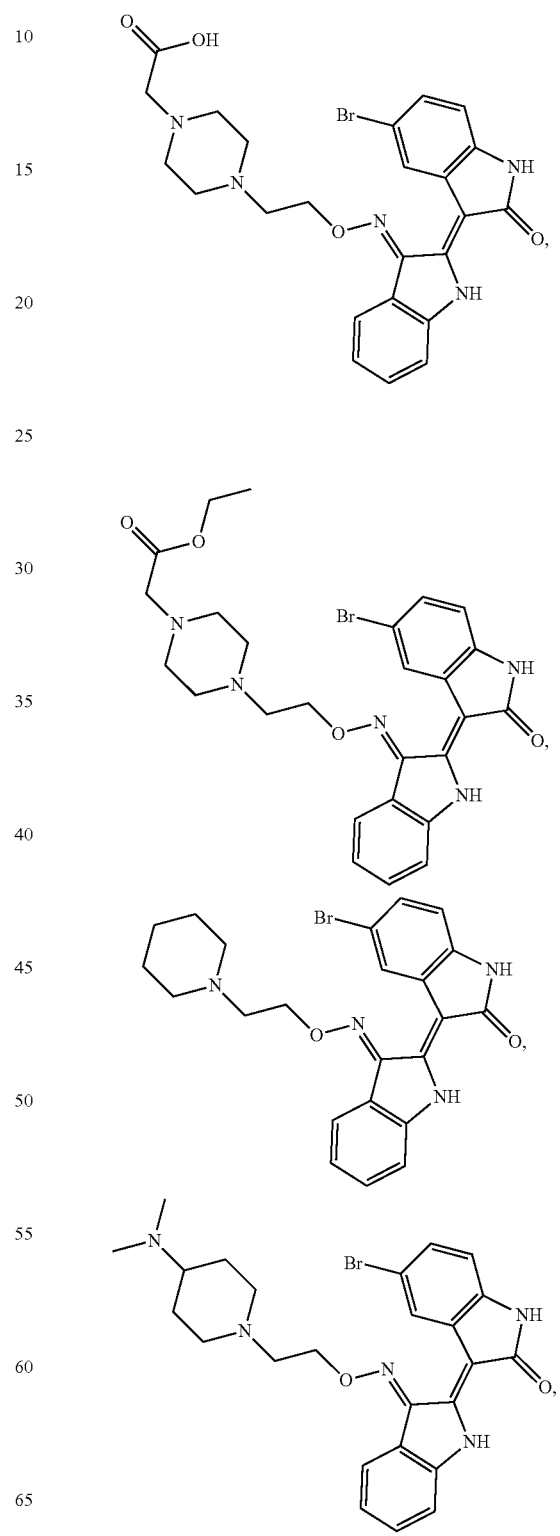

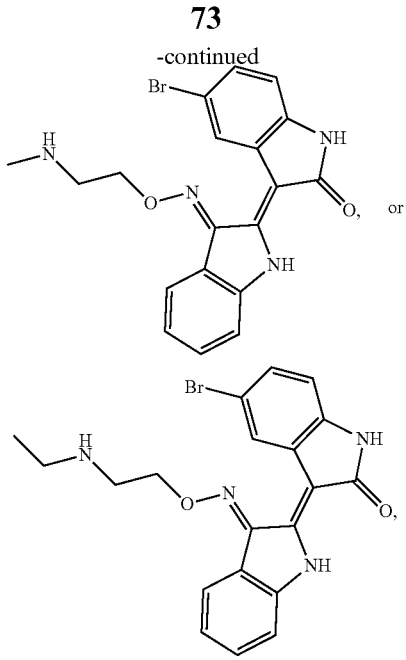

including pharmaceutically acceptable salts thereof

Embodiment 17. The method of any one of embodiments 15 to 16, wherein said cancer is cancer is lung cancer, breast cancer, ovarian cancer, leukemia, lymphoma, melanoma, pancreatic cancer, sarcoma, bladder cancer, bone cancer, brain cancer, cervical cancer, colon cancer, esophageal cancer, gastric cancer, liver cancer, head and neck cancer, kidney cancer, myeloma, thyroid cancer, or prostate cancer.

Embodiment 16. The method of any one of embodiments 15 to 17, further comprising co-administering an effective amount of an anti-cancer agent.

Embodiment 19. A method of treating CML expressing an ABL1-kinase, said method comprising administering an effective amount of a compound of one of embodiments 1 to 14.

Embodiment 20. The method of embodiment 19, wherein said ABL1-kinase is a ABL1 mutant-kinase.

Embodiment 21. The method of any one of embodiments 19 to 20, wherein said ABL1 mutant-kinase is a BCR-ABL1 mutant kinase.

Embodiment 22. The method of embodiment 21, wherein said BCR-ABL1 mutant kinase comprises a mutation of an amino acid residue corresponding to Y253, E255, V268, V270, T272, Y274, D276, T277, M278, E282, F283, A288, M290, K291, E292, I293, P296, L298, V299, Q300, G303, V304, C305, T306, F311, I314, T315, E316, F317, M318, Y320, G321, D325, Y326, L327, R328, E329, Q333, E334, A337, V339, L342, M343, A344, I347, A350, M351, E352, E355, K357, N358, F359, I360, L364, E373, N374, K378, V379, A380, D381, F382, T389, T392, T394, A395, H396, A399, P402, or T406 of SEQ ID NO:2 or SEQ ID NO:3.

Embodiment 23. The method of embodiment 22, wherein said BCR-ABL1 mutant kinase comprises a mutation of an amino acid residue corresponding to T315 of SEQ ID NO:2 or SEQ ID NO:3.

Embodiment 24. The method of embodiment 23, wherein said mutation is a T315I or T315A mutation.

Embodiment 25. A method of treating acute myeloid leukemia expressing a . FLT3-kinase in a subject in need thereof, said method comprising administering an effective amount of a compound having the formula:

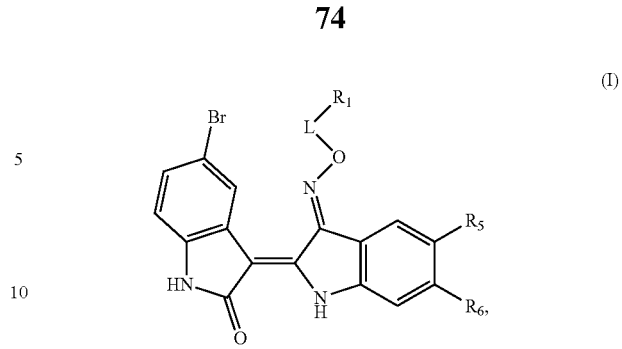

wherein, L is a bond or substituted or unsubstituted alkylene; $R^1$ is hydrogen, halogen, —$CF_3$, —$CCl_3$, —$CBr_3$, —$CI_3$, —$OCF_3$, —$OCCl_3$, —$OCBr_3$, —$OCI_3$, —CN, —OH, —$NH_2$, —$C(O)OR^4$, —$CONH_2$, —$NO_2$, —SH, —$NHNH_2$, —$NR^2R^3$, —$OR^4$, —$SR^4$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; $R^2$ and $R^3$ are independently substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, wherein $R^2$ and $R^3$ are optionally joined together to form a substituted or unsubstituted heterocycloalkyl or substituted or unsubstituted heteroaryl; $R^4$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; $R^5$ and $R^6$ are independently hydrogen, halogen, —$CF_3$, —$CCl_3$, —$CBr_3$, —$CI_3$, —$OCF_3$, —$OCCl_3$, —$OCBr_3$, —$OCI_3$, —CN, —OH, —$NH_2$, —C(O)OH, —$C(O)OR^9$, —$CONH_2$, —$NO_2$, —SH, —$NHNH_2$, —$NR^7R^8$, —$OR^9$, —$SR^9$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; $R^7$ and $R^8$ are independently substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, wherein $R^7$ and $R^8$ are optionally joined together to form a substituted or unsubstituted heterocycloalkyl or substituted or unsubstituted heteroaryl; and $R^9$ is substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, including pharmaceutically acceptable salts thereof, thereby treating said acute myeloid leukemia.

Embodiment 26. The method of embodiment 25, wherein $R^5$ and $R^6$ are hydrogen.

Embodiment 27. The method of any one of embodiments 25 to 26, wherein L is unsubstituted alkylene.

Embodiment 28. The method of any one of embodiments 25 to 27, wherein L is unsubstituted $C_2$ alkylene.

Embodiment 29. The method of embodiment 25, wherein L is a bond.

Embodiment 30. The method of any one of embodiments 25 to 29, wherein $R^1$ is halogen, —$CF_3$, —$CCl_3$, —$CBr_3$, —$CI_3$, —$OCF_3$, —$OCCl_3$, —$OCBr_3$, —$OCI_3$, —CN, —OH, —NH₂, —COOH, —C(O)OR⁴, —CONH₂, —NO₂, —SH, —NHNH₂, —NR²R³, —OR⁴, —SR⁴, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Embodiment 31. The method of any one of embodiments 25 to 30, wherein R¹ is —NR²R³.

Embodiment 32. The method of any one of embodiments 25 to 31, wherein R² and R³ are independently substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Embodiment 33. The method of any one of embodiments 25 to 32, wherein R² and R³ are independently substituted or unsubstituted alkyl.

Embodiment 34. The method of any one of embodiments 25 to 33, wherein R² and R³ are independently substituted or unsubstituted C₁-C₈ alkyl.

Embodiment 35. The method of any one of embodiments 25 to 34, wherein R² and R³ are independently substituted or unsubstituted C₁-C₄ alkyl.

Embodiment 36. The method of any one of embodiments 25 to 31, wherein R² and R³ are joined together to form a substituted or unsubstituted heterocycloalkyl or substituted or unsubstituted heteroaryl.

Embodiment 37. The method of embodiment 36, wherein R² and R³ are joined together to form a substituted or unsubstituted heterocycloalkyl.

Embodiment 38. The method of embodiment 37, wherein R² and R³ are joined together to form a substituted or a substituted unsubstituted C₅-C₇ heterocycloalkyl.

Embodiment 39. The method of embodiment 36, wherein R² and R³ are joined together to form a substituted or unsubstituted pyrrolidinyl.

Embodiment 40. The method of embodiment 36, wherein R² and R³ are joined together to form a substituted or unsubstituted piperazinyl.

Embodiment 41. The method of embodiment 25 wherein said compound has the formula:

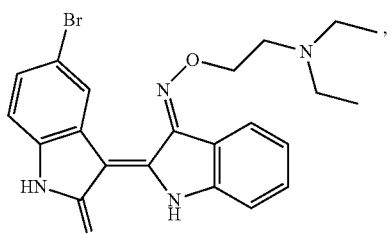

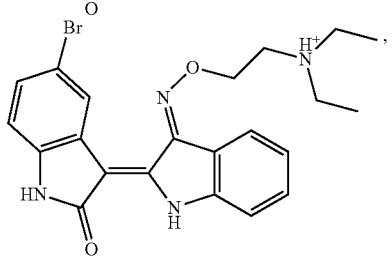

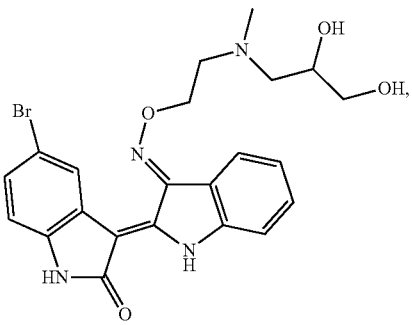

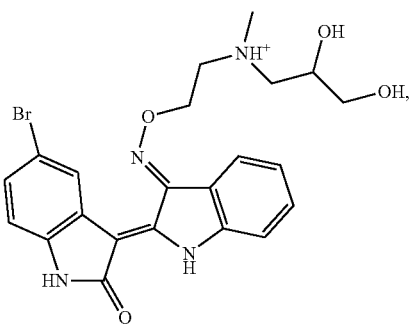

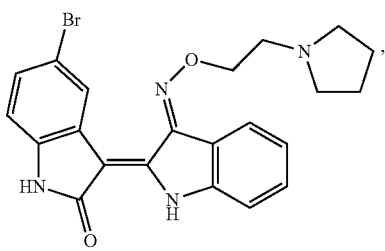

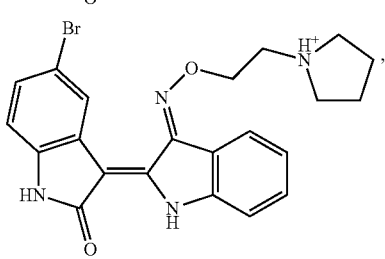

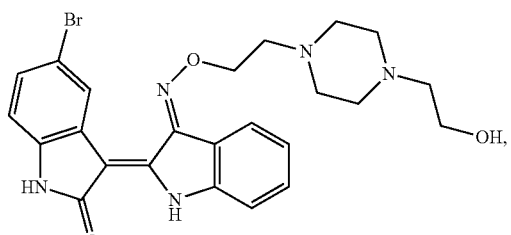

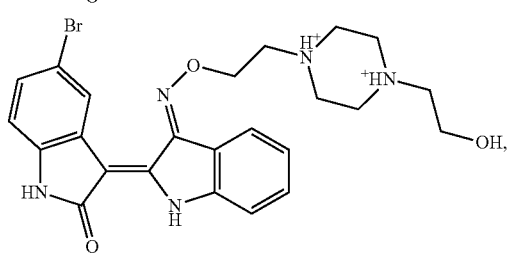

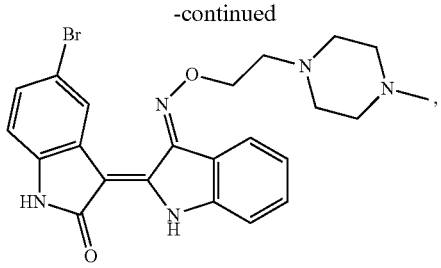
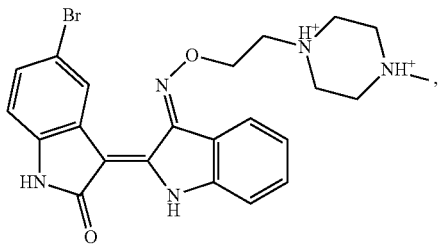
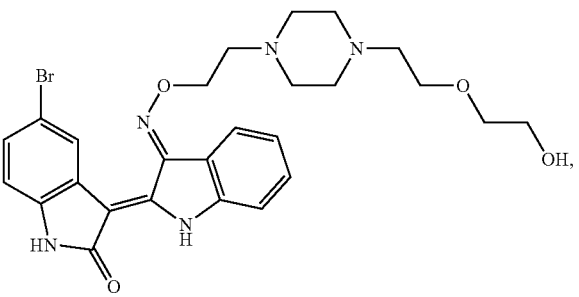
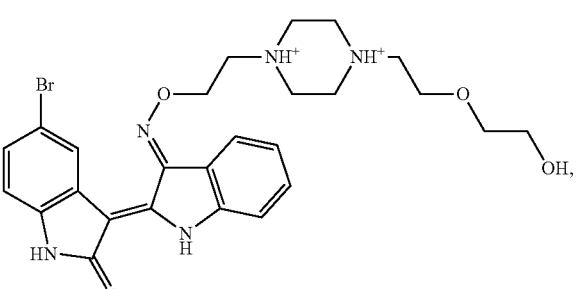
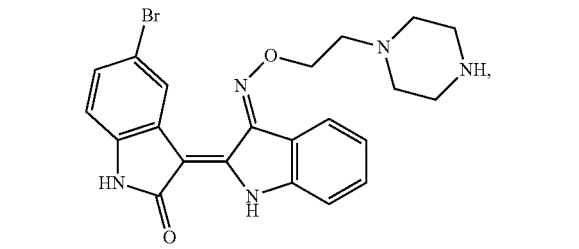
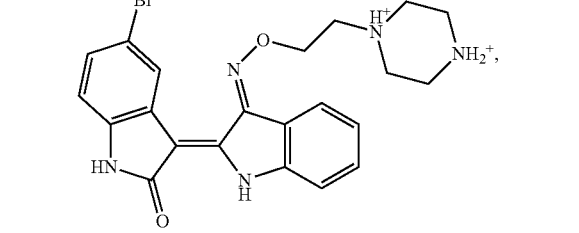
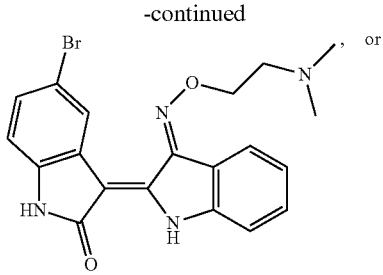
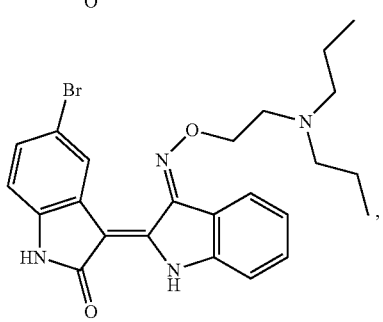
including pharmaceutical salts thereof.
Embodiment 42. The compound of embodiment 25 wherein said compound has the formula:
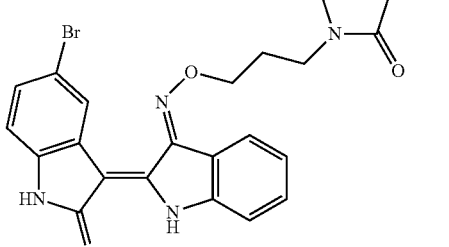
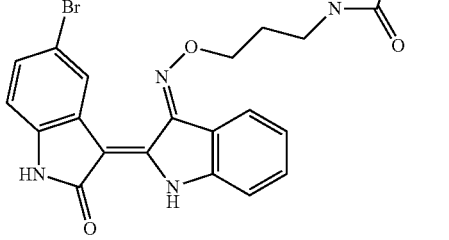
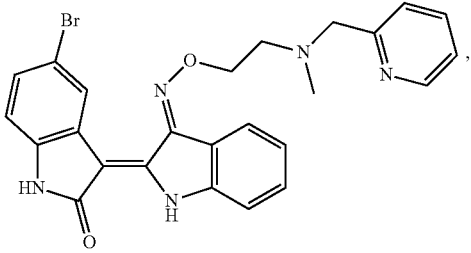

-continued

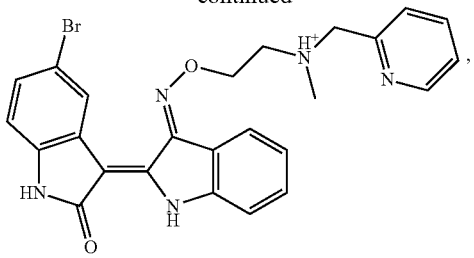

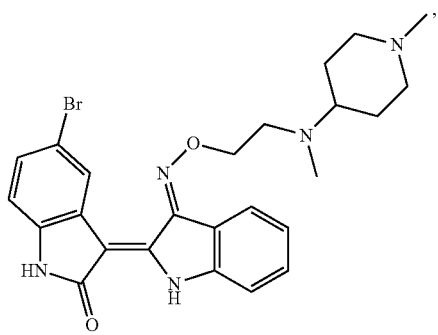

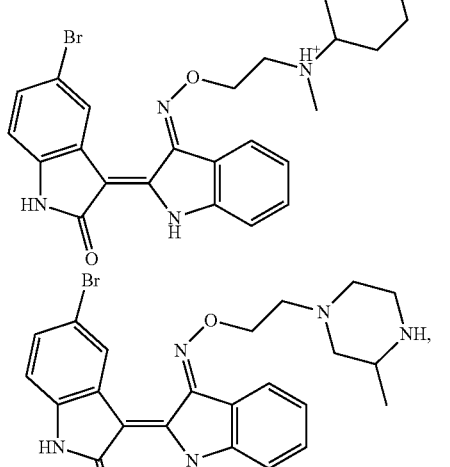

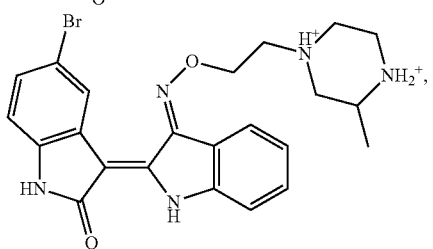

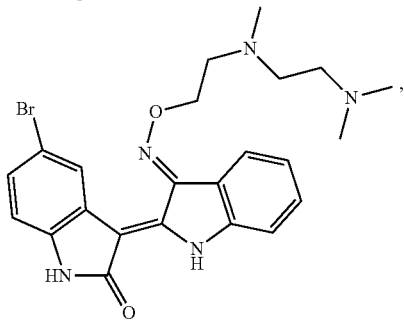

-continued

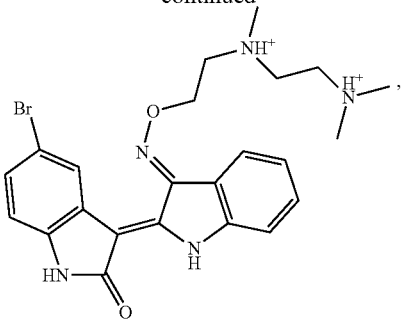

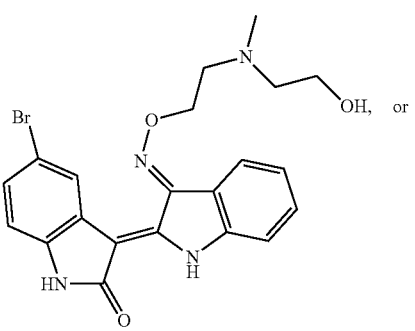

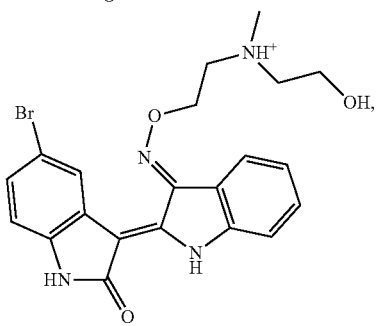

including pharmaceutical salts thereof

Embodiment 43. A method of treating acute myeloid leukemia expressing a FLT3-kinase in a subject in need thereof, said method comprising administering an effective amount of a compound according to embodiments 1 to 14, thereby treating said acute myeloid leukemia.

Embodiment 44. The method of embodiment 43, wherein said compound has the formula:

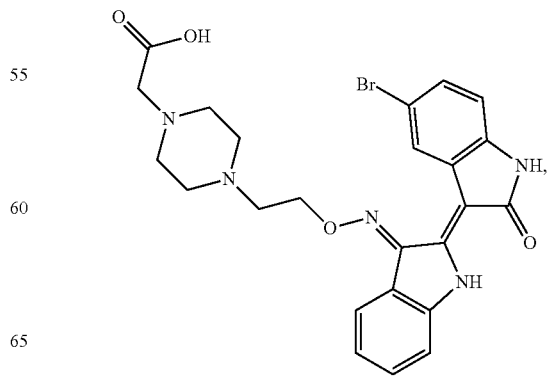

-continued

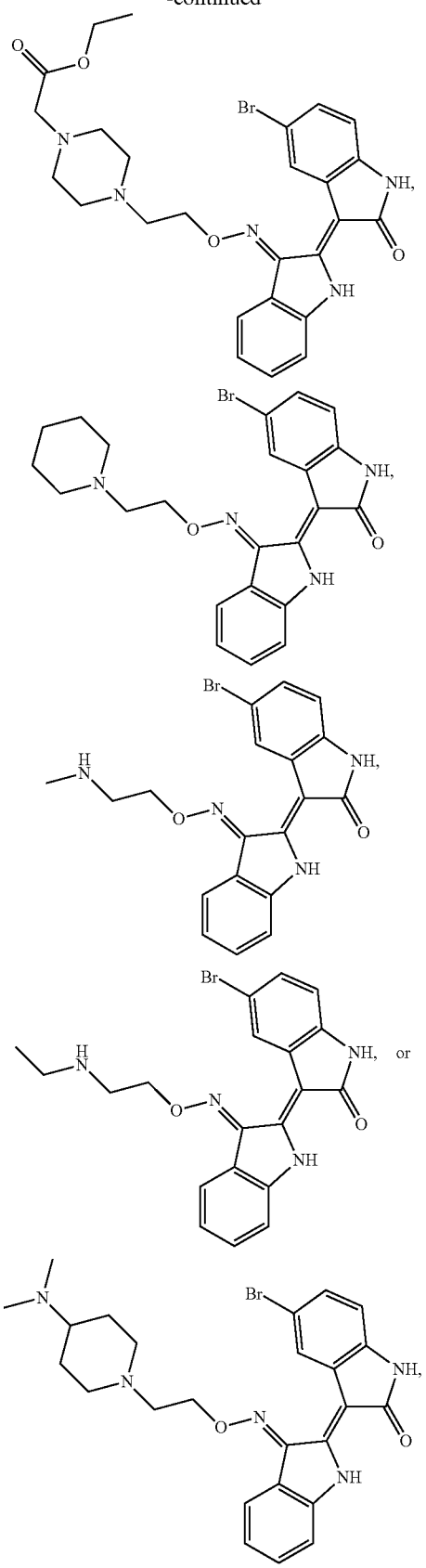

including pharmaceutically acceptable salts thereof

Embodiment 45. The method of any one of embodiments 43 to 44, wherein said compound has the formula:

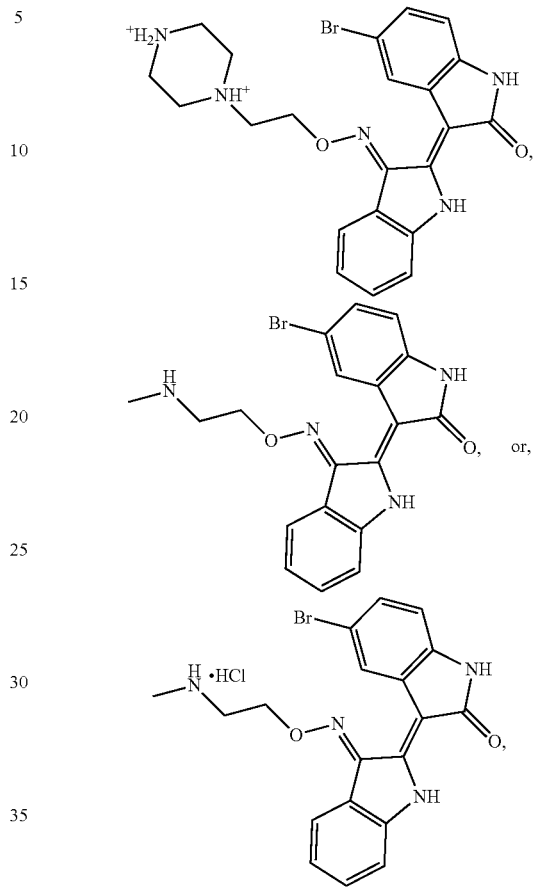

including pharmaceutically acceptable salts thereof.

Embodiment 46. The method of any one of embodiments 25 to 45, wherein said FLT3-kinase is a FLT3-mutant kinase.

Embodiment 47. The method of embodiment 46, wherein said FLT3-mutant kinase is a FLT3-TKD mutant kinase.

Embodiment 48. The method of embodiment 47, wherein said FLT3-TKD mutant kinase comprises a mutation at an amino acid residue position corresponding to D835, I836, D839, S840, N841, or Y842 of SEQ ID NO:1.

Embodiment 49. The method of embodiment 46, wherein said FLT3-mutant kinase comprises a FLT3-ITD mutant kinase.

Embodiment 50. The method of embodiment 49, wherein said FLT3-ITD mutant kinase further comprises a mutation at an amino acid residue position corresponding to D835, I836, D839, S840, N841, or Y842 of SEQ ID NO:1.

Embodiment 51. The method of any one of embodiments 46 to 50, wherein said FLT3-mutant kinase is tyrosine kinase-inhibitor resistant.

Embodiment 52. The method of any one of embodiments 46 to 51, wherein said FLT3-mutant kinase is AC220 drug resistant.

Embodiment 53. The method of any one of embodiments 25 to 52, comprising co-administering an effective amount of an anti-cancer agent.

Embodiment 54. A method of modulating activity of a FLT3-kinase, said method comprising contacting a FLT3-kinase with a compound having formula:

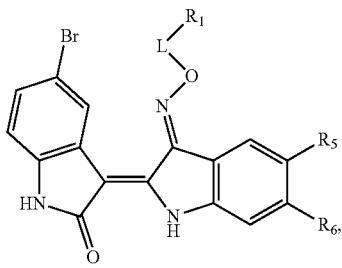

(I)

wherein, L is a bond or substituted or unsubstituted alkylene; $R^1$ is hydrogen, halogen, —$CF_3$, —$CCl_3$, —$CBr_3$, —$CI_3$, —$OCF_3$, —$OCCl_3$, —$OCBr_3$, —$OCI_3$, —CN, —OH, —$NH_2$, —$C(O)OR^4$, —$CONH_2$, —$NO_2$, —SH, —$NHNH_2$, —$NR^2R^3$, —$OR^4$, —$SR^4$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; $R^2$ and $R^3$ are independently substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, wherein $R^2$ and $R^3$ are optionally joined together to form a substituted or unsubstituted heterocycloalkyl or substituted or unsubstituted heteroaryl; $R^4$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; $R^5$ and $R^6$ are independently hydrogen, halogen, —$CF_3$, —$CCl_3$, —$CBr_3$, —$CI_3$, —$OCF_3$, —$OCCl_3$, —$OCBr_3$, —$OCI_3$, —CN, —OH, —$NH_2$, —C(O)OH, —$C(O)OR^9$, —$CONH_2$, —$NO_2$, —SH, —$NHNH_2$, —$NR^7R^8$, —$OR^9$, —$SR^9$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; $R^7$ and $R^8$ are independently substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, wherein $R^7$ and $R^8$ are optionally joined together to form a substituted or unsubstituted heterocycloalkyl or substituted or unsubstituted heteroaryl; and $R^9$ is substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, including pharmaceutically acceptable salts thereof, thereby modulating said activity of said FLT3-kinase.

Embodiment 55. A method of modulating activity of a FLT3-kinase, said method comprising contacting a FLT3-kinase with a compound according to embodiments to 14, thereby modulating said activity of said FLT3-kinase.

Embodiment 56. The method of any one of embodiments 54 to 55, wherein said compound has the formula:

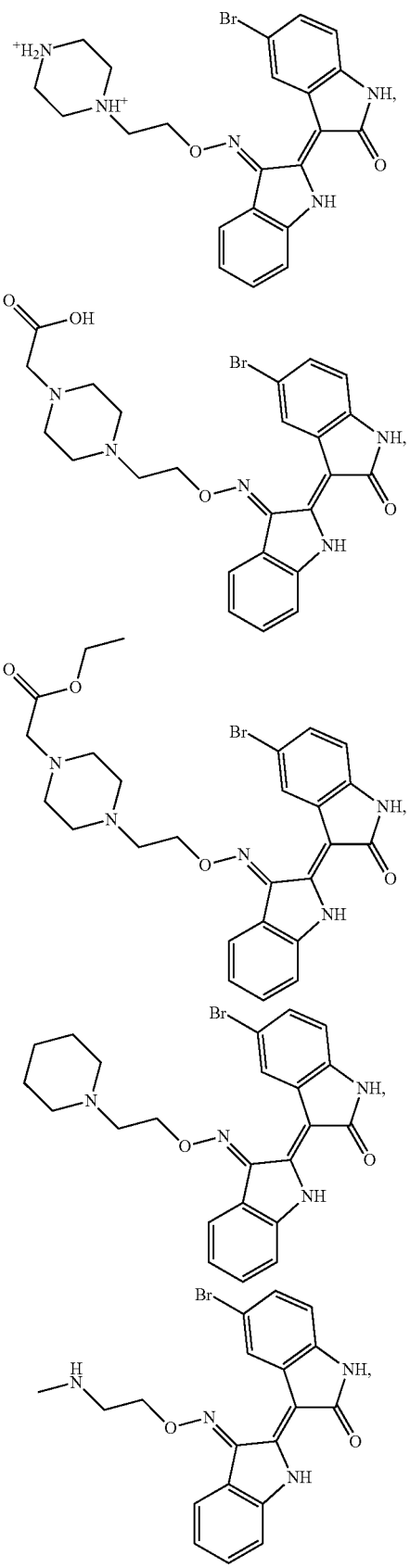

-continued

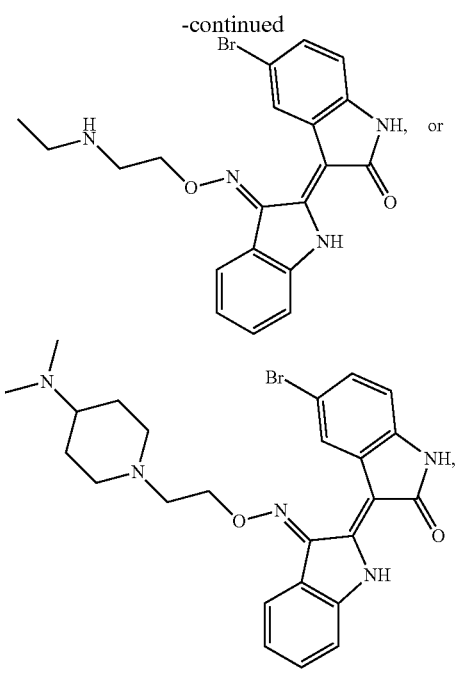

including pharmaceutically acceptable salts thereof.

Embodiment 57. The method of any one of embodiments 54 to 56, wherein said FLT3-kinase is a FLT3-mutant kinase.

Embodiment 58. The method of embodiment 57, wherein said FLT3-mutant kinase is a FLT3-TKD mutant kinase.

Embodiment 59. The method embodiment 58, wherein said FLT3-TKD mutant kinase comprises a mutation at an amino acid residue position corresponding to D835, I836, D839, S840, N841, or Y842 of SEQ ID NO:1.

Embodiment 60. The method of embodiment 57, wherein said FLT3-kinase is a FLT3-ITD mutant kinase.

Embodiment 61. The method of embodiment 60, wherein said FLT3-ITD mutant kinase further comprises a mutation at an amino acid residue position corresponding to D835, I836, D839, S840, N841, or Y842 of SEQ ID NO:1.

Embodiment 62. The method of any one of embodiments 54 to 61, wherein said contacting decreases the activity of said FLT3-kinase.

Embodiment 63. The method of any one of embodiments 54 to 62, wherein said method further comprises modulating STAT signaling, STAT3, STAT5, MAP kinase signaling, or AKT signaling.

Embodiment 64. The method of any one of embodiments 25 to 63, wherein said compound is administered as a pharmaceutical composition.

Embodiment 65. The method of any one of embodiments 25 to 64, wherein said pharmaceutical composition comprises a pharmaceutically acceptable excipient.

What is claimed is:

1. A compound having formula:

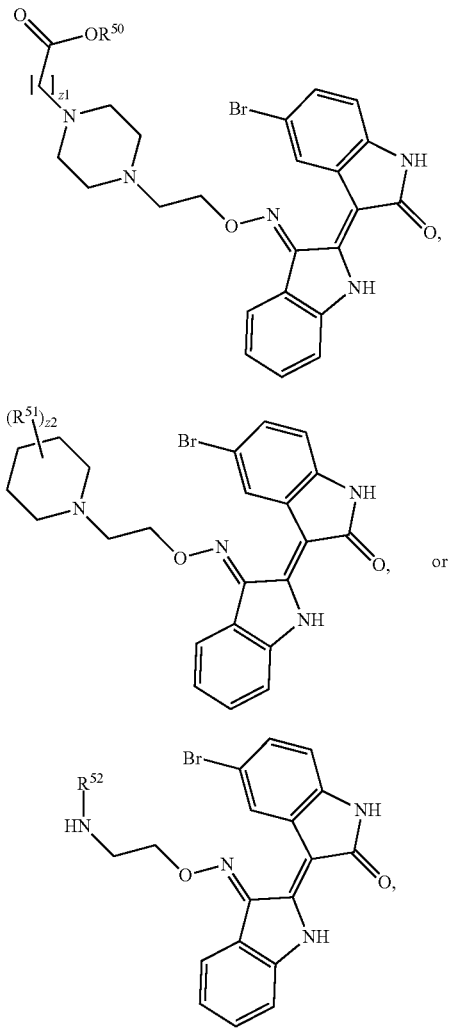

wherein
- $R^{50}$ is hydrogen, oxo, halogen, —$CF_3$, —CN, —OH, —$NH_2$, —COOH, —$CH_2COOH$, —$CONH_2$, —$NO_2$, —SH, —$OCF_3$, —$OCHF_2$, or unsubstituted alkyl;
- $R^{51}$ is hydrogen, oxo, halogen, —$CF_3$, —CN, —OH, —$NR^{51A}R^{51B}$ —COOH, —$CH_2COOH$, —$CONH_2$, —$NO_2$, —SH, —$OCF_3$, —$OCHF_2$, unsubstituted alkyl, or unsubstituted heteroalkyl;
- $R^{51A}$ and $R^{51B}$ are independently hydrogen or unsubstituted alkyl;
- $R^{52}$ is halogen, —$CF_3$, —CN, —OH, —$NH_2$, —COOH, —$CONH_2$, or unsubstituted alkyl;
- z1 and z2 are independently 0, 1, 2, 3, 4, or 5, or a pharmaceutically acceptable salt thereof.

2. The compound of claim 1, wherein $R^{50}$ is hydrogen or unsubstituted alkyl.

3. The compound of claim 2, wherein $R^{50}$ is hydrogen or unsubstituted $C_1$-$C_5$ alkyl.

4. The compound of claim 3, wherein $R^{50}$ is hydrogen, methyl, ethyl, or propyl.

5. The compound of claim 1, wherein z1 is 1 or 2.

6. The compound of claim 1, wherein $R^{51}$ is hydrogen, oxo, halogen, —$CF_3$, —CN, —OH, —$NH_2$, —COOH, —$CH_2COOH$, —$CONH_2$, —$NO_2$, or unsubstituted alkyl.

7. The compound of claim 6, wherein $R^{51}$ is —$CH_2COOH$, unsubstituted alkyl or unsubstituted heteroalkyl.

8. The compound of claim 1, wherein $R^{51}$ is —$CH_2COOH$, unsubstituted $C_1$-$C_5$ alkyl or unsubstituted 2 to 6 membered heteroalkyl.

9. The compound of claim 1, wherein z2 is 0, 1, or 2.

10. The compound of claim 1, wherein $R^{52}$ is halogen, —OH, —$NH_2$, —COOH, —$CONH_2$, or unsubstituted alkyl.

11. The compound of claim 10, wherein $R^{52}$ is unsubstituted alkyl.

12. The compound of claim 11, wherein $R^{52}$ is unsubstituted $C_1$-$C_5$ alkyl.

13. The compound of claim 1, wherein $R^{52}$ is —$NR^{51A}R^{51B}$, wherein $R^{51A}$ and $R^{51B}$ are independently unsubstituted $C_1$-$C_5$ alkyl.

14. The compound of claim 1, wherein said compound has the formula:

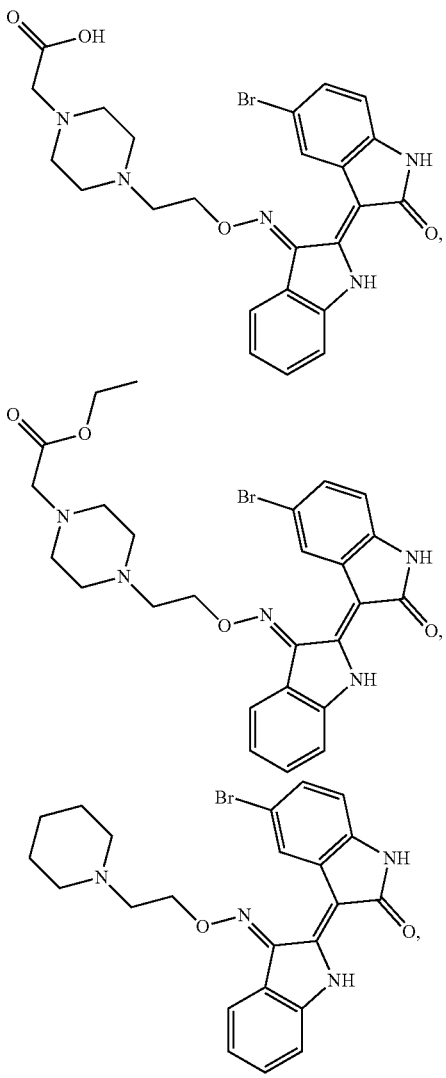

-continued

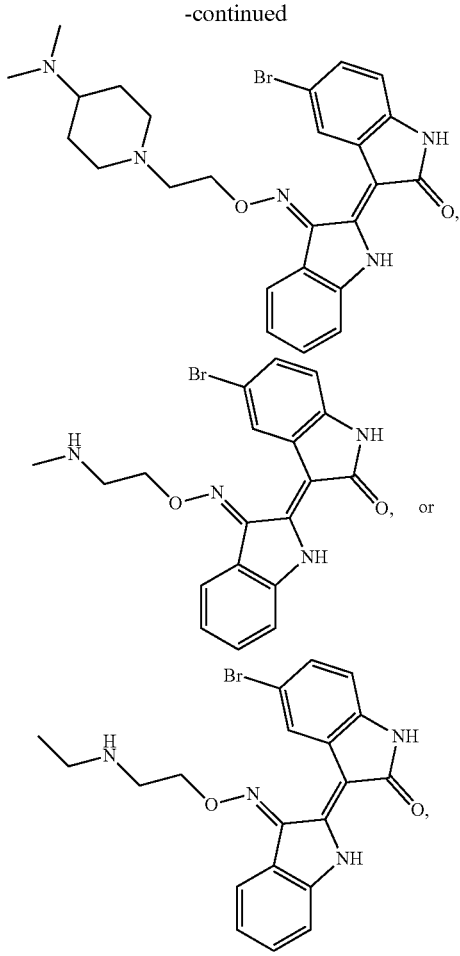

or a pharmaceutically acceptable salt thereof.

15. A method of treating cancer, said method comprising administering to a subject in need thereof an effective amount of a compound having formula:

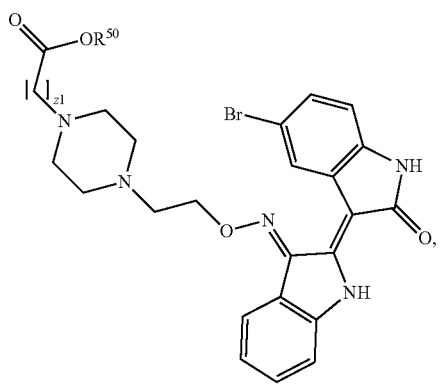

(III)

-continued

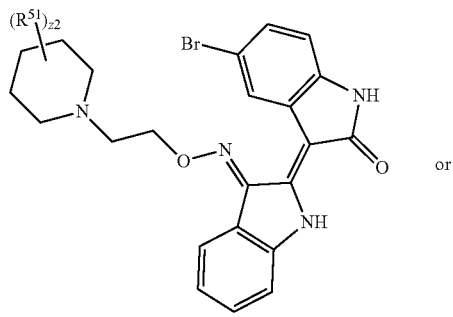

(IV)

or

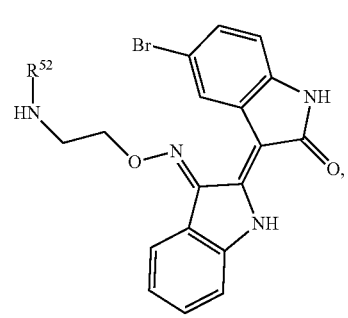

(V)

or a pharmaceutically acceptable salt thereof;
wherein:

$R^{50}$ is hydrogen, oxo, halogen, —$CF_3$, —CN, —OH, —$NH_2$, —COOH, —$CH_2COOH$, —$CONH_2$, —$NO_2$, —SH, —$OCF_3$, —$OCHF_2$, or unsubstituted alkyl;

$R^{51}$ is hydrogen, oxo, halogen, —$CF_3$, —CN, —OH, —$NR^{51A}R^{51B}$ —COOH, —$CH_2COOH$, —$CONH_2$, —$NO_2$, —SH, —$OCF_3$, —$OCHF_2$, unsubstituted alkyl, or unsubstituted heteroalkyl;

$R^{51A}$ and $R^{51B}$ are independently hydrogen or unsubstituted alkyl;

$R^{52}$ is halogen, —$CF_3$, —CN, —OH, —$NH_2$, —COOH, —$CONH_2$, or unsubstituted alkyl; and $z_1$ and $z_2$ are independently 0, 1, 2, 3, 4 or 5;

wherein said cancer is lung cancer, breast cancer, ovarian cancer, leukemia, lymphoma, melanoma, pancreatic cancer, sarcoma, bladder cancer, bone cancer, brain cancer, cervical cancer, colon cancer, esophageal cancer, gastric cancer, liver cancer, head and neck cancer, kidney cancer, myeloma, thyroid cancer, or prostate cancer.

16. A method of treating CML expressing an ABL1-kinase, said method comprising administering to a subject in need thereof an effective amount of a compound of claim 1.

17. The method of claim 16, wherein said ABL1-kinase is a ABL1 mutant-kinase.

18. The method of claim 17, wherein said ABL1 mutant-kinase is a BCR-ABL1 mutant kinase.

* * * * *

SEQUENCE LISTING

<160> NUMBER OF SEQ ID NOS: 3

<210> SEQ ID NO 1
<211> LENGTH: 993
<212> TYPE: PRT
<213> ORGANISM: Homo sapiens

<400> SEQUENCE: 1

```
Met Pro Ala Leu Ala Arg Asp Gly Gly Gln Leu Pro Leu Leu Val Val
1               5                   10                  15

Phe Ser Ala Met Ile Phe Gly Thr Ile Thr Asn Gln Asp Leu Pro Val
                20                  25                  30

Ile Lys Cys Val Leu Ile Asn His Lys Asn Asn Asp Ser Ser Val Gly
                35                  40                  45

Lys Ser Ser Ser Tyr Pro Met Val Ser Glu Ser Pro Glu Asp Leu Gly
            50                  55                  60

Cys Ala Leu Arg Pro Gln Ser Ser Gly Thr Val Tyr Glu Ala Ala Ala
65                  70                  75                  80

Val Glu Val Asp Val Ser Ala Ser Ile Thr Leu Gln Val Leu Val Asp
                85                  90                  95

Ala Pro Gly Asn Ile Ser Cys Leu Trp Val Phe Lys His Ser Ser Leu
                100                 105                 110

Asn Cys Gln Pro His Phe Asp Leu Gln Asn Arg Gly Val Val Ser Met
            115                 120                 125

Val Ile Leu Lys Met Thr Glu Thr Gln Ala Gly Glu Tyr Leu Leu Phe
    130                 135                 140

Ile Gln Ser Glu Ala Thr Asn Tyr Thr Ile Leu Phe Thr Val Ser Ile
145                 150                 155                 160

Arg Asn Thr Leu Leu Tyr Thr Leu Arg Arg Pro Tyr Phe Arg Lys Met
                165                 170                 175

Glu Asn Gln Asp Ala Leu Val Cys Ile Ser Glu Ser Val Pro Glu Pro
```

```
                180                 185                 190
Ile Val Glu Trp Val Leu Cys Asp Ser Gln Gly Glu Ser Cys Lys Glu
            195                 200                 205
Glu Ser Pro Ala Val Val Lys Lys Glu Glu Lys Val Leu His Glu Leu
        210                 215                 220
Phe Gly Thr Asp Ile Arg Cys Cys Ala Arg Asn Glu Leu Gly Arg Glu
225                 230                 235                 240
Cys Thr Arg Leu Phe Thr Ile Asp Leu Asn Gln Thr Pro Gln Thr Thr
                245                 250                 255
Leu Pro Gln Leu Phe Leu Lys Val Gly Glu Pro Leu Trp Ile Arg Cys
            260                 265                 270
Lys Ala Val His Val Asn His Gly Phe Gly Leu Thr Trp Glu Leu Glu
        275                 280                 285
Asn Lys Ala Leu Glu Glu Gly Asn Tyr Phe Glu Met Ser Thr Tyr Ser
        290                 295                 300
Thr Asn Arg Thr Met Ile Arg Ile Leu Phe Ala Phe Val Ser Ser Val
305                 310                 315                 320
Ala Arg Asn Asp Thr Gly Tyr Tyr Thr Cys Ser Ser Ser Lys His Pro
                325                 330                 335
Ser Gln Ser Ala Leu Val Thr Ile Val Glu Lys Gly Phe Ile Asn Ala
            340                 345                 350
Thr Asn Ser Ser Glu Asp Tyr Glu Ile Asp Gln Tyr Glu Glu Phe Cys
        355                 360                 365
Phe Ser Val Arg Phe Lys Ala Tyr Pro Gln Ile Arg Cys Thr Trp Thr
        370                 375                 380
Phe Ser Arg Lys Ser Phe Pro Cys Glu Gln Lys Gly Leu Asp Asn Gly
385                 390                 395                 400
Tyr Ser Ile Ser Lys Phe Cys Asn His Lys His Gln Pro Gly Glu Tyr
                405                 410                 415
Ile Phe His Ala Glu Asn Asp Asp Ala Gln Phe Thr Lys Met Phe Thr
            420                 425                 430
Leu Asn Ile Arg Arg Lys Pro Gln Val Leu Ala Glu Ala Ser Ala Ser
        435                 440                 445
Gln Ala Ser Cys Phe Ser Asp Gly Tyr Pro Leu Pro Ser Trp Thr Trp
        450                 455                 460
Lys Lys Cys Ser Asp Lys Ser Pro Asn Cys Thr Glu Ile Thr Glu
465                 470                 475                 480
Gly Val Trp Asn Arg Lys Ala Asn Arg Lys Val Phe Gly Gln Trp Val
                485                 490                 495
Ser Ser Ser Thr Leu Asn Met Ser Glu Ala Ile Lys Gly Phe Leu Val
            500                 505                 510
Lys Cys Cys Ala Tyr Asn Ser Leu Gly Thr Ser Cys Glu Thr Ile Leu
        515                 520                 525
Leu Asn Ser Pro Gly Pro Phe Pro Phe Ile Gln Asp Asn Ile Ser Phe
        530                 535                 540
Tyr Ala Thr Ile Gly Val Cys Leu Leu Phe Ile Val Val Leu Thr Leu
545                 550                 555                 560
Leu Ile Cys His Lys Tyr Lys Lys Gln Phe Arg Tyr Glu Ser Gln Leu
                565                 570                 575
Gln Met Val Gln Val Thr Gly Ser Ser Asp Asn Glu Tyr Phe Tyr Val
            580                 585                 590
Asp Phe Arg Glu Tyr Glu Tyr Asp Leu Lys Trp Glu Phe Pro Arg Glu
        595                 600                 605
```

Asn Leu Glu Phe Gly Lys Val Leu Gly Ser Gly Ala Phe Gly Lys Val
    610                 615                 620

Met Asn Ala Thr Ala Tyr Gly Ile Ser Lys Thr Gly Val Ser Ile Gln
625                 630                 635                 640

Val Ala Val Lys Met Leu Lys Glu Lys Ala Asp Ser Ser Glu Arg Glu
                645                 650                 655

Ala Leu Met Ser Glu Leu Lys Met Met Thr Gln Leu Gly Ser His Glu
            660                 665                 670

Asn Ile Val Asn Leu Leu Gly Ala Cys Thr Leu Ser Gly Pro Ile Tyr
        675                 680                 685

Leu Ile Phe Glu Tyr Cys Cys Tyr Gly Asp Leu Leu Asn Tyr Leu Arg
    690                 695                 700

Ser Lys Arg Glu Lys Phe His Arg Thr Trp Thr Glu Ile Phe Lys Glu
705                 710                 715                 720

His Asn Phe Ser Phe Tyr Pro Thr Phe Gln Ser His Pro Asn Ser Ser
                725                 730                 735

Met Pro Gly Ser Arg Glu Val Gln Ile His Pro Asp Ser Asp Gln Ile
            740                 745                 750

Ser Gly Leu His Gly Asn Ser Phe His Ser Glu Asp Glu Ile Glu Tyr
        755                 760                 765

Glu Asn Gln Lys Arg Leu Glu Glu Glu Glu Asp Leu Asn Val Leu Thr
    770                 775                 780

Phe Glu Asp Leu Leu Cys Phe Ala Tyr Gln Val Ala Lys Gly Met Glu
785                 790                 795                 800

Phe Leu Glu Phe Lys Ser Cys Val His Arg Asp Leu Ala Ala Arg Asn
                805                 810                 815

Val Leu Val Thr His Gly Lys Val Val Lys Ile Cys Asp Phe Gly Leu
            820                 825                 830

Ala Arg Asp Ile Met Ser Asp Ser Asn Tyr Val Val Arg Gly Asn Ala
        835                 840                 845

Arg Leu Pro Val Lys Trp Met Ala Pro Glu Ser Leu Phe Glu Gly Ile
    850                 855                 860

Tyr Thr Ile Lys Ser Asp Val Trp Ser Tyr Gly Ile Leu Leu Trp Glu
865                 870                 875                 880

Ile Phe Ser Leu Gly Val Asn Pro Tyr Pro Gly Ile Pro Val Asp Ala
                885                 890                 895

Asn Phe Tyr Lys Leu Ile Gln Asn Gly Phe Lys Met Asp Gln Pro Phe
            900                 905                 910

Tyr Ala Thr Glu Glu Ile Tyr Ile Ile Met Gln Ser Cys Trp Ala Phe
        915                 920                 925

Asp Ser Arg Lys Arg Pro Ser Phe Pro Asn Leu Thr Ser Phe Leu Gly
    930                 935                 940

Cys Gln Leu Ala Asp Ala Glu Glu Ala Met Tyr Gln Asn Val Asp Gly
945                 950                 955                 960

Arg Val Ser Glu Cys Pro His Thr Tyr Gln Asn Arg Arg Pro Phe Ser
                965                 970                 975

Arg Glu Met Asp Leu Gly Leu Leu Ser Pro Gln Ala Gln Val Glu Asp
            980                 985                 990

Ser

<210> SEQ ID NO 2
<211> LENGTH: 1130
<212> TYPE: PRT

<213> ORGANISM: Homo sapiens

<400> SEQUENCE: 2

```
Met Leu Glu Ile Cys Leu Lys Leu Val Gly Cys Lys Ser Lys Lys Gly
1               5                   10                  15
Leu Ser Ser Ser Ser Cys Tyr Leu Glu Glu Ala Leu Gln Arg Pro
            20                  25                  30
Val Ala Ser Asp Phe Glu Pro Gln Gly Leu Ser Glu Ala Ala Arg Trp
            35                  40                  45
Asn Ser Lys Glu Asn Leu Leu Ala Gly Pro Ser Glu Asn Asp Pro Asn
            50                  55                  60
Leu Phe Val Ala Leu Tyr Asp Phe Val Ala Ser Gly Asp Asn Thr Leu
65                  70                  75                  80
Ser Ile Thr Lys Gly Glu Lys Leu Arg Val Leu Gly Tyr Asn His Asn
                85                  90                  95
Gly Glu Trp Cys Glu Ala Gln Thr Lys Asn Gly Gln Gly Trp Val Pro
            100                 105                 110
Ser Asn Tyr Ile Thr Pro Val Asn Ser Leu Glu Lys His Ser Trp Tyr
            115                 120                 125
His Gly Pro Val Ser Arg Asn Ala Ala Glu Tyr Leu Leu Ser Ser Gly
            130                 135                 140
Ile Asn Gly Ser Phe Leu Val Arg Glu Ser Glu Ser Ser Pro Gly Gln
145                 150                 155                 160
Arg Ser Ile Ser Leu Arg Tyr Glu Gly Arg Val Tyr His Tyr Arg Ile
                165                 170                 175
Asn Thr Ala Ser Asp Gly Lys Leu Tyr Val Ser Ser Glu Ser Arg Phe
            180                 185                 190
Asn Thr Leu Ala Glu Leu Val His His Ser Thr Val Ala Asp Gly
            195                 200                 205
Leu Ile Thr Thr Leu His Tyr Pro Ala Pro Lys Arg Asn Lys Pro Thr
            210                 215                 220
Val Tyr Gly Val Ser Pro Asn Tyr Asp Lys Trp Glu Met Glu Arg Thr
225                 230                 235                 240
Asp Ile Thr Met Lys His Lys Leu Gly Gly Gly Gln Tyr Gly Glu Val
                245                 250                 255
Tyr Glu Gly Val Trp Lys Lys Tyr Ser Leu Thr Val Ala Val Lys Thr
            260                 265                 270
Leu Lys Glu Asp Thr Met Glu Val Glu Glu Phe Leu Lys Glu Ala Ala
            275                 280                 285
Val Met Lys Glu Ile Lys His Pro Asn Leu Val Gln Leu Leu Gly Val
            290                 295                 300
Cys Thr Arg Glu Pro Pro Phe Tyr Ile Ile Thr Glu Phe Met Thr Tyr
305                 310                 315                 320
Gly Asn Leu Leu Asp Tyr Leu Arg Glu Cys Asn Arg Gln Glu Val Asn
                325                 330                 335
Ala Val Val Leu Leu Tyr Met Ala Thr Gln Ile Ser Ser Ala Met Glu
            340                 345                 350
Tyr Leu Glu Lys Lys Asn Phe Ile His Arg Asp Leu Ala Ala Arg Asn
            355                 360                 365
Cys Leu Val Gly Glu Asn His Leu Val Lys Val Ala Asp Phe Gly Leu
            370                 375                 380
Ser Arg Leu Met Thr Gly Asp Thr Tyr Thr Ala His Ala Gly Ala Lys
385                 390                 395                 400
```

-continued

Phe Pro Ile Lys Trp Thr Ala Pro Glu Ser Leu Ala Tyr Asn Lys Phe
            405                 410                 415

Ser Ile Lys Ser Asp Val Trp Ala Phe Gly Val Leu Leu Trp Glu Ile
        420                 425                 430

Ala Thr Tyr Gly Met Ser Pro Tyr Pro Gly Ile Asp Leu Ser Gln Val
        435                 440                 445

Tyr Glu Leu Leu Glu Lys Asp Tyr Arg Met Glu Arg Pro Glu Gly Cys
    450                 455                 460

Pro Glu Lys Val Tyr Glu Leu Met Arg Ala Cys Trp Gln Trp Asn Pro
465                 470                 475                 480

Ser Asp Arg Pro Ser Phe Ala Glu Ile His Gln Ala Phe Glu Thr Met
                485                 490                 495

Phe Gln Glu Ser Ser Ile Ser Asp Glu Val Glu Lys Glu Leu Gly Lys
            500                 505                 510

Gln Gly Val Arg Gly Ala Val Ser Thr Leu Leu Gln Ala Pro Glu Leu
        515                 520                 525

Pro Thr Lys Thr Arg Thr Ser Arg Arg Ala Ala Glu His Arg Asp Thr
    530                 535                 540

Thr Asp Val Pro Glu Met Pro His Ser Lys Gly Gln Gly Glu Ser Asp
545                 550                 555                 560

Pro Leu Asp His Glu Pro Ala Val Ser Pro Leu Leu Pro Arg Lys Glu
                565                 570                 575

Arg Gly Pro Pro Glu Gly Gly Leu Asn Glu Asp Glu Arg Leu Leu Pro
            580                 585                 590

Lys Asp Lys Lys Thr Asn Leu Phe Ser Ala Leu Ile Lys Lys Lys Lys
        595                 600                 605

Lys Thr Ala Pro Thr Pro Pro Lys Arg Ser Ser Ser Phe Arg Glu Met
    610                 615                 620

Asp Gly Gln Pro Glu Arg Arg Gly Ala Gly Glu Glu Glu Gly Arg Asp
625                 630                 635                 640

Ile Ser Asn Gly Ala Leu Ala Phe Thr Pro Leu Asp Thr Ala Asp Pro
                645                 650                 655

Ala Lys Ser Pro Lys Pro Ser Asn Gly Ala Gly Val Pro Asn Gly Ala
            660                 665                 670

Leu Arg Glu Ser Gly Gly Ser Gly Phe Arg Ser Pro His Leu Trp Lys
        675                 680                 685

Lys Ser Ser Thr Leu Thr Ser Ser Arg Leu Ala Thr Gly Glu Glu Glu
    690                 695                 700

Gly Gly Gly Ser Ser Lys Arg Phe Leu Arg Ser Cys Ser Ala Ser
705                 710                 715                 720

Cys Val Pro His Gly Ala Lys Asp Thr Glu Trp Arg Ser Val Thr Leu
                725                 730                 735

Pro Arg Asp Leu Gln Ser Thr Gly Arg Gln Phe Asp Ser Ser Thr Phe
            740                 745                 750

Gly Gly His Lys Ser Glu Lys Pro Ala Leu Pro Arg Lys Arg Ala Gly
        755                 760                 765

Glu Asn Arg Ser Asp Gln Val Thr Arg Gly Thr Val Thr Pro Pro Pro
    770                 775                 780

Arg Leu Val Lys Lys Asn Glu Glu Ala Ala Asp Glu Val Phe Lys Asp
785                 790                 795                 800

Ile Met Glu Ser Ser Pro Gly Ser Ser Pro Pro Asn Leu Thr Pro Lys
                805                 810                 815

Pro Leu Arg Arg Gln Val Thr Val Ala Pro Ala Ser Gly Leu Pro His

```
                820                 825                 830
Lys Glu Glu Ala Gly Lys Gly Ser Ala Leu Gly Thr Pro Ala Ala Ala
            835                 840                 845

Glu Pro Val Thr Pro Thr Ser Lys Ala Gly Ser Gly Ala Pro Gly Gly
850                 855                 860

Thr Ser Lys Gly Pro Ala Glu Glu Ser Arg Val Arg Arg His Lys His
865                 870                 875                 880

Ser Ser Glu Ser Pro Gly Arg Asp Lys Gly Lys Leu Ser Arg Leu Lys
            885                 890                 895

Pro Ala Pro Pro Pro Pro Ala Ala Ser Ala Gly Lys Ala Gly Gly
            900                 905                 910

Lys Pro Ser Gln Ser Pro Ser Gln Glu Ala Ala Gly Glu Ala Val Leu
            915                 920                 925

Gly Ala Lys Thr Lys Ala Thr Ser Leu Val Asp Ala Val Asn Ser Asp
            930                 935                 940

Ala Ala Lys Pro Ser Gln Pro Gly Glu Gly Leu Lys Lys Pro Val Leu
945                 950                 955                 960

Pro Ala Thr Pro Lys Pro Gln Ser Ala Lys Pro Ser Gly Thr Pro Ile
                965                 970                 975

Ser Pro Ala Pro Val Pro Ser Thr Leu Pro Ser Ala Ser Ala Leu
            980                 985                 990

Ala Gly Asp Gln Pro Ser Ser Thr Ala Phe Ile Pro Leu Ile Ser Thr
            995                 1000                1005

Arg Val Ser Leu Arg Lys Thr Arg Gln Pro Pro Glu Arg Ile Ala
            1010                1015                1020

Ser Gly Ala Ile Thr Lys Gly Val Val Leu Asp Ser Thr Glu Ala
    1025                1030                1035

Leu Cys Leu Ala Ile Ser Arg Asn Ser Glu Gln Met Ala Ser His
    1040                1045                1050

Ser Ala Val Leu Glu Ala Gly Lys Asn Leu Tyr Thr Phe Cys Val
    1055                1060                1065

Ser Tyr Val Asp Ser Ile Gln Gln Met Arg Asn Lys Phe Ala Phe
    1070                1075                1080

Arg Glu Ala Ile Asn Lys Leu Glu Asn Asn Leu Arg Glu Leu Gln
    1085                1090                1095

Ile Cys Pro Ala Thr Ala Gly Ser Gly Pro Ala Ala Thr Gln Asp
    1100                1105                1110

Phe Ser Lys Leu Leu Ser Ser Val Lys Glu Ile Ser Asp Ile Val
    1115                1120                1125

Gln Arg
    1130

<210> SEQ ID NO 3
<211> LENGTH: 1130
<212> TYPE: PRT
<213> ORGANISM: Artificial sequence
<220> FEATURE:
<223> OTHER INFORMATION: Synthetic polypeptide

<400> SEQUENCE: 3

Met Leu Glu Ile Cys Leu Lys Leu Val Gly Cys Lys Ser Lys Lys Gly
1               5                   10                  15

Leu Ser Ser Ser Ser Ser Cys Tyr Leu Glu Glu Ala Leu Gln Arg Pro
            20                  25                  30

Val Ala Ser Asp Phe Glu Pro Gln Gly Leu Ser Glu Ala Ala Arg Trp
```

```
                35                  40                  45
Asn Ser Lys Glu Asn Leu Leu Ala Gly Pro Ser Glu Asn Asp Pro Asn
 50                  55                  60
Leu Phe Val Ala Leu Tyr Asp Phe Val Ala Ser Gly Asp Asn Thr Leu
 65                  70                  75                  80
Ser Ile Thr Lys Gly Glu Lys Leu Arg Val Leu Gly Tyr Asn His Asn
                 85                  90                  95
Gly Glu Trp Cys Glu Ala Gln Thr Lys Asn Gly Gln Gly Trp Val Pro
                100                 105                 110
Ser Asn Tyr Ile Thr Pro Val Asn Ser Leu Glu Lys His Ser Trp Tyr
                115                 120                 125
His Gly Pro Val Ser Arg Asn Ala Ala Glu Tyr Pro Leu Ser Ser Gly
                130                 135                 140
Ile Asn Gly Ser Phe Leu Val Arg Glu Ser Glu Ser Ser Pro Ser Gln
145                 150                 155                 160
Arg Ser Ile Ser Leu Arg Tyr Glu Gly Arg Val Tyr His Tyr Arg Ile
                165                 170                 175
Asn Thr Ala Ser Asp Gly Lys Leu Tyr Val Ser Ser Glu Ser Arg Phe
                180                 185                 190
Asn Thr Leu Ala Glu Leu Val His His Ser Thr Val Ala Asp Gly
                195                 200                 205
Leu Ile Thr Thr Leu His Tyr Pro Ala Pro Lys Arg Asn Lys Pro Thr
210                 215                 220
Val Tyr Gly Val Ser Pro Asn Tyr Asp Lys Trp Glu Met Glu Arg Thr
225                 230                 235                 240
Asp Ile Thr Met Lys His Lys Leu Gly Gly Gly Gln Tyr Gly Glu Val
                245                 250                 255
Tyr Glu Gly Val Trp Lys Lys Tyr Ser Leu Thr Val Ala Val Lys Thr
                260                 265                 270
Leu Lys Glu Asp Thr Met Glu Val Glu Glu Phe Leu Lys Glu Ala Ala
                275                 280                 285
Val Met Lys Glu Ile Lys His Pro Asn Leu Val Gln Leu Leu Gly Val
                290                 295                 300
Cys Thr Arg Glu Pro Pro Phe Tyr Ile Ile Thr Glu Phe Met Thr Tyr
305                 310                 315                 320
Gly Asn Leu Leu Asp Tyr Leu Arg Glu Cys Asn Arg Gln Glu Val Asn
                325                 330                 335
Ala Val Val Leu Leu Tyr Met Ala Thr Gln Ile Ser Ser Ala Met Glu
                340                 345                 350
Tyr Leu Glu Lys Lys Asn Phe Ile His Arg Asp Leu Ala Ala Arg Asn
                355                 360                 365
Cys Leu Val Gly Glu Asn His Leu Val Lys Val Ala Asp Phe Gly Leu
                370                 375                 380
Ser Arg Leu Met Thr Gly Asp Thr Tyr Thr Ala His Ala Gly Ala Lys
385                 390                 395                 400
Phe Pro Ile Lys Trp Thr Ala Pro Glu Ser Leu Ala Tyr Asn Lys Phe
                405                 410                 415
Ser Ile Lys Ser Asp Val Trp Ala Phe Gly Val Leu Leu Trp Glu Ile
                420                 425                 430
Ala Thr Tyr Gly Met Ser Pro Tyr Pro Gly Ile Asp Arg Ser Gln Val
                435                 440                 445
Tyr Glu Leu Leu Glu Lys Asp Tyr Arg Met Lys Arg Pro Glu Gly Cys
                450                 455                 460
```

```
Pro Glu Lys Val Tyr Glu Leu Met Arg Ala Cys Trp Gln Trp Asn Pro
465                 470                 475                 480

Ser Asp Arg Pro Ser Phe Ala Glu Ile His Gln Ala Phe Glu Thr Met
                485                 490                 495

Phe Gln Glu Ser Ser Ile Ser Asp Glu Val Lys Glu Leu Gly Lys
            500                 505                 510

Gln Gly Val Arg Gly Ala Val Thr Thr Leu Leu Gln Ala Pro Glu Leu
        515                 520                 525

Pro Thr Lys Thr Arg Thr Ser Arg Arg Ala Ala Glu His Arg Asp Thr
    530                 535                 540

Thr Asp Val Pro Glu Met Pro His Ser Lys Gly Gln Gly Glu Ser Asp
545                 550                 555                 560

Pro Leu Asp His Glu Pro Ala Val Ser Pro Leu Leu Pro Arg Lys Glu
                565                 570                 575

Arg Gly Pro Pro Glu Gly Gly Leu Asn Glu Asp Glu Arg Leu Leu Pro
            580                 585                 590

Lys Asp Lys Lys Thr Asn Leu Phe Ser Ala Leu Ile Lys Lys Lys
        595                 600                 605

Lys Thr Ala Pro Thr Pro Lys Arg Ser Ser Phe Arg Glu Met
610                 615                 620

Asp Gly Gln Pro Glu Arg Arg Gly Ala Gly Glu Glu Gly Arg Asp
625                 630                 635                 640

Ile Ser Asn Gly Ala Leu Ala Phe Thr Pro Leu Asp Thr Ala Asp Pro
                645                 650                 655

Ala Lys Ser Pro Lys Pro Ser Asn Gly Ala Gly Val Pro Asn Gly Ala
            660                 665                 670

Leu Arg Glu Ser Gly Gly Ser Gly Phe Arg Ser Pro His Leu Trp Lys
        675                 680                 685

Lys Ser Ser Thr Leu Thr Ser Arg Leu Ala Thr Gly Glu Glu Glu
    690                 695                 700

Gly Gly Gly Ser Ser Ser Lys Arg Phe Leu Arg Ser Cys Ser Val Ser
705                 710                 715                 720

Cys Val Pro His Gly Ala Lys Asp Thr Glu Trp Arg Ser Val Thr Leu
                725                 730                 735

Pro Arg Asp Leu Gln Ser Thr Gly Arg Gln Phe Asp Ser Ser Thr Phe
            740                 745                 750

Gly Gly His Lys Ser Glu Lys Pro Ala Leu Pro Arg Lys Arg Ala Gly
        755                 760                 765

Glu Asn Arg Ser Asp Gln Val Thr Arg Gly Thr Val Thr Pro Pro Pro
    770                 775                 780

Arg Leu Val Lys Lys Asn Glu Glu Ala Ala Asp Glu Val Phe Lys Asp
785                 790                 795                 800

Ile Met Glu Ser Ser Pro Gly Ser Ser Pro Pro Asn Leu Thr Pro Lys
                805                 810                 815

Pro Leu Arg Arg Gln Val Thr Val Ala Pro Ala Ser Gly Leu Pro His
            820                 825                 830

Lys Glu Glu Ala Trp Lys Gly Ser Ala Leu Gly Thr Pro Ala Ala Ala
        835                 840                 845

Glu Pro Val Thr Pro Thr Ser Lys Ala Gly Ser Gly Ala Pro Arg Gly
    850                 855                 860

Thr Ser Lys Gly Pro Ala Glu Glu Ser Arg Val Arg Arg His Lys His
865                 870                 875                 880
```

```
Ser Ser Glu Ser Pro Gly Arg Asp Lys Gly Lys Leu Ser Lys Leu Lys
            885                 890                 895

Pro Ala Pro Pro Pro Pro Ala Ala Ser Ala Gly Lys Ala Gly Gly
            900                 905                 910

Lys Pro Ser Gln Arg Pro Gly Gln Glu Ala Ala Gly Glu Ala Val Leu
            915                 920                 925

Gly Ala Lys Thr Lys Ala Thr Ser Leu Val Asp Ala Val Asn Ser Asp
            930                 935                 940

Ala Ala Lys Pro Ser Gln Pro Ala Glu Gly Leu Lys Lys Pro Val Leu
945                 950                 955                 960

Pro Ala Thr Pro Lys Pro His Pro Ala Lys Pro Ser Gly Thr Pro Ile
            965                 970                 975

Ser Pro Ala Pro Val Pro Leu Ser Thr Leu Pro Ser Ala Ser Ser Ala
            980                 985                 990

Leu Ala Gly Asp Gln Pro Ser Ser Thr Ala Phe Ile Pro Leu Ile Ser
            995                 1000                1005

Thr Arg Val Ser Leu Arg Lys Thr Arg Gln Pro Pro Glu Arg Ala
            1010                1015                1020

Ser Gly Ala Ile Thr Lys Gly Val Val Leu Asp Ser Thr Glu Ala
            1025                1030                1035

Leu Cys Leu Ala Ile Ser Gly Asn Ser Glu Gln Met Ala Ser His
            1040                1045                1050

Ser Ala Val Leu Glu Ala Gly Lys Asn Leu Tyr Thr Phe Cys Val
            1055                1060                1065

Ser Tyr Val Asp Ser Ile Gln Gln Met Arg Asn Lys Phe Ala Phe
            1070                1075                1080

Arg Glu Ala Ile Asn Lys Leu Glu Asn Asn Leu Arg Glu Leu Gln
            1085                1090                1095

Ile Cys Pro Ala Ser Ala Gly Ser Gly Pro Ala Ala Thr Gln Asp
            1100                1105                1110

Phe Ser Lys Leu Leu Ser Ser Val Lys Glu Ile Ser Asp Ile Val
            1115                1120                1125

Gln Arg
            1130
```